United States Patent
Zion et al.

(10) Patent No.: US 8,906,850 B2
(45) Date of Patent: Dec. 9, 2014

(54) CRYSTALLINE INSULIN-CONJUGATES

(75) Inventors: Todd C. Zion, Marblehead, MA (US); Thomas M. Lancaster, Stoneham, MA (US)

(73) Assignee: Smartcells, Inc., Beverly, MA (US)

( * ) Notice: Subject to any disclaimer, the term of this patent is extended or adjusted under 35 U.S.C. 154(b) by 279 days.

(21) Appl. No.: 13/145,525

(22) PCT Filed: Jan. 27, 2010

(86) PCT No.: PCT/US2010/022277
§ 371 (c)(1),
(2), (4) Date: Jul. 20, 2011

(87) PCT Pub. No.: WO2010/088300
PCT Pub. Date: Aug. 5, 2010

(65) Prior Publication Data
US 2011/0281791 A1 Nov. 17, 2011

Related U.S. Application Data

(60) Provisional application No. 61/147,878, filed on Jan. 28, 2009, provisional application No. 61/159,643, filed on Mar. 12, 2009, provisional application No. 61/162,107, filed on Mar. 20, 2009, provisional application No. 61/163,084, filed on Mar. 25, 2009, provisional application No. 61/219,896, filed on Jun. 24, 2009, provisional application No. 61/219,897, filed on Jun. 24, 2009, provisional application No. 61/223,572, filed on Jul. 7, 2009, provisional application No. 61/252,857, filed on Oct. 19, 2009.

(51) Int. Cl.
*A61K 38/28* (2006.01)
*C07K 14/62* (2006.01)

(52) U.S. Cl.
USPC .......................................... 514/5.9; 530/345

(58) Field of Classification Search
USPC .......................................... 514/5.9; 530/345
See application file for complete search history.

(56) References Cited

U.S. PATENT DOCUMENTS

| | | |
|---|---|---|
| 3,591,574 A | 7/1971 | Fenichel et al. |
| 3,684,791 A | 8/1972 | Geiger et al. |
| 3,847,890 A | 11/1974 | Green et al. |
| 4,348,387 A | 9/1982 | Brownlee et al. |
| 4,372,948 A | 2/1983 | Yoshikumi et al. |
| 4,377,567 A | 3/1983 | Geho |
| 4,444,683 A | 4/1984 | Kim et al. |
| 4,603,044 A | 7/1986 | Geho et al. |
| 4,863,896 A | 9/1989 | Geho et al. |
| 5,239,062 A | 8/1993 | Blattler et al. |
| 5,395,924 A | 3/1995 | Blattler et al. |
| 5,478,575 A | 12/1995 | Miyazaki et al. |
| 5,527,524 A | 6/1996 | Tomalia et al. |
| 5,563,056 A | 10/1996 | Swan et al. |
| 5,723,589 A | 3/1998 | Miljkovic et al. |
| 5,830,506 A | 11/1998 | Taylor |
| 5,854,208 A | 12/1998 | Jones et al. |
| 5,866,538 A | 2/1999 | Norup et al. |
| 5,902,607 A | 5/1999 | Taylor |
| 5,905,140 A | 5/1999 | Hansen |
| 5,922,675 A | 7/1999 | Baker et al. |
| 5,948,751 A | 9/1999 | Kimer et al. |
| 5,994,517 A | 11/1999 | Ts'o et al. |
| 6,034,054 A | 3/2000 | DeFelippis et al. |
| 6,180,757 B1 | 1/2001 | Bogsnes |
| 6,214,547 B1 | 4/2001 | Kjeldsen et al. |
| 6,323,311 B1 | 11/2001 | Liu et al. |
| 6,342,225 B1 | 1/2002 | Jones et al. |
| 6,410,053 B1 | 6/2002 | Taylor |
| 6,500,645 B1 | 12/2002 | Kjeldsen et al. |
| 6,521,738 B2 | 2/2003 | Kjeldsen et al. |
| 6,551,992 B1 | 4/2003 | DeFelippis et al. |
| 6,777,207 B2 | 8/2004 | Kjeldsen et al. |
| 6,844,166 B1 | 1/2005 | Wolf |
| 6,869,930 B1 | 3/2005 | Havelund et al. |
| RE39,055 E | 4/2006 | Jones et al. |
| 7,063,863 B2 | 6/2006 | Taylor |
| 7,087,408 B2 | 8/2006 | Kjeldsen et al. |
| 7,105,314 B2 | 9/2006 | Kjeldsen |
| 7,316,999 B2 | 1/2008 | Hoeg-Jensen et al. |
| 7,317,000 B2 | 1/2008 | Hoeg-Jensen et al. |
| 7,423,014 B2 | 9/2008 | Ekwuribe et al. |
| 7,531,191 B2 | 5/2009 | Zion et al. |
| 7,687,608 B2 | 3/2010 | Lancaster et al. |
| 2006/0019874 A1* | 1/2006 | Radhakrishnan et al. ........ 514/3 |
| 2006/0216265 A1 | 9/2006 | Goodman et al. |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

Vanbever, Sustained Release of Insulin From Insoluble Inhaled Particles, Drug Development Research 48:178-185, 1999.*
Baudys, et al., "Physical Stabilization of Insulin by Glycosylation" *J Pharma Sci* (1995) 64: 28-33.
Brownlee & Cerami, "A Glucose-Controlled-Insulin-Delivery-System: Semisynthetic Insulin Bound to Lectin" *Diabetes* (1983) 32: 499-504.
Brownlee & Cerami, "Glycosylated Insulin Complexed to Concanavalin A" *Science* (1979) 206: 1190-1191.
Dea, et al., "Albumin Binding of Acylated Insulin (NN304) Does Not Deter Action to Stimulate Glucose Uptake" *Diabetes* (2002) 51: 762-769.
Eggert, et al., "A New Glucose Selective Fluorescent Bisboronic Acid" *J Org Chem* (1999) 64: 3846-3852.
Heinnemann, et al., "Time-action profile of the soluble, fatty acid acylated, long acting insulin analogue NN304" *Diabetic Med* (1999) 16: 332-338.

(Continued)

*Primary Examiner* — David Lukton
(74) *Attorney, Agent, or Firm* — John David Reilly; Immac J. Thampoe

(57) ABSTRACT

The present disclosure provides crystalline insulin-conjugates. The present disclosure also provides formulations, methods of treatment, methods of administering, and methods of making that encompass these crystalline insulin-conjugates.

15 Claims, 47 Drawing Sheets

(56) References Cited

U.S. PATENT DOCUMENTS

| | | | |
|---|---|---|---|
| 2006/0247154 A1 | 11/2006 | Palmieri et al. | |
| 2007/0099820 A1* | 5/2007 | Lancaster et al. | 514/3 |
| 2007/0207498 A1 | 9/2007 | Palmieri et al. | |
| 2009/0053167 A1 | 2/2009 | DeFrees | |
| 2009/0137454 A1 | 5/2009 | Fynbo et al. | |

FOREIGN PATENT DOCUMENTS

| | | |
|---|---|---|
| EP | 0119650 | 9/1984 |
| EP | 0725648 | 8/1996 |
| RU | 2381238 | 8/2009 |
| WO | WO81/00354 | 2/1981 |
| WO | WO84/01896 | 5/1984 |
| WO | WO90/10645 | 9/1990 |
| WO | WO99/52934 | 10/1999 |
| WO | WO01/92334 | 12/2001 |
| WO | WO03/035011 | 5/2003 |
| WO | WO03/047462 | 6/2003 |
| WO | WO03/048915 | 6/2003 |
| WO | WO03/074087 | 9/2003 |
| WO | WO2004/057002 | 7/2004 |
| WO | 2004/101619 | 11/2004 |
| WO | WO2006/008238 | 1/2006 |
| WO | WO 2006062685 A2 * | 6/2006 |
| WO | WO2006/082184 | 8/2006 |
| WO | WO2006/088473 | 8/2006 |
| WO | WO2006/102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2009/033588 | 3/2009 |
| WO | WO2009/059450 | 5/2009 |
| WO | WO2009/089396 | 7/2009 |
| WO | WO2009/104199 | 8/2009 |
| WO | WO2011/000823 | 1/2011 |

OTHER PUBLICATIONS

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoyl Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

International Search Report and Written Opinion for PCT/US10/22277, mailed on Apr. 12, 2010.

U.S. Appl. No. 13/145,532 Reply to Office Action—dated Oct. 10, 2013.

Jansen et al., Infection & Immunity, vol. 69, No. 2, 2001, pp. 787-793.

Kanbe et al., International Journal of Hematology, vol. 74, 2001, pp. 309-315.

Takata et al., Journal of Leukocyte Biology, vol. 41, 1987, pp. 248-256.

U.S. Appl. No. 13/145,532 Final Office Action—dated Mar. 6, 2014.

U.S. Appl. No. 13/145,532 Non-Final Office Action—dated Jul. 10, 2013.

U.S. Appl. No. 13/145,532 Reply to Final Office Action—dated Jun. 6, 2014.

WO 2004/101619—Machine Translation.

* cited by examiner

Conjugate I-5
TSAT-C6-GA-2 (B29)

Conjugate I-6
TSAT-C6-AETM-2 (B29)

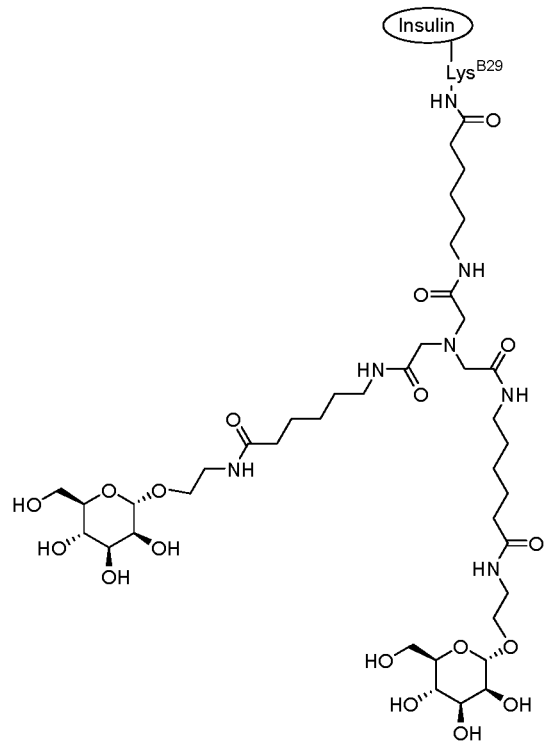
Conjugate I-7
TSAT-C6-AEM-2 (B29)
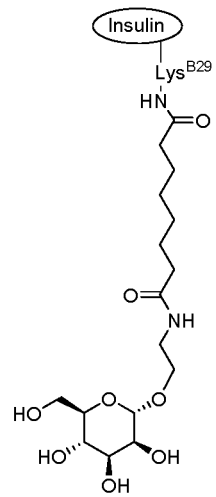
Conjugate I-8
DSS-AEM-1 (B29)
Figure 2 (continued)

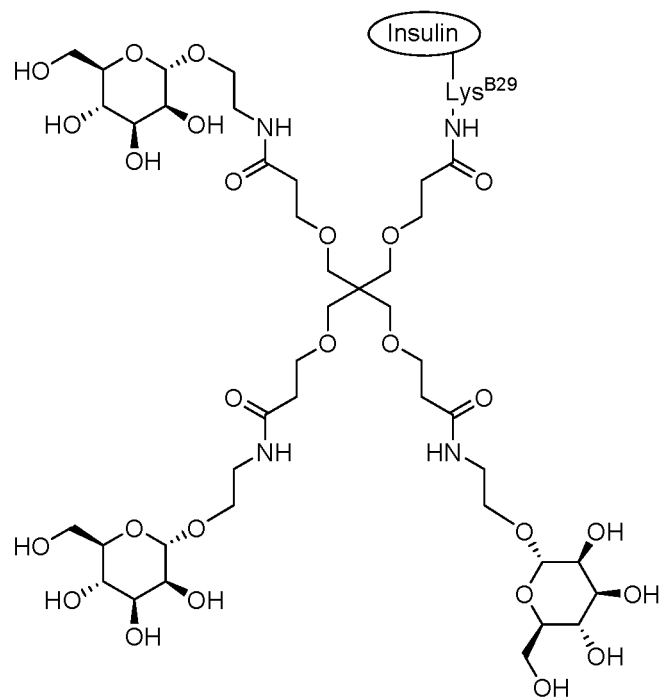
Conjugate I-9
TSPE-AEM-3 (B29)
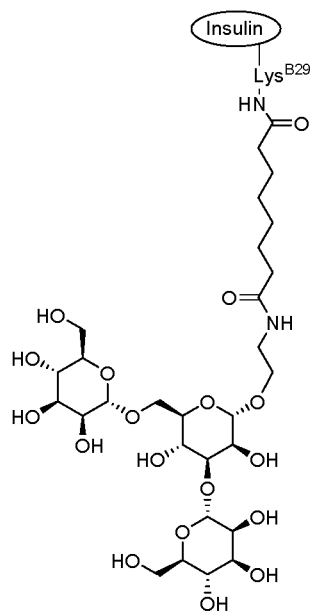
Conjugate I-10
DSS-AETM-1 (B29)
Figure 2 (continued)

Conjugate I-11
TSPE-AETM-3 (B29)

Conjugate I-17
C6-Amide-AEM-2 (B29)

| Buffer | Score |
|---|---|
| 1. 0.1 M Citric acid pH 3.5, 2.0 M Ammonium sulfate | 3 |
| 2. 0.1 M Sodium acetate trihydrate pH 4.5, 2.0 M Ammonium sulfate | 4 |
| 3. 0.1 M BIS-TRIS pH 5.5, 2.0 M Ammonium sulfate | 1 |
| 4. 0.1 M BIS-TRIS pH 6.5, 2.0 M Ammonium sulfate | 3 |
| 5. 0.1 M HEPES pH 7.5, 2.0 M Ammonium sulfate | 3 |
| 6. 0.1 M Tris pH 8.5, 2.0 M Ammonium sulfate | 3 |
| 7. 0.1 M Citric acid pH 3.5, 3.0 M Sodium chloride | 1 |
| 8. 0.1 M Sodium acetate trihydrate pH 4.5, 3.0 M Sodium chloride | 1 |
| 9. 0.1 M BIS-TRIS pH 5.5, 3.0 M Sodium chloride | 1 |
| 10. 0.1 M BIS-TRIS pH 6.5, 3.0 M Sodium chloride | 1 |
| 11. 0.1 M HEPES pH 7.5, 3.0 M Sodium chloride | 8 |
| 12. 0.1 M Tris pH 8.5, 3.0 M Sodium chloride | 1 |
| 13. 0.1 M BIS-TRIS pH 5.5, 0.3 M Magnesium formate dihydrate | 1 |
| 14. 0.1 M BIS-TRIS pH 6.5, 0.5 M Magnesium formate dihydrate | 1 |
| 15. 0.1 M HEPES pH 7.5, 0.5 M Magnesium formate dihydrate | 8 |
| 16. 0.1 M Tris pH 8.5, 0.3 M Magnesium formate dihydrate | 1 |
| 17. 1.26 M Sodium phosphate monobasic monohydrate, 0.14 M Potassium phosphate dibasic, pH 5.6 | 1 |
| 18. 0.49 M Sodium phosphate monobasic monohydrate, 0.91 M Potassium phosphate dibasic, pH 6.9 | 1 |
| 19. 0.056 M Sodium phosphate monobasic monohydrate, 1.344 M Potassium phosphate dibasic, pH 8.2 | 8 |
| 20. 0.1 M HEPES pH 7.5, 1.4 M Sodium citrate tribasic dihydrate | 3 |
| 21. 1.8 M Ammonium citrate tribasic pH 7.0 | 3 |
| 22. 0.8 M Succinic acid pH 7.0 | 1 |
| 23. 2.1 M DL-Malic acid pH 7.0 | 3 |
| 24. 2.8 M Sodium acetate trihydrate pH 7.0 | 1 |
| 25. 3.5 M Sodium formate pH 7.0 | 1 |
| 26. 1.1 M Ammonium tartrate dibasic pH 7.0 | 3 |
| 27. 2.4 M Sodium malonate pH 7.0 | 1 |
| 28. 35% v/v Tacsimate pH 7.0 | 3 |
| 29. 60% v/v Tacsimate pH 7.0 | 1 |

Legend:

| 1 | Clear drop | 5 | Posettes or Spherulites |
|---|---|---|---|
| 2 | Phase separation | 6 | Needles (1D growth) |
| 3 | Regular granular precipitate | 7 | Plates (2D growth) |
| 4 | Birefringent Precipitate or Microcrystals | 8 | Single crystals (3D growth < 0.2 mm) |
|  |  | 9 | Single crystals (3D growth > 0.2 mm) |

Figure 27

| Buffer | Score |
|---|---|
| 30. 0.1 M Sodium chloride, 0.1 M BIS-TRIS pH 6.5, 1.5 M Ammonium sulfate | 1 |
| 31. 0.8 M Potassium sodium tartrate tetrahydrate, 0.1 M Tris pH 8.5, 0.5% w/v Polyethylene glycol monomethyl ether 5,000 | 1→3 |
| 32. 1.0 M Ammonium sulfate, 0.1 M BIS-TRIS pH 5.5, 1% w/v Polyethylene glycol 3,350 | 4 |
| 33. 1.1 M Sodium malonate pH 7.0, 0.1 M HEPES pH 7.0, 0.5% v/v Jeffamine ED-2001® pH 7.0 | 1 |
| 34. 1.0 M Succinic acid pH 7.0, 0.1 M HEPES pH 7.0, 1% w/v Polyethylene glycol monomethyl ether 2,000 | 1 |
| 35. 1.0 M Ammonium sulfate, 0.1 M HEPES pH 7.0, 0.5% w/v Polyethylene glycol 8,000 | 1 |
| 36. 15% v/v Tacsimate pH 7.0, 0.1 M HEPES pH 7.0, 2% w/v Polyethylene glycol 3,350 | 1 |
| 37. 25% w/v Polyethylene glycol 1,500 | 3 |
| 38. 0.1 M HEPES pH 7.0, 30% v/v Jeffamine M-600® pH 7.0 | 7 |
| 39. 0.1 M HEPES pH 7.0, 30% v/v Jeffamine ED-2001 ® pH 7.0 | 1 |
| 40. 0.1 M Citric acid pH 3.5, 25% w/v Polyethylene glycol 3,350 | 6 |
| 41. 0.1 M Sodium acetate trihydrate pH 4.5, 25% w/v Polyethylene glycol 3,350 | 3 |
| 42. 0.1 M BIS-TRIS pH 5.5, 25% w/v Polyethylene glycol 3,350 | 3/5 |
| 43. 0.1 M BIS-TRIS pH 6.5, 25% w/v Polyethylene glycol 3,350 | 1 |
| 44. 0.1 M HEPES pH 7.5, 25% w/v Polyethylene glycol 3,350 | 1 |
| 45. 0.1 M Tris pH 8.5, 25% w/v Polyethylene glycol 3,350 | 1 |
| 46. 0.1 M BIS-TRIS pH 6.5, 20% w/v Polyethylene glycol monomethyl ether 5,000 | 1 |
| 47. 0.1 M BIS-TRIS pH 6.5, 28% w/v Polyethylene glycol monomethyl ether 2,000 | 1 |
| 48. 0.2 M Calcium chloride dihydrate, 0.1 M BIS-TRIS pH 5.5, 45% v/v (+/-)-2-Methyl-2,4-pentanediol | 1 |

Legend:

| 1 | Clear drop | 5 | Posettes or Spherulites |
|---|---|---|---|
| 2 | Phase separation | 6 | Needles (1D growth) |
| 3 | Regular granular precipitate | 7 | Plates (2D growth) |
| 4 | Birefringent Precipitate or Microcrystals | 8 | Single crystals (3D growth < 0.2 mm) |
| | | 9 | Single crystals (3D growth > 0.2 mm) |

Figure 27 (continued)

CRYSTALLINE INSULIN-CONJUGATES

RELATED APPLICATIONS

This application is a national phase application of International Application No. PCT/US2010/22277, filed Jan. 27, 2010, which claims priority to U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/163,084 filed Mar. 25, 2009, U.S. Provisional Application No. 61/219,896 filed Jun. 24, 2009, U.S. Provisional Application No. 61/219,897 filed Jun. 24, 2009, U.S. Provisional Application No. 61/223,572 filed Jul. 7, 2009, and U.S. Provisional Application No. 61/252,857 filed Oct. 19, 2009, the content of each of which is hereby incorporated by reference in its entirety.

In accordance with 37 CFR 1.52(e)(5), a Sequence Listing in the form of a text file (entitled "Sequence listing_0032.txt," created on Jan. 25, 2010, and 1 kilobyte) is incorporated herein by reference in its entirety.

BACKGROUND

The majority of "controlled-release" drug delivery systems known in the prior art (e.g., U.S. Pat. No. 4,145,410 to Sears which describes drug release from capsules which are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of certain types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if an alternative controlled drug delivery system could be provided that did not require lectins.

SUMMARY

In one aspect, the disclosure provides methods for controlling the pharmacokinetic (PK) and/or pharmacodynamic (PD) profiles of insulin in a manner that is responsive to the systemic concentrations of a saccharide such as glucose. As discussed in the Examples, we have discovered that when insulin was conjugated to high affinity saccharide ligands it could be made to exhibit PK/PD profiles that responded to saccharide concentration changes even in the absence of an exogenous multivalent saccharide-binding molecule such as Con A. This finding was unexpected and provides an unprecedented opportunity to generate simple lectin-free saccharide-responsive insulin systems.

Sustained release formulations of conventional insulins are commonly used in order to slow the insulin release into systemic circulation. For example, PZI (protamine zinc insulin) formulations may be used for this purpose. When conventional insulins are formulated with protamine and zinc, crystalline sustained release formulations are generally produced. In contrast, when insulin-conjugates described herein are formulated with protamine and zinc using similar methods, amorphous formulations are produced, and much more protamine and zinc is required to provide sustained release than is required for conventional insulins, e.g. RHI. We have surprisingly found that certain insulin-conjugates described herein can be crystallized. Insulin-conjugates are difficult to crystallize using standard insulin crystallization conditions, most likely due to their saccharide-containing, sterically bulky structures. As described herein, the crystalline insulin-conjugates of the present disclosure can then be formulated to provide crystalline sustained release formulations. The present disclosure provides crystalline insulin-conjugates and formulations thereof. Also provided are methods of making and using crystalline insulin-conjugates. Crystalline formulations of insulin-conjugates may be advantageous in improving batch to batch reproducibility, increasing formulation stability, and decreasing particle agglomeration over long periods of storage.

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —(CH$_2$)$_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^°$; —$(CH_2)_{0-4}OR^°$; —O—$(CH_2)_{0-4}C(O)OR^°$; —$(CH_2)_{0-4}CH(OR^°)_2$; —$(CH_2)_{0-4}SR^°$; —$(CH_2)_{0-4}Ph$, which may be substituted with $R^°$; —$(CH_2)_{0-4}O(CH_2)_{0-1}Ph$ which may be substituted with $R^°$; —CH=CHPh, which may be substituted with $R^°$; —$NO_2$; —CN; —$N_3$; —$(CH_2)_{0-4}N(R^°)_2$; —$(CH_2)_{0-4}N(R^°)C(O)R^°)$; —$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —C(S)R^°$; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}OC(O)R^°$; —OC(O)$(CH_2)_{0-4}SR$—, SC(S)SR^°$; —$(CH_2)_{0-4}SC(O)R^°$; —$(CH_2)_{0-4}C(O)NR^°_2$; —C(S)NR^°_2$;

—C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°); —N(R°)S(O)$_2$NR°$_2$); —N(R°)S(O)$_2$R°); —N(OR°R°; —C(NH)NR°$_2$; —P(O)$_2$R°; —P(O)R°$_2$; —OP(O)R°$_2$); —OP(O)(OR°$_2$); SiR°$_3$; —(C$_{1-4}$ straight or branched)alkylene)O—N(R°$_2$; or —(C$_{1-4}$ straight or branched)alkylene)C(O)O—N(R°$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —C(O)SR$^\bullet$$_3$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR*), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2- dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms) β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Exogenous—As used herein, an "exogenous" molecule is one which is not present at significant levels in a patient unless administered to the patient. In certain embodiments the patient is a mammal, e.g., a human, a dog, a cat, a rat, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal serum—As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Treat—As used herein, the term "treat" (or "treating", "treated", "treatment", etc.) refers to the administration of an insulin-conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWINGS

FIG. 27: Index Buffer solutions for crystallization and visual observation results using microscopy.

DETAILED DESCRIPTION OF VARIOUS EMBODIMENTS

This application refers to a number of documents including patent and non-patent documents. The entirety of each of these documents is incorporated herein by reference.

In one aspect, the disclosure provides methods for controlling the pharmacokinetic (PK) and/or pharmacodynamic (PD) profiles of insulin in a manner that is responsive to the systemic concentrations of a saccharide such as glucose. As discussed herein, these methods are based in part on the discovery that certain synthetic insulin-conjugates that include high affinity saccharide ligands (e.g., see those in FIG. 1) exhibit PK/PD profiles that respond to saccharide concentration changes even in the absence of an exogenous multivalent saccharide-binding molecule such as Con A. This finding was unexpected and provided an unprecedented opportunity to generate simple lectin-free saccharide-responsive insulin systems.

Figure 2:
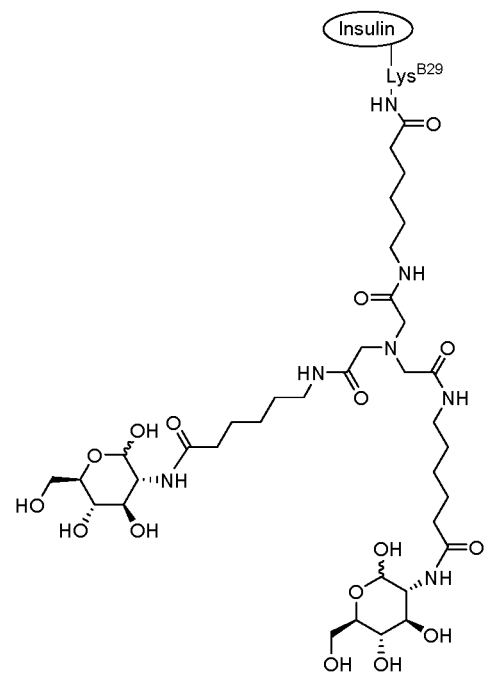
FIG. 2: Structures of exemplary B29 insulin-conjugates. As described in the Examples, these conjugates were each prepared with recombinant wild-type human insulin (see FIG. 33 for the structure of wild-type human insulin). The symbol "insulin" inside an oval as shown in FIG. 2 is therefore primarily intended to represent a wild-type human insulin. As discussed herein, it is to be understood that the present disclosure also encompasses inter alia versions of these and other conjugates that include an insulin molecule other than wild-type human insulin.
Figure 2:
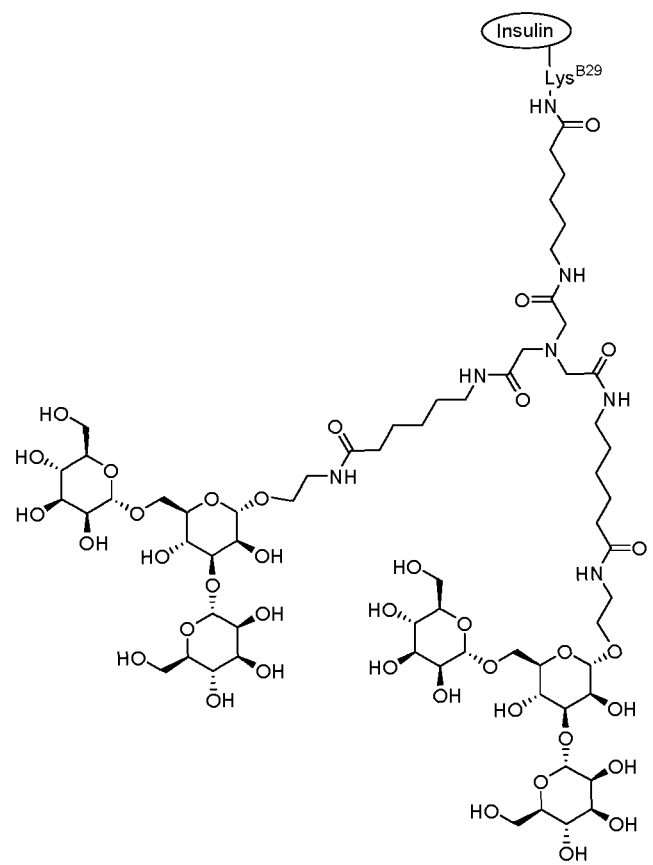
Figure 2:
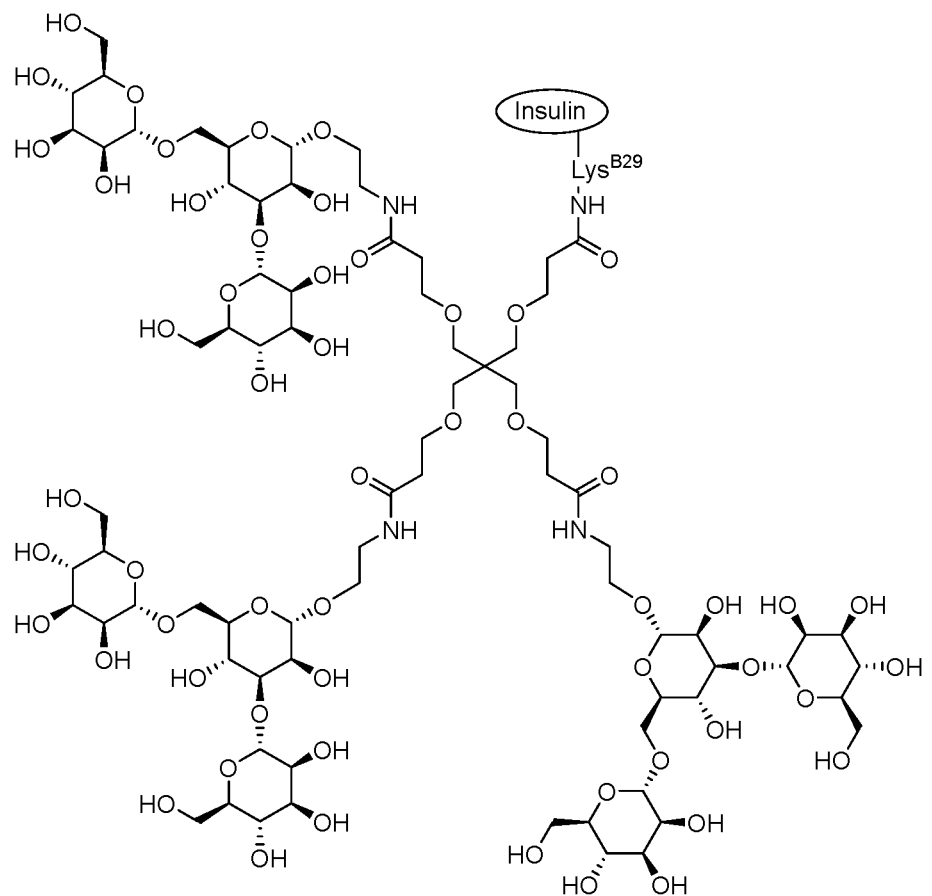
Figure 2:
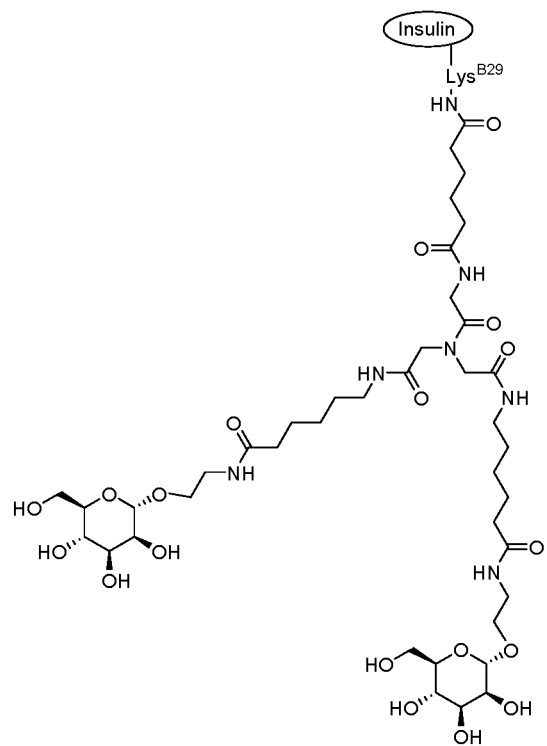

One example of such an insulin-conjugate, known as I-6, is shown in FIG. 2. Conjugate I-6 comprises a discrete, low molecular weight synthetic framework (tris-succinimidyl (6-aminocaproyl)aminotriacetate or TSAT-C6) with two aminoethyltrimannose (AETM) saccharide moieties. The framework is covalently conjugated to insulin via the B29 epsilon-amino group (wild-type human insulin has a lysine residue at position B29). As discussed in the Examples, insulin-conjugates such as I-6 exhibit glucose-responsive pharmacokinetics. As a result, the availability and therefore the bioactivity, of insulin-conjugates such as I-6 vary in response to endogenous glucose levels. We have prepared sustained release formulations of conjugate I-6 using protamine and zinc (PZI formulations) that provide both basal and bolus insulin "delivery" on demand without inducing hypoglycemia. In contrast, conventional insulins are either rapid-acting (e.g., RHI) or slow-acting (e.g., Lantus) and cannot change profiles in response to changes in glucose levels. When compared with conventional insulin in diabetic and normal rats, conjugate I-6 shows a substantially improved therapeutic window, with minimal risk of hypoglycemia at four times the therapeutic dose.

Significantly, our studies have shown that the TSAT-C6 framework employed by conjugate I-6 is not required for glucose-responsive activity. Indeed, as shown in the Examples, we have found that other insulin-conjugated frameworks such as those depicted in FIGS. 1 and 2 can provide similar results. Our studies also suggest that the type and number of conjugated sugars and, in certain situations, the point of conjugation on the insulin molecule play a more important role in modulating the in vivo glucose-response.

Figure 1:
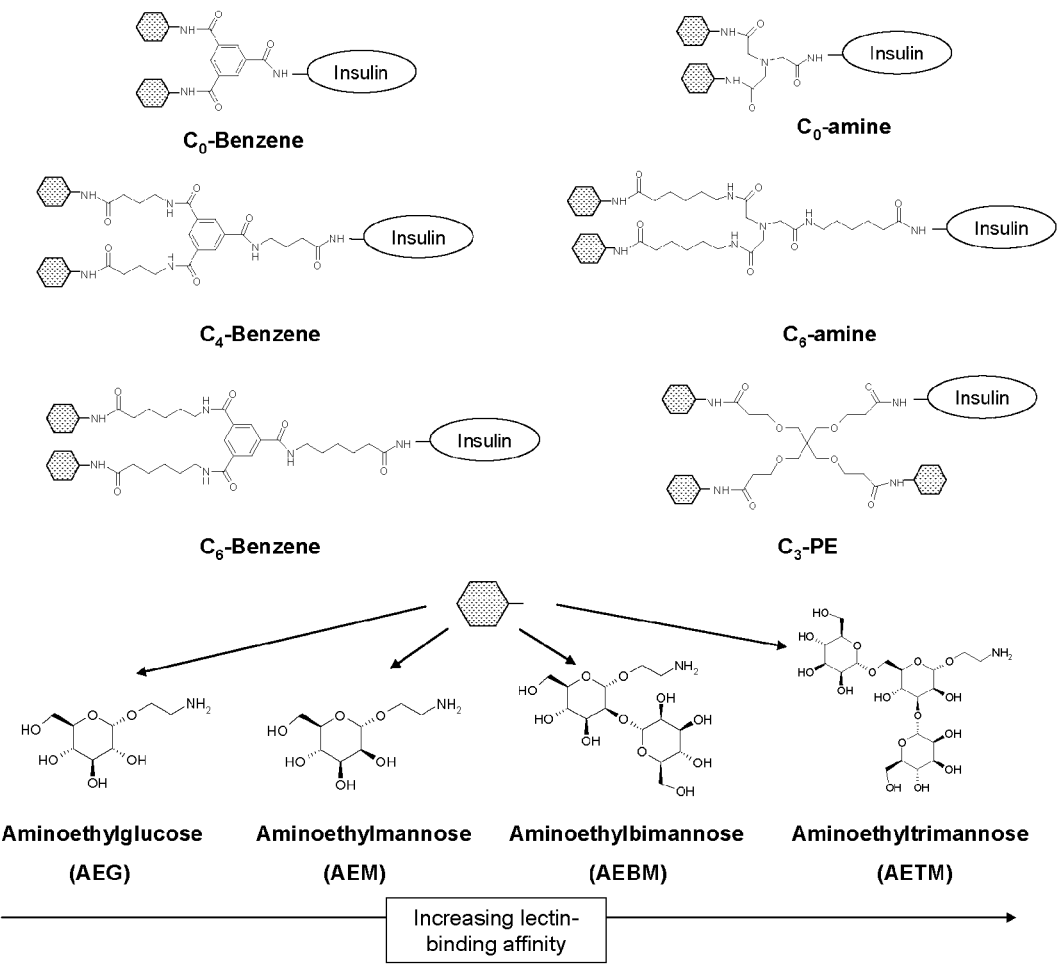
FIG. 1: Chemical structures of exemplary insulin-conjugate frameworks and ligands.

Without wishing to be bound by any particular theory, it is believed that the glucose-responsiveness exhibited by conjugates such as I-6 is mediated by binding to endogenous lectins. Thus, we theorize that when glucose levels in the body are low, the endogenous lectins have glucose binding sites available for binding by the synthetic insulin-conjugate, essentially inactivating the insulin-like activity of the conjugate. Conversely, when glucose levels in the body are high, the binding sites on the lectins are satisfied by endogenous glucose, thus allowing the synthetic insulin-conjugate to circulate and exert its effect. FIG. 1 shows the relative lectin binding affinities of four sugars; AETM binds lectins with the highest affinity of the four sugars shown. We theorize that the lectin binding affinity of a particular sugar is responsible at least in part for the modulation of in vivo glucose-responsiveness of our synthetic insulin-conjugates.

Sustained release formulations of conventional insulins are commonly used in order to slow the insulin release into systemic circulation. For example, PZI (protamine zinc insulin) formulations may be used for this purpose. When conventional insulins are formulated with protamine and zinc, crystalline sustained release formulations are generally produced. In contrast, when insulin-conjugates such as I-6 are formulated with protamine and zinc using similar methods, amorphous formulations are produced, and much more protamine and zinc is required to provide sustained release than is required for conventional insulins, e.g., RHI. We have surprisingly found that insulin-conjugates such as I-6 can be crystallized in the absence of additives such as protamine or zinc, unlike conventional insulins. As described herein, these crystalline insulin-conjugates can then be formulated to provide crystalline sustained release formulations. Crystalline formulations of insulin-conjugates may be advantageous in improving batch to batch reproducibility, increasing formulation stability, and decreasing particle agglomeration over long periods of storage.

Conjugates

In one aspect, the disclosure provides crystalline conjugates that comprise an insulin molecule and a ligand that includes a first saccharide. The ligand or ligands are such that when the crystalline insulin-conjugate is administered to a mammal at least one pharmacokinetic or pharmacodynamic property of the conjugate is sensitive to the serum concentration of a second saccharide. In certain embodiments, the PK and/or PD properties of the conjugate are sensitive to the serum concentration of an endogenous saccharide such as glucose. In certain embodiments, the PK and/or PD properties of the conjugate are sensitive to the serum concentration of an exogenous saccharide, e.g., without limitation, mannose, L-fucose, N-acetyl glucosamine and/or alpha-methyl mannose.

In certain embodiments, the molecular weight of the conjugate absent the insulin is less than about 10,000 Da. For example, the molecular weight of the conjugate absent the insulin may be in the range of about 250 to about 5,000 Da, about 450 to about 3,500 Da, about 750 to about 2,500 Da, or about 900 to about 2,000 Da.

In certain embodiments, the molecular weight of the conjugate including the insulin is less than about 20,000 Da. For example, the molecular weight of the conjugate including the insulin may be in the range of about 2,000 to about 18,000 Da, about 4,000 to about 15,000 Da, about 5,000 to about 10000 Da, or about 6,500 to about 8,000 Da.

In certain embodiments, the conjugate has a unique molecular weight (i.e., has a polydispersity index of one).

PK and PD Properties

In various embodiments, the pharmacokinetic and/or pharmacodynamic behavior of a crystalline insulin-conjugate may be modified by variations in the serum concentration of a saccharide.

For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In certain embodiments, the serum concentration curve of a crystalline insulin-conjugate is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In certain embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In certain embodiments, the conjugate and glucose are administered by different routes or at different locations. For example, in certain embodiments, the conjugate is administered subcutaneously while glucose is administered orally or intravenously.

In certain embodiments, the serum $C_{max}$ of the conjugate is higher under hyperglycemic conditions as compared to fasted conditions. Additionally or alternatively, in certain embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. As discussed in the Examples, we have found that in certain embodiments, the serum concentration curve of the conjugates can be fit using a two-compartment bi-exponential model with one short and one long half-life. The long half-life appears to be particularly sensitive to glucose concentration. Thus, in certain embodiments, the long half-life is longer under hyperglycemic conditions as compared to fasted conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In certain embodiments, the PK properties of the conjugate may be tested using a glucose clamp method and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in certain embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in certain embodiments, the $C_{max}$ of the conjugate is higher when administered to the mammal at the higher of the two glucose concentrations (e.g., 300 vs. 100 mg/dL glucose). In certain embodiments, the $C_{max}$ of the conjugate is at least 50% (e.g., at least 100%, at least 200% or at least 400%) higher when administered to the mammal at the higher of the two glucose concentrations (e.g., 300 vs. 100 mg/dL glucose).

In certain embodiments, the AUC of the conjugate is higher when administered to the mammal at the higher of the two glucose concentrations (e.g., 300 vs. 100 mg/dL glucose). In certain embodiments, the AUC of the conjugate is at least 50% (e.g., at least e.g., at least 100%, at least 200% or at least 400%) higher when administered to the mammal at the higher of the two glucose concentrations (e.g., 300 vs. 100 mg/dL glucose).

In certain embodiments, the serum elimination rate of the conjugate is slower when administered to the mammal at the higher of the two glucose concentrations (e.g., 300 vs. 100 mg/dL glucose). In certain embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

As discussed in the Examples, we have found that in certain embodiments the serum concentration curve of conjugates can be fit using a two-compartment bi-exponential model with one short and one long half-life. The long half-life appears to be particularly sensitive to glucose concentration. Thus, in certain embodiments, the long half-life is longer when administered to the mammal at the higher of the two glucose concentrations (e.g., 300 vs. 100 mg/dL glucose). In certain embodiments, the long half-life is at least 50% (e.g., at least 100%, at least 200% or at least 400%) longer when administered to the mammal at the higher of the two glucose concentrations (e.g., 300 vs. 100 mg/dL glucose).

In certain embodiments, the serum concentration curve of a conjugate is substantially the same as the serum concentration curve of an unconjugated version of the insulin when administered to the mammal under hyperglycemic conditions. As used herein, the term "substantially the same" means that there is no statistical difference between the two curves as determined by a student t-test (p>0.05). In certain embodiments, the serum concentration curve of the conjugate is substantially different from the serum concentration curve of an unconjugated version of the insulin when administered under fasted conditions. In certain embodiments, the serum concentration curve of the conjugate is substantially the same as the serum concentration curve of an unconjugated version of the insulin when administered under hyperglycemic conditions and substantially different when administered under fasted conditions. In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). In certain embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of the conjugate may increase when the glucose concentration increases or when the glucose concentration crosses a threshold, e.g., is higher than normal glucose levels. In certain embodiments, the bioactivity of a conjugate is lower when administered under fasted conditions as compared to hyperglycemic conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.).

In certain embodiments, the PD properties of the conjugate may be tested by measuring the glucose infusion rate (GIR) required to maintain a steady glucose concentration. According to such embodiments, the bioactivity of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in certain embodiments, the bioactivity of the conjugate is higher when administered to the mammal at the higher of the two glucose concentrations (e.g., 300 vs. 100 mg/dL glucose). In certain embodiments, the bioactivity of the conjugate is at least 25% (e.g., at least 50% or at least 100%) higher when administered to the mammal at the higher of the two glucose concentrations (e.g., 300 vs. 100 mg/dL glucose).

In certain embodiments, the PD behavior for insulin can be observed by comparing the time to reach minimum blood glucose concentration ($T_{nadir}$), the duration over which the blood glucose level remains below a certain percentage of the initial value (e.g., 70% of initial value or $T_{70\% BGL}$), etc.

In general, it will be appreciated that any of the PK and PD characteristics discussed in this section can be determined according to any of a variety of published pharmacokinetic and pharmacodynamic methods (e.g., see Baudys et al., *Bioconjugate Chem.* 9:176-183, 1998 for methods suitable for subcutaneous delivery). It is also to be understood that the PK and/or PD properties may be measured in any mammal (e.g., a human, a rat, a cat, a minipig, a dog, etc.). In certain embodiments, PK and/or PD properties are measured in a human. In certain embodiments, PK and/or PD properties are measured in a rat. In certain embodiments, PK and/or PD properties are measured in a minipig. In certain embodiments, PK and/or PD properties are measured in a dog.

It will also be appreciated that while the foregoing was described in the context of glucose-responsive conjugates, the same properties and assays apply to conjugates that are responsive to other saccharides including exogenous saccharides, e.g., mannose, L-fucose, N-acetyl glucosamine, alpha-methyl mannose, etc. As discussed in more detail below and in the Examples, instead of comparing PK and/or PD properties under fasted and hyperglycemic conditions, the PK and/or PD properties may be compared under fasted conditions with and without administration of the exogenous saccharide. It is to be understood that conjugates can be designed that respond to different $C_{max}$ values of a given exogenous saccharide.

Ligand(s)

In general, provided crystalline insulin-conjugates include at least one ligand. In certain embodiments, the conjugates include a single ligand. In certain embodiments, the conjugates include at least two separate ligands, e.g., 2, 3, 4, 5 or more ligands. When more than one ligand is present the ligands may have the same or different chemical structures.

In certain embodiments, the ligands are capable of competing with a saccharide (e.g., glucose or mannose) for binding to an endogenous saccharide-binding molecule (e.g., without limitation surfactant proteins A and D or members of the selectin family). In certain embodiments, the ligands are capable of competing with a saccharide (e.g., glucose or mannose) for binding to cell-surface sugar receptor (e.g., without limitation macrophage mannose receptor, glucose transporter ligands, endothelial cell sugar receptors, or hepatocyte sugar receptors). In certain embodiments, the ligands are capable of competing with glucose for binding to an endogenous glucose-binding molecule (e.g., without limitation surfactant proteins A and D or members of the selectin family). In certain embodiments, the ligands are capable of competing with a saccharide for binding to a non-human lectin (e.g., Con A). In certain embodiments, the ligands are capable of competing with glucose or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, pisum sativum agglutinin (PSA), vicia faba lectin, lens culinaris lectin, soybean lectin, peanut lectin, lathyrus ochrus lectin, sainfoin lectin, sophora japonica lectin, bowringia milbraedii lectin, concanavalin A (Con A), and pokeweed mitogen.

In certain embodiments, the ligand is of formula (IVa) or (IVb):

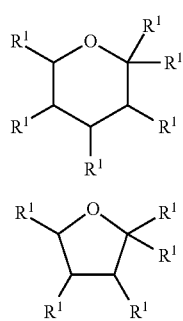

IVa

IVb wherein:
each $R^1$ is independently hydrogen, —$OR^y$, —$N(R^y)_2$, —$SR^y$, —O—Y, -G-Z, or —$CH_2R^x$;
each $R^x$ is independently hydrogen, —$OR^y$, —$N(R^y)_2$, —$SR^y$, or —O—Y;
each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by O, S, $N(R^2)$—, —C(O)—, —OC(O)—, —C(O)O—, —C(O)N(R^2)—, —N(R^2)C(O)—, —N(R^2)C(O)N(R^2)—, —$SO_2$—, —$SO_2N(R^2)$—, —$N(R^2)SO_2$—, or —$N(R^2)SO_2N(R^2)$—;
each Z is independently halogen, —$N(R^2)_2$, —$OR^2$, —$SR^2$, —$N_3$, —$CCR^2$, —$CO_2R^2$, —$C(O)R^2$, or —$OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the ligand of formula (IVa) or (IVb) is a monosaccharide. In certain embodiments, the ligand is a disaccharide. In certain embodiments, the ligand is a trisaccharide. In certain embodiments, the ligand is a tetrasaccharide. In certain embodiments, the ligand comprises no more than a total of four monosaccharide moieties.

As defined generally above, each $R^1$ is independently hydrogen, —$OR^y$, —$N(R^y)_2$, —$SR^y$, —O—Y, -G-Z, or —$CH_2R^x$. In certain embodiments, $R^1$ is hydrogen. In certain embodiments, $R^1$ is —OH. In other embodiments, $R^1$ is —NHC(O)$CH_3$. In certain embodiments, $R^1$ is —O—Y. In certain other embodiments, $R^1$ is -G-Z. In some embodiments, $R^1$ is —$CH_2OH$. In other embodiments, $R^1$ is —$CH_2$—O—Y. In yet other embodiments, $R^1$ is —$NH_2$. One of ordinary skill in the art will appreciate that each $R^1$ substituent in formula (IVa) or (IVb) may be of (R) or (S) stereochemistry.

As defined generally above, each $R^x$ is independently hydrogen, —$OR^y$, —$N(R^y)_2$, —$SR^y$, or —O—Y. In some embodiments, $R^x$ is hydrogen. In certain embodiments, $R^x$ is —OH. In other embodiments, $R^x$ is —O—Y.

As defined generally above, each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$. In some embodiments, $R^y$ is hydrogen. In other embodiments, $R^y$ is —$R^2$. In some embodiments, $R^y$ is —$C(O)R^2$. In certain embodiments, $R^y$ is acetyl. In other embodiments, $R^y$ is —$SO_2R^2$, —$S(O)R^2$, —$P(O)(OR^2)_2$, —$CO_2R^2$, or —$C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of —O—Y through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by —O—, —S—, —$N(R^2)$—, —C(O)—, —OC(O)—, —C(O)O—, —C(O)N(R^2)—, —N(R^2)C(O)—, —N(R^2)C(O)N(R^2)—, —$SO_2$—, —$SO_2N(R^2)$—, —$N(R^2)SO_2$—, or —$N(R^2)SO_2N(R^2)$—. In some embodiments, G is a covalent bond. In certain embodiments, G is —O—$C_{1-8}$ alkylene. In certain embodiments, G is —$OCH_2CH_2$—.

As defined generally above, each Z is independently halogen, —$N(R^2)_2$, —$OR^2$, —$SR^2$, —$N_3$, —$CCR^2$, —$CO_2R^2$, —$C(O)R^2$, or —$OSO_2R^2$. In some embodiments, Z is a halogen or —$OSO_2R^2$. In other embodiments, Z is —$N_3$ or —$C\equiv CR^2$. In certain embodiments, Z is —$N(R^2)_2$, —$OR^2$, or —SR². In certain embodiments, Z is —SH. In certain embodiments, Z is —NH₂. In certain embodiments, -G-Z is —OCH₂CH₂NH₂.

In some embodiments, the R¹ substituent on the C1 carbon of formula (IVa) is -G-Z to give a compound of formula (IVa-i):

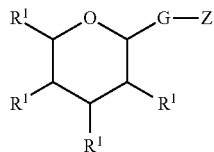

IVa-i wherein R¹, G, and Z are as defined and described herein.

In some embodiments, the ligand is of formula (IVa-ii):

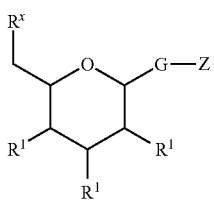

IVa-ii wherein R¹, R$^x$, G, and Z are as defined and described herein.

In certain embodiments, the ligand(s) may have the same chemical structure as glucose or may be a chemically related species of glucose. In various embodiments it may be advantageous for the ligand(s) to have a different chemical structure from glucose, e.g., in order to fine tune the glucose response of the conjugate. For example, in certain embodiments, one might use a ligand that includes glucose, mannose, L-fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In certain embodiments, the ligand includes a monosaccharide. In certain embodiments, the ligand includes a disaccharide. In certain embodiments, the ligand is includes a trisaccharide. In some embodiments, the ligand comprises a saccharide and one or more amine groups. In certain embodiments the saccharide and amine group are separated by a C₁-C₆ alkyl group, e.g., a C₁-C₃ alkyl group. In some embodiments, the ligand is aminoethylglucose (AEG). In some embodiments, the ligand is aminoethylmannose (AEM). In some embodiments, the ligand is aminoethylbimannose (AEBM). In some embodiments, the ligand is aminoethyltrimannose (AETM). In some embodiments, the ligand is β-aminoethyl-N-acetylglucosamine (AEGA). In some embodiments, the ligand is aminoethylfucose (AEF). In certain embodiments, a saccharide ligand is of the "D" configuration. In other embodiments, a saccharide ligand is of the "L" configuration. Below we show the structures of these exemplary ligands. Other exemplary ligands will be recognized by those skilled in the art.

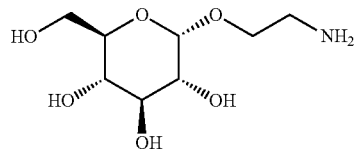

AEG

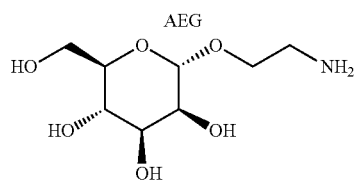

AEM

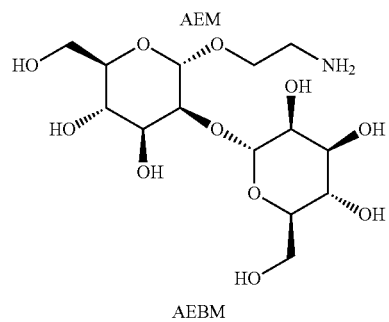

AEBM

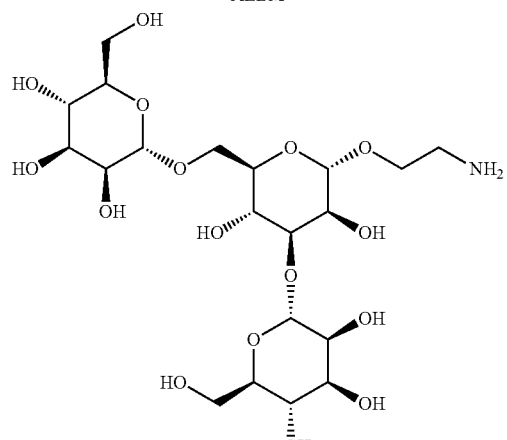

AETM

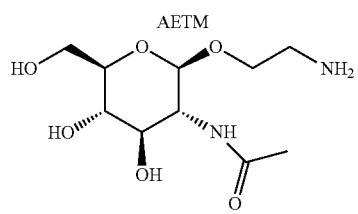

AEGA

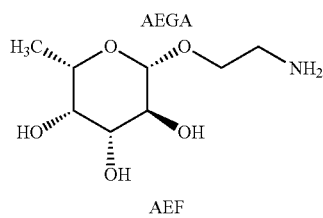

AEF

In general, ligands may be directly or indirectly conjugated (i.e., via a linker or framework) to the insulin molecule. As discussed in more detail below, the ligands may be naturally present within a conjugate framework (e.g., as part of a polymer backbone or as a side group of a monomer). Alternatively (or additionally) ligands may be artificially incorporated into a conjugate framework (e.g., in the form of a chemical group that is synthetically added to a conjugate framework). In certain embodiments, a conjugate may include a framework which comprises 5 or more, 10 or more, or 20 or more ligands. In certain embodiments, a conjugate may comprise as few as 1, 2, 3, 4 or 5 separate ligands.

In certain embodiments, at least two separate ligands are conjugated to the insulin molecule via different conjugation points. In certain embodiments, at least two separate ligands are conjugated to a single conjugate framework that is also conjugated to the insulin molecule. In some embodiments, at least one ligand, such as AETM, AEG, AEM, AEBM, AEGA, or AEF, is conjugated to one insulin molecule. In certain embodiments, at least one AETM ligand is conjugated to one insulin molecule. In some embodiments, at least two ligands, such as AETM, AEG, AEM, AEBM, AEGA, or AEF, are conjugated to one insulin molecule, either through one conjugation point or multiple conjugation points. In certain embodiments, the at least two ligands are not the same ligand. In certain embodiments, the at least two ligands are the same ligand. In certain embodiments, at least two AETM ligands are conjugated to one insulin molecule, either through one conjugation point or multiple conjugation points.

In certain embodiments, the saccharide within the one or more ligands is conjugated (directly or indirectly by way of a linker) via the C1, C2 or C6 position. In certain embodiments, the conjugation involves the C1 position. The C1 position of a saccharide is also referred to as the anomeric carbon and may be connected to the insulin molecule or conjugate framework in the alpha or beta conformation. In certain embodiments, the C1 position is configured as the alpha anomer. In other embodiments, the C1 position is configured as the beta anomer.

Insulin

As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, Pediatr. Emerg. Care. 23:903-905, 2007 and Gerich, Am. J. Med. 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids).

In certain embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In certain embodiments, an insulin molecule of the present disclosure will differ from a wild-type insulin by amino acid substitutions only. In certain embodiments, an insulin molecule of the present disclosure will differ from a wild-type insulin by amino acid additions only. In certain embodiments, an insulin molecule of the present disclosure will differ from a wild-type insulin by both amino acid substitutions and additions. In certain embodiments, an insulin molecule of the present disclosure will differ from a wild-type insulin by both amino acid substitutions and deletions.

In certain embodiments, amino acid substitutions may be made on the basis of similarity in polarity, charge, solubility, hydrophobicity, hydrophilicity, and/or the amphipathic nature of the residues involved. In certain embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In certain embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691, 198.

Figure 33:
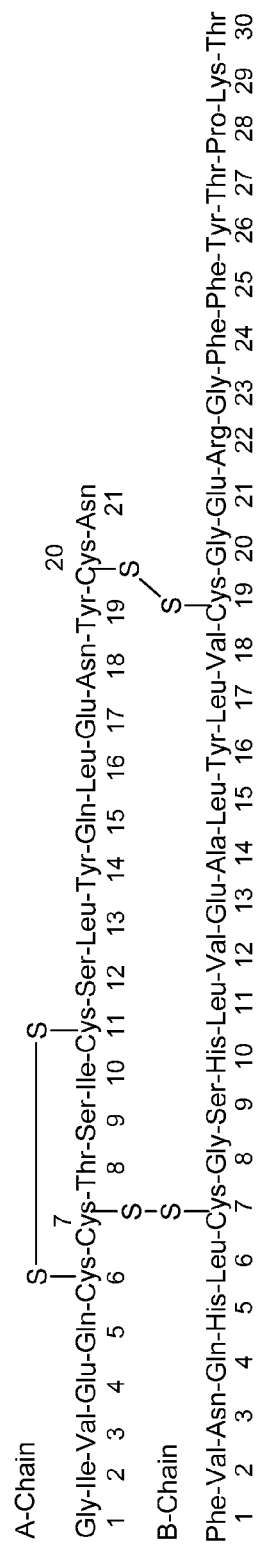
FIG. 33: Structure of wild-type human insulin.

The wild-type sequence of human insulin (A-chain and B-chain) is shown below and in FIG. 33.

```
A-Chain (SEQ ID NO: 1):
GIVEQCCTSICSLYQLENYCN

B-Chain (SEQ ID NO: 2):
FVNQHLCGSHLVEALYLVCGERGFFYTPKT
```

Human insulin differs from rabbit, porcine, bovine, and sheep insulin only in amino acids A8, A9, A10, and B30 (see table below).

| | Amino Acid Position | | | |
|---|---|---|---|---|
| Insulin | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B— peptide. Examples of such insulin polypeptides include $\text{Arg}^{A0}$-human insulin, $\text{Arg}^{B31}\text{Arg}_{B32}$-human insulin, $\text{Gly}^{A21}\text{Arg}^{B31}\text{Arg}^{B32}$-human insulin, $\text{Arg}^{A9}\text{Arg}^{B31}\text{Arg}^{B32}$-human insulin, and $\text{Arg}^{A0}\text{Gly}^{A21}\text{Arg}^{B31}\text{Arg}^{B32}$-human insulin. By way of further example, insulin glargine (LANTUS®) is an exemplary long acting insulin mutant in which $\text{Asp}^{A21}$ has been replaced by glycine, and two arginine residues have been added to the C-terminus of the B— peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $\text{Gly}^{A21}$-human insulin, $\text{Gly}^{A21}\text{Arg}^{B31}$-human insulin, $\text{Arg}^{B31}\text{Arg}^{B32}$-human insulin, $\text{Arg}^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des (B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $\text{Asn}^{A18}$, $\text{Asn}^{A21}$, or $\text{Asn}^{B3}$, or any combination of those residues, may be replaced by aspartic acid or glutamic acid. $\text{Gln}^{A15}$ or $\text{Gln}^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid ($\text{His}^{B10} \to \text{Asp}^{B10}$); replacement of the phenylalanine residue at position B1 with aspartic acid ($\text{Phe}^{B1} \to \text{Asp}^{B1}$); replacement of the threonine residue at position B30 with alanine)($\text{Thr}^{B30} \to \text{Ala}^{B30}$; replacement of the tyrosine residue at position B26 with alanine ($\text{Tyr}^{B26} \to \text{Ala}^{B26}$); and replacement of the serine residue at position B9 with aspartic acid ($\text{Ser}^{B9} \to \text{Asp}^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $\text{Thr}^{B30}$ has been deleted, and a C14 fatty acid chain (myristic acid) has been attached to $\text{Lys}^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

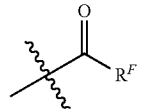

wherein $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of $\text{Lys}^{B28}$ is conjugated to the fatty acid moiety. In certain embodiments, position B3 of the insulin molecule is Lys and the epsilon-amino group of $\text{Lys}^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which $\text{Thr}^{B30}$ has been deleted, and a C14 fatty acid chain (myristic acid) is attached to $\text{Lys}^{B29}$.

In certain embodiments, an insulin molecule of the present disclosure comprises the mutations and/or chemical modifications of one of the following insulin molecules:

Lys$^{B28}$Pro$^{B29}$-human insulin (insulin lispro), Asp$^{B28}$-human insulin (insulin aspart), Lys$^{B3}$Glu$^{B29}$-human insulin (insulin glulisine), Arg$^{B31}$Arg$^{B32}$-human insulin (insulin glargine), N$^{\epsilon B29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: N$^{\epsilon B29}$-palmitoyl-human insulin, N'$^{\epsilon B29}$-myrisotyl-human insulin, N$^{\epsilon B28}$-palmitoyl-Lys$^{B28}$ProB29-human insulin, N$\epsilon^{B28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-palmitoyl-des(B30)-human insulin, N$^{\epsilon B30}$-myristoyl-Thr$^{B29}$Lys$^{B30}$-human insulin, N$^{\epsilon B29}$-palmitoyl-Thr$^{B29}$Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(ω-carboxyheptadecanoyl)-human insulin.

In certain embodiments, an insulin molecule of the present disclosure comprises the mutations and/or chemical modifications of one of the following insulin molecules: N$^{\epsilon B29}$-octanoyl-human insulin, N$^{\epsilon B29}$-myristoyl-Gly$^{A21}$Arg$^{B31}$Arg$^{B31}$-human insulin, N$^{\epsilon B29}$-myristoyl-Gly$^{A21}$Gln$^{B3}$Arg$^{B31}$Arg$^{B32}$-human insulin, N$^{\epsilon B29}$-myristoyl-Arg$^{A0}$Gly$^{A21}$Arg$^{B31}$Arg$^{\epsilon B32}$-human insulin, N$^{\epsilon B29}$-Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$^{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B31}$Arg$^{B32}$-human insulin, N$^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B1}$Arg$^{B}$32-human insulin.

In certain embodiments, an insulin molecule of the present disclosure comprises the mutations and/or chemical modifications of one of the following insulin molecules: N$^{\epsilon B29}$-tridecanoyl-des(B30)-human insulin, N$^{\epsilon B29}$-tetradecanoyl-des(B30)-human insulin, N$^{\epsilon B29}$-decanoyl-des(B30)-human insulin, N$^{\epsilon B29}$-dodecanoyl-des(B30)-human insulin, N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$-Gln$^{B3}$-des(B30)-human insulin, N$^{\epsilon B29}$-dodecanoyl-Gly$^{A21}$-Gln$^{B3}$-des(B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des(B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl-Ala$^{A21}$Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Glu$^{B30}$-human insulin, N$^{\epsilon B29}$-tetradecanoyl-Glu$^{B30}$-human insulin, N$^{\epsilon B29}$-decanoyl-Glu$^{B30}$-human insulin, N$^{\epsilon B29}$-dodecanoyl-Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Glu$^{B30}$-human insulin, N$^{\epsilon B29}$-tetradecanoyl-Gly$^{A21}$Glu$^{B30}$-human insulin, N$^{\epsilon B29}$-decanoyl-Gly$^{A21}$Glu$^{B30}$-human insulin, N$^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$Glu$^{B30}$-human insulin, N$^{\epsilon B29}$-tetradecanoyl-Gly$^{A21}$Gln$^{B3}$Glu$^{B30}$-human insulin, N$^{\epsilon B29}$-decanoyl-Gly$^{A21}$Gln$^{B3}$Glu$^{B30}$-human insulin, N$^{\epsilon B29}$-dodecanoyl-Gly$^{A21}$Gln$^{B3}$Glu$^{B30}$-human insulin, N$^{\epsilon B29}$-tridecanoyl-Ala$^{A21}$Glu$^{B30}$-human insulin, N$^{\epsilon B29}$-tetradecanoyl-Ala$^{A21}$Glu$^{B30}$-human insulin, N$^{\epsilon B29}$-decanoyl-Ala$^{A21}$Glu$^{B30}$-human insulin, N$^{\epsilon B29}$-dodecanoyl-Ala$^{A21}$Glu$^{B30}$-human insulin, N$^{\epsilon B29}$-tridecanoyl-Ala$^{A21}$Gln$^{B30}$-human insulin, N$^{\epsilon B29}$-tetradecanoyl-Ala$^{A21}$Gln$^{B3}$Glu$^{B30}$-human insulin, N$^{\epsilon B29}$-decanoyl-Ala$^{A21}$Gln$^{B3}$Glu$^{B30}$-human insulin, N$^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$Glu$^{B30}$-human insulin, N$^{\epsilon B29}$-tetradecanoyl-Gln$^{B3}$Glu$^{B30}$-human insulin, N$^{\epsilon B29}$-decanoyl-Gln$^{B3}$Glu$^{B30}$-human insulin, N$^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-formyl-human insulin, N$^{\alpha B1}$-formyl-human insulin, N$^{\alpha A1}$-formyl-human insulin, N$^{\epsilon B29}$-formyl-N$^{\alpha B1}$-formyl-human insulin, N$^{\epsilon B29}$-formyl-N$^{\alpha A1}$-formyl-human insulin, N$^{\alpha A1}$-formyl-N$^{\alpha B1}$-formyl-human insulin, N$^{\epsilon B29}$-formyl-N$^{\alpha A1}$-formyl-N$^{\alpha B1}$-formyl-human insulin.

In certain embodiments, an insulin molecule of the present disclosure comprises the mutations and/or chemical modifications of one of the following insulin molecules: N$^{\epsilon B29}$-acetyl-human insulin, N$^{\alpha B1}$-acetyl-human insulin, N$^{\alpha A1}$-acetyl-human insulin, N$^{\epsilon B29}$-acetyl-N$^{\alpha B1}$-acetyl-human insulin, N$^{\epsilon B29}$-acetyl-N$^{\alpha A1}$-acetyl-human insulin, N$^{\alpha A1}$-acetyl-N$^{\alpha B1}$-acetyl-human insulin, N$^{\epsilon B29}$-acetyl-N$^{\alpha A1}$-acetyl-N$^{\alpha B1}$-acetyl-human insulin.

In certain embodiments, an insulin molecule of the present disclosure comprises the mutations and/or chemical modifications of one of the following insulin molecules: N$^{\epsilon B29}$-propionyl-human insulin, N$^{\alpha B1}$-propionyl-human insulin, N$^{\alpha A1}$-propionyl-human insulin, N$^{\epsilon B29}$-acetyl-N$^{\alpha B1}$-propionyl-human insulin, N$^{\epsilon B29}$-propionyl-N$^{\alpha A1}$-propionyl-human insulin, N$^{\alpha A1}$-propionyl-N$^{\alpha B1}$-propionyl-human insulin, N$^{\epsilon B29}$-propionyl-N$^{\alpha A1}$-propionyl-N$^{\alpha B1}$-propionyl-human insulin.

In certain embodiments, an insulin molecule of the present disclosure comprises the mutations and/or chemical modifications of one of the following insulin molecules: N$^{\epsilon B29}$-butyryl-human insulin, N$^{\alpha B1}$-butyryl-human insulin, N$^{\alpha A1}$-butyryl-human insulin, N$^{\epsilon B29}$-butyryl-N$^{\alpha B1}$-butyryl-human insulin, N$^{\epsilon B29}$-butyryl-N$^{\alpha A1}$-butyryl-human insulin, N$^{\alpha A1}$-butyryl-N$^{\alpha B1}$-butyryl-human insulin, N$^{\epsilon B29}$-butyryl-N$^{\alpha A1}$-butyryl-N$^{\alpha B1}$-butyryl-human insulin.

In certain embodiments, an insulin molecule of the present disclosure comprises the mutations and/or chemical modifications of one of the following insulin molecules: N$^{\epsilon B29}$-pentanoyl-human insulin, N$^{\alpha B1}$-pentanoyl-human insulin, N$^{\alpha A1}$-pentanoyl-human insulin, N$^{\epsilon B29}$-pentanoyl-N$^{\alpha B1}$-pentanoyl-human insulin, N$^{\epsilon B29}$-pentanoyl-N$^{\alpha A1}$-pentanoyl-human insulin, N$^{\alpha A1}$-pentanoyl-N$^{\alpha B1}$-pentanoyl-human insulin, N$^{\epsilon B29}$-pentanoyl-N$^{\alpha A1}$-pentanoyl-N$^{\alpha B1}$-pentanoyl-human insulin.

In certain embodiments, an insulin molecule of the present disclosure comprises the mutations and/or chemical modifications of one of the following insulin molecules: N$^{\epsilon B29}$-hexanoyl-human insulin, N$^{\alpha B1}$-hexanoyl-human insulin, N$^{\alpha A1}$-hexanoyl-human insulin, N$^{\epsilon B29}$-hexanoyl-N$^{\alpha B1}$-hexanoyl-human insulin, N$^{\epsilon B29}$-hexanoyl-N$^{\alpha A1}$-hexanoyl-human insulin, N$^{\alpha A1}$-hexanoyl-N$^{\alpha B1}$-hexanoyl-human insulin, N$^{\epsilon B29}$-hexanoyl-N$^{\alpha A1}$-hexanoyl-N$^{\alpha B1}$-hexanoyl-human insulin.

In certain embodiments, an insulin molecule of the present disclosure comprises the mutations and/or chemical modifications of one of the following insulin molecules: N$^{\epsilon B29}$-heptanoyl-human insulin, N$^{\alpha B1}$-heptanoyl-human insulin, N$^{\alpha A1}$-heptanoyl-human insulin, N$^{\epsilon B29}$-heptanoyl-N$^{\alpha B1}$-human insulin, N$^{\epsilon B29}$-heptanoyl-N$^{\alpha A1}$-heptanoyl-human insulin, N$^{\alpha A1}$-heptanoyl-N$^{\alpha B1}$-heptanoyl-human insulin, N$^{\epsilon B29}$-heptanoyl-N$^{\alpha A1}$-heptanoyl-N$^{\alpha B1}$-heptanoyl-human insulin.

In certain embodiments, an insulin molecule of the present disclosure comprises the mutations and/or chemical modifications of one of the following insulin molecules: N$^{\alpha B1}$-octanoyl-human insulin, N$^{\alpha A1}$-octanoyl-human insulin, N$^{\epsilon B29}$-octanoyl-N$^{\alpha B1}$-octanoyl-human insulin, N$^{\epsilon B29}$-octanoyl-N$^{\alpha A1}$-octanoyl-human insulin, N$^{\alpha A1}$-octanoyl-N$^{\alpha B1}$-octanoyl-human insulin, N$^{\epsilon B29}$-octanoyl-N$^{\alpha A1}$-octanoyl-N$^{\alpha B1}$-octanoyl-human insulin.

In certain embodiments, an insulin molecule of the present disclosure comprises the mutations and/or chemical modifications of one of the following insulin molecules: N$^{\epsilon B29}$-nonanoyl-human insulin, N$^{\alpha B1}$-nonanoyl-human insulin, N$^{\alpha A1}$-nonanoyl-human insulin, N$^{\epsilon B29}$-nonanoyl-N$^{\alpha B1}$-nonanoyl-human insulin, N$^{\epsilon B29}$-nonanoyl-N$^{\alpha A1}$-nonanoyl-human insulin, N$^{\alpha A1}$-nonanoyl-N$^{\alpha B1}$-nonanoyl-human insulin, N$^{\epsilon B29}$-nonanoyl-N$^{\alpha A1}$-nonanoyl-N$^{\alpha B1}$-nonanoyl-human insulin.

In certain embodiments, an insulin molecule of the present disclosure comprises the mutations and/or chemical modifications of one of the following insulin molecules: N$^{\epsilon B29}$-decanoyl-human insulin, N$^{\alpha B1}$-decanoyl-human insulin, N$^{\alpha A1}$-decanoyl-human insulin, decanoyl-N$^{\alpha B1}$-decanoyl-human insulin, N$^{\epsilon B29}$-decanoyl-N$^{\alpha A1}$-decanoyl-human insulin, N$^{\alpha A1}$-decanoyl-N$^{\alpha B1}$-decanoyl-human insulin, N$^{\epsilon B29}$-decanoyl-N$^{\alpha A1}$-decanoyl-N$^{\alpha B1}$-decanoyl-human insulin.

In certain embodiments, an insulin molecule of the present disclosure comprises the mutations and/or chemical modifications of one of the following insulin molecules: N$^{\epsilon B28}$-formyl-Lys$^{B28}$Pro$^{B29}$-human insulin, N$^{\alpha B1}$-formyl-Lys$^{B28}$Pro$^{B29}$-human insulin, N$^{\alpha A1}$-formyl-Lys$^{B28}$Pro$^{B29}$-human insulin, N$^{\epsilon B28}$-formyl-N$^{\alpha B1}$-formyl-Lys$^{B28}$Pro$^{B29}$-human insulin, N$^{\epsilon B28}$-formyl-N$^{\alpha A1}$-formyl-Lys$^{B28}$Pro$^{B29}$-human insulin, N$^{\alpha A1}$-formyl-N$^{\alpha B1}$-formyl-Lys$^{B28}$Pro$^{B29}$-human insulin, N$^{\epsilon B28}$-formyl-N$^{\alpha A1}$-formyl-N$^{\alpha B1}$-formyl-Lys$^{B28}$Pro$^{B29}$-human insulin, N$^{\epsilon 29}$-acetyl-Lys$^{B28}$Pro$^{B29}$-human insulin, N$^{\alpha B1}$-acetyl-Lys$^{B28}$Pro$^{B29}$-human insulin, N$^{\alpha A1}$-acetyl-Lys$^{B28}$Pro$^{B29}$-human insulin, N$^{\epsilon B28}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-acetyl-N$^{\alpha A1}$-acetyl-Lys$^{B28}$Pro$^{B29}$-human insulin, N$^{\alpha A1}$-acetyl-N$^{\alpha B1}$-acetyl-Lys$^{B28}$Pro$^{B29}$-human insulin, N$^{\epsilon B28}$-acetyl-N$^{\alpha B1}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-propionyl-Lys$^{B28}$Pro$^{B29}$-human insulin, N$^{\alpha B1}$-propionyl-Lys$^{B28}$Pro$^{B29}$-human insulin, N$^{\alpha A1}$-propionyl-Lys$^{B28}$Pro$^{B29}$- human insulin, $N^{\epsilon B28}$-propionyl-$N^{\alpha B1}$-propionyl-Lys$^{B28}$Pro$^{B29}$-human insulin, $N^{\epsilon B28}$-propionyl-$N^{\alpha A1}$-propionyl-Lys$^{B28}$Pro$^{B29}$-human insulin, $N^{\alpha A1}$-propionyl-$N^{\alpha B1}$-propionyl-Lys$^{B28}$Pro$^{B29}$-human insulin, $N^{\epsilon B28}$-propionyl-$N^{\alpha A1}$-propionyl-$N^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-butyryl-Lys$^{B28}$Pro$^{B29}$-human insulin, $N^{\alpha B1}$-butyryl-Lys$^{B28}$Pro$^{B29}$-human insulin, $N^{\alpha A1}$-butyryl-Lys$^{B28}$Pro$^{B29}$-human insulin, $N^{\epsilon B28}$-butyryl-$N^{\alpha B1}$-butyryl-Lys$^{B28}$Pro$^{B29}$-human insulin, $N^{\epsilon B28}$-butyryl-$N^{\alpha A1}$-butyryl-Lys$^{B28}$Pro$^{B29}$-human insulin, $N^{\alpha A1}$-butyryl-$N^{\alpha B1}$-butyryl-Lys$^{B28}$Pro$^{B29}$-human insulin, $N^{\epsilon B28}$-butyryl-$N^{\alpha A1}$-butyryl-$N^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-pentanoyl-Lys$^{B28}$Pro$^{B29}$-human insulin, $N^{\alpha B1}$-pentanoyl-Lys$^{B28}$Pro$^{B29}$-human insulin, $N^{\alpha A1}$-pentanoyl-Lys$^{B28}$Pro$^{B29}$-human insulin, $N^{\epsilon B28}$, $N^{\alpha B1}$-pentanoyl-Lys$^{B28}$Pro$^{B29}$-human insulin, $N^{\epsilon B28}$-pentanoyl-$N^{\alpha A1}$-pentanoyl-Lys$^{B28}$Pro$^{B29}$-human insulin, $N^{\alpha A1}$-pentanoyl-$N^{\alpha B1}$-pentanoyl-Lys$^{B28}$Pro$^{B29}$-human insulin, $N^{\epsilon B28}$-pentanoyl-$N^{\alpha A1}$-pentanoyl-$N^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-hexanoyl-Lys$^{B28}$Pro$^{B29}$-human insulin, $N^{\alpha B1}$-hexanoyl-Lys$^{B28}$Pro$^{B29}$-human insulin, $N^{\alpha A1}$-hexanoyl-Lys$^{B28}$Pro$^{B29}$-human insulin, $N^{\epsilon B28}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-Lys$^{B28}$Pro$^{B29}$-human insulin, $N^{\alpha A1}$-hexanoyl-$N^{\alpha B1}$-hexanoyl-Lys$^{B28}$Pro$^{B29}$-human insulin, $N^{\epsilon B28}$-hexanoyl-$N^{\alpha A1}$-hexanoyl-$N^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-heptanoyl-Lys$^{B28}$Pro$^{B29}$-human insulin, $N^{\alpha B1}$-heptanoyl-Lys$^{B28}$Pro$^{B29}$-human insulin, $N^{\alpha A1}$-heptanoyl-Lys$^{B28}$Pro$^{B29}$-human insulin, $N^{\epsilon B28}$-heptanoyl-$N^{\alpha B1}$-Lys$^{B28}$Pro$^{B29}$-human insulin, $N^{\epsilon B28}$-heptanoyl-$N^{\alpha A1}$-heptanoyl-Lys$^{B28}$Pro$^{B29}$-human insulin, $N^{\alpha A1}$-heptanoyl-$N^{\alpha B1}$-heptanoyl-Lys$^{B28}$Pro$^{B29}$-human insulin, $N^{\epsilon B28}$-heptanoyl-$N^{\alpha A1}$-heptanoyl-$N^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-octanoyl-Lys$^{B28}$Pro$^{B29}$-human insulin, $N^{\alpha B1}$-octanoyl-Lys$^{B28}$ProB29-human insulin, $N^{\alpha A1}$-octanoyl-Lys$^{B28}$Pro$^{B29}$-human insulin, $N^{\epsilon B28}$-Octanoyl-$N^{\alpha B1}$-octanoyl-Lys$^{B28}$Pro$^{B29}$-human insulin, $N^{\epsilon B28}$-octanoyl-$N^{\alpha A1}$-octanoyl-Lys$^{B28}$Pro$^{B29}$-human insulin, $N^{\alpha A1}$-octanoyl-$N^{\alpha B1}$-octanoyl-Lys$^{B28}$Pro$^{B29}$-human insulin, $N^{\epsilon 28}$-Octanoyl-$N^{\alpha A1}$-octanoyl-$N^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-nonanoyl-Lys$^{B28}$Pro$^{B29}$-human insulin, $N^{\alpha B1}$-nonanoyl-Lys$^{B28}$Pro$^{B29}$-human insulin, $N^{\alpha A1}$-nonanoyl-Lys$^{B28}$Pro$^{B29}$-human insulin, $N^{\epsilon B28}$-nonanoyl-$N^{\epsilon 1B1}$-nonanoyl-Lys$^{B28}$Pro$^{B29}$-human insulin, $N^{\epsilon B28}$-nonanoyl-$N^{\alpha A1}$-nonanoyl-Lys$^{B28}$Pro$^{B29}$-human insulin, $N^{\alpha A1}$-nonanoyl-$N^{\alpha B1}$-nonanoyl-Lys$^{B28}$Pro$^{B29}$-human insulin, $N^{\epsilon B28}$-nonanoyl-$N^{\epsilon A1}$-nonanoyl-$N^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B28}$-decanoyl-Lys$^{B28}$Pro$^{B29}$-human insulin, $N^{\alpha B1}$-decanoyl-Lys$^{B28}$Pro$^{B29}$-human insulin, $N^{\alpha A1}$-decanoyl-Lys$^{B28}$Pro$^{B29}$-human insulin, $N^{\epsilon B28}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-Lys$^{"28}$Pro$^{B29}$-human insulin, $N^{\alpha A1}$-decanoyl-$N^{\alpha B1}$-decanoyl-Lys$^{B28}$Pro$^{B29}$-human insulin, $N^{\epsilon B28}$-decanoyl-$N^{\alpha A1}$-decanoyl-$N^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: $N^{\epsilon B29}$-pentanoyl-Gly$^{A21}$Arg$^{B31}$Arg$^{B32}$-human insulin, $N^{\alpha B1}$-hexanoyl-Gly$^{A21}$Arg$^{B31}$Arg$^{B32}$-human insulin, $N^{\alpha A1}$-heptanoyl-Gly$^{A21}$Arg$^{B31}$Arg$^{B32}$-human insulin, $N^{\epsilon B29}$-octanoyl-$N^{\alpha B1}$-octanoyl-Gly$^{A21}$Arg$^{B31}$Arg$^{B32}$-human insulin, $N^{\epsilon B29}$-propionyl-$N^{\alpha A1}$-propionyl-Gly$^{A21}$Arg$^{B31}$Arg$^{B32}$-human insulin, $N^{\alpha A1}$-acetyl-$N^{\alpha B1}$-acetyl-Gly$^{A21}$Arg$^{B31}$Arg$^{B32}$-human insulin, $N^{\epsilon B29}$-formyl-$N^{\alpha A1}$-formyl-$N^{\alpha B1}$-formyl-Gly$^{A21}$Arg$^{B31}$Arg$^{B32}$-human insulin, $N^{\epsilon B29}$-formyl-des(B26)-human insulin, $N^{\alpha B1}$-acetyl-Asp$^{B28}$-human insulin, $N^{\epsilon B29}$-propionyl-$N^{\alpha A1}$-propionyl-$N^{\alpha B1}$-propionyl-Asp$^{B1}$Asp$^{B3}$AspB$^{21}$-human insulin, $N^{\epsilon B29}$-pentanoyl-Gly$^{A21}$-human insulin, $N^{\alpha B1}$-hexanoyl-Gly$^{A21}$-human insulin, $N^{\alpha A1}$-heptanoyl-Gly$^{A21}$-human insulin, $N^{\epsilon B29}$-octanoyl-$N^{\alpha B1}$-octanoyl-Gly$^{A21}$-human insulin, $N^{\epsilon B29}$-propionyl-$N^{\alpha A1}$-propionyl-Gly$^{A21}$-human insulin, $N^{\alpha A1}$-acetyl-$N^{\alpha B1}$-acetyl-Gly$^{A21}$-human insulin, $N^{\epsilon B29}$-formyl-$N^{\alpha A1}$-formyl-$N^{\alpha B1}$-formyl-Gly$^{A21}$-human insulin, $N^{\epsilon B29}$-butyryl-des(B30)-human insulin, $N^{\alpha B1}$-butyryl-des(B30)-human insulin, $N^{\alpha A1}$-butyryl-des(B30)-human insulin, $N^{\epsilon B29}$-butyryl-$N^{\alpha B1}$-butyryl-des(B30)-human insulin, $N^{\epsilon B29}$-butyryl-$N^{\alpha A1}$-butyryl-des(B30)-human insulin, $N^{\alpha A1}$-butyryl-$N^{\alpha B1}$-butyryl-des(B30)-human insulin, $N^{\epsilon B29}$-butyryl-$N^{\alpha A1}$-butyryl-$N^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

In some embodiments, an insulin molecule is modified and/or mutated to reduce its affinity for the insulin receptor. Without wishing to be bound to a particular theory, it is believed that attenuating the receptor affinity of an insulin molecule through modification (e.g., acylation) or mutation may decrease the rate at which the insulin molecule is eliminated from serum. In some embodiments, a decreased insulin receptor affinity in vitro translates into a superior in vivo activity for an insulin-conjugate. In certain embodiments, an insulin molecule is mutated such that the site of mutation is used as a conjugation point, and conjugation at the mutated site reduces binding to the insulin receptor (e.g., $Lys^{A3}$). In certain other embodiments, conjugation at an existing wild-type amino acid or terminus reduces binding to the insulin receptor (e.g., $Gly^{A1}$). In some embodiments, an insulin molecule is conjugated at position A4, A5, A8, A9, or B30. In certain embodiments, the conjugation at position A4, A5, A8, A9, or B30 takes place via a wild-type amino acid side chain (e.g., $Glu^{A4}$). In certain other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

Methods for conjugating insulin molecules are described below. In certain embodiments, an insulin molecule is conjugated to a ligand or conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue.

Exemplary Insulin-Conjugates

In various embodiments, a crystalline insulin-conjugate of the present disclosure comprises an insulin molecule conjugated to one or more ligands that are independently selected from the group consisting of aminoethylglucose (AEG), aminoethylmannose (AEM), aminoethylbimannose (AEBM), aminoethyltrimannose (AETM), p-aminoethyl-N-acetylglucosamine (AEGA), and aminoethylfucose (AEF). In certain embodiments, the insulin molecule is conjugated via the epsilon-amino group of $Lys^{B29}$.

In certain embodiments, a crystalline insulin-conjugate of the present disclosure comprises an insulin molecule conjugated to one or more aminoethylglucose (AEG) ligands. In certain embodiments, a crystalline insulin-conjugate of the present disclosure comprises an insulin molecule conjugated to one or more aminoethylmannose (AEM) ligands. In certain embodiments, a crystalline insulin-conjugate of the present disclosure comprises an insulin molecule conjugated to one or more aminoethylbimannose (AEBM) ligands. In certain embodiments, a crystalline insulin-conjugate of the present disclosure comprises an insulin molecule conjugated to one or more aminoethyltrimannose (AETM) ligands. In certain embodiments, a crystalline insulin-conjugate of the present disclosure comprises an insulin molecule conjugated to one or more β-aminoethyl-N-acetylglucosamine (AEGA) ligands. In certain embodiments, a crystalline insulin-conjugate of the present disclosure comprises an insulin molecule conjugated to one or more aminoethylfucose (AEF) ligands.

In various embodiments, a crystalline insulin-conjugate of the present disclosure comprises an insulin molecule conjugated to two or more separate ligands. In some embodiments, a crystalline insulin-conjugate of the present disclosure comprises an insulin molecule conjugated to two separate ligands. In other embodiments, a crystalline insulin-conjugate of the present disclosure comprises an insulin molecule conjugated to three separate ligands. In certain embodiments, the two or more separate ligands of such a crystalline insulin-conjugate are aminoethylglucose (AEG). In certain embodiments, the two or more separate ligands of such a crystalline insulin-conjugate are aminoethylmannose (AEM). In certain embodiments, the two or more separate ligands of such a crystalline insulin-conjugate are aminoethylbimannose (AEBM). In certain embodiments, the two or more separate ligands of such a crystalline insulin-conjugate are aminoethyltrimannose (AETM). In certain embodiments, the two or more separate ligands of such a crystalline insulin-conjugate are β-aminoethyl-N-acetylglucosamine (AEGA). In certain embodiments, the two or more separate ligands of such a crystalline insulin-conjugate are aminoethylfucose (AEF).

In various embodiments, a crystalline insulin-conjugate of the present disclosure comprises two or more separate ligands are conjugated to a single conjugate framework that is also conjugated to an insulin molecule. In some embodiments, the two or more separate ligands and insulin molecule of such a crystalline insulin-conjugate are each located on a separate branch of a single branched conjugate framework. In some embodiments, the two or more separate ligands and insulin molecule of such a crystalline insulin-conjugate are each located on termini of separate branches of a single branched conjugate framework.

In various embodiments, a crystalline insulin-conjugate of the present disclosure comprises an insulin molecule conjugated to aminoethylglucose (AEG). In certain embodiments, a crystalline insulin-conjugate of the present disclosure comprises an insulin molecule conjugated to aminoethylglucose (AEG) via the epsilon-amino group of $Lys^{B29}$.

In various embodiments, a crystalline insulin-conjugate of the present disclosure comprises an insulin molecule conjugated to aminoethylmannose (AEM). In certain embodiments, a crystalline insulin-conjugate of the present disclosure comprises an insulin molecule conjugated to aminoethylmannose (AEM) via the epsilon-amino group of $Lys^{B29}$.

In various embodiments, a crystalline insulin-conjugate of the present disclosure comprises an insulin molecule conjugated to aminoethylbimannose (AEBM). In certain embodiments, a crystalline insulin-conjugate of the present disclosure comprises an insulin molecule conjugated to aminoethylbimannose (AEBM) via the epsilon-amino group of $Lys^{B29}$.

In various embodiments, a crystalline insulin-conjugate of the present disclosure comprises an insulin molecule conjugated to aminoethyltrimannose (AETM). In certain embodiments, a crystalline insulin-conjugate of the present disclosure comprises an insulin molecule conjugated to aminoethyltrimannose (AETM) via the epsilon-amino group of $Lys^{B29}$.

In various embodiments, a crystalline insulin-conjugate of the present disclosure comprises an insulin molecule conjugated to β-aminoethyl-N-acetylglucosamine (AEGA). In certain embodiments, a crystalline insulin-conjugate of the present disclosure comprises an insulin molecule conjugated to β-aminoethyl-N-acetylglucosamine (AEGA) via the epsilon-amino group of $Lys^{B29}$.

In various embodiments, a crystalline insulin-conjugate of the present disclosure comprises an insulin molecule conjugated to aminoethylfucose (AEF). In certain embodiments, a crystalline insulin-conjugate of the present disclosure comprises an insulin molecule conjugated to aminoethylfucose (AEF) via the epsilon-amino group of $Lys^{B29}$.

Conjugate Frameworks

This section describes some exemplary conjugate frameworks. In various embodiments, a conjugate of the present disclosure may have the general formula (I):

$$\left[ \left[ \left( \begin{array}{c} (B)_v \\ \boxed{A} \end{array} - T \right)_m \right]_n \boxed{A} - T \right]_p \right]_k \boxed{A} \quad D \tag{I}$$

wherein:

each occurrence of $\boxed{A}-T$ represents a potential branch within the conjugate;

each occurrence of $\boxed{A}-T$ represents a potential repeat within a branch of the conjugate;

each occurrence of $\boxed{A}$ is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently a ligand that includes a saccharide;

each occurrence of $L^B$ is independently a covalent bond or a group derived from the covalent conjugation of a T with an X;

-D is -T-$L^D$-$W^I$;

$W^I$ is an insulin molecule;

each occurrence of $L^D$ is independently a covalent bond or a group derived from the covalent conjugation of a T with a $W^I$;

k is an integer from 1 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

It is to be understood that general formula (I) (and other formulas herein) does not expressly list every hydrogen. For example, if the central $\boxed{A}$ is a $C_6$ aryl group and k<5 it will be appreciated that the open position(s) on the $C_6$ aryl ring include a hydrogen.

In general, it will be appreciated that each occurrence of $\boxed{A}$ represents a potential branching node and that the number of branches at each node are determined by the values of k for the central $\boxed{A}$ and n for non-central occurrences of $\boxed{A}$. One of ordinary skill will appreciate that because each occurrence of n may be an integer from 0 to 5, the present disclosure contemplates linear, branched, and hyperbranched (e.g., dendrimer-like) embodiments of these conjugates. The proviso which requires that within each k-branch at least one occurrence of n is ≥1 and at least one occurrence of v is ≥1 ensures that every conjugate includes at least one occurrence of B (i.e., a ligand).

In certain embodiments, each occurrence of $\boxed{A}$ in a p-bracketed moiety is substituted by a number of n-bracketed moieties corresponding to a value of n≥1. For example, when k=2 and p=2 in both k-branches, the conjugate may be of the formula (Ia):

$$\text{(Ia)}$$

In other embodiments, only terminal occurrences of $\boxed{A}$ in a p-bracketed moiety are substituted by a number of n-bracketed moieties corresponding to a value of n≥1. For example, when k=2 and p=2 in both k-branches (and n=0 for the first p-bracketed moiety in both k-branches), the conjugate may be of the formula (Ib):

$$\text{(Ib)}$$

In certain embodiments, each occurrence of $\boxed{A}$ in an m-bracketed moiety is substituted by a number of $\boxed{A}$ moieties corresponding to the value of v≥1. For example, when k=2, each occurrence of p=1, and each occurrence of m=2, the conjugate may be of the formula (Ic):

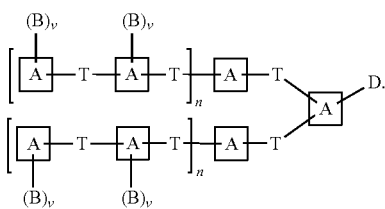

Ic

In other embodiments, only terminal occurrences of [A] in an m-bracketed moiety are substituted by a number of B moieties corresponding to a value of v≥1. For example, when k=2, each occurrence of p=1, and each occurrence of m=2 (and v=0 for the first m-bracketed moiety in each n-branch), the conjugate may be of the formula (Id):

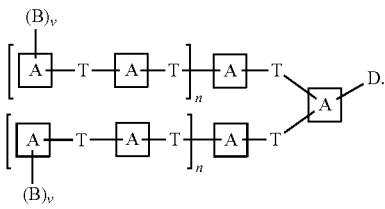

Id

By way of further example, when n=1 in both k-branches of the previous formula, the conjugate may be of the formula (Ie):

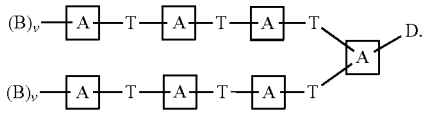

Ie

Alternatively, when n=2 in both k-branches of the previous formula, the conjugate may be of the formula (If):

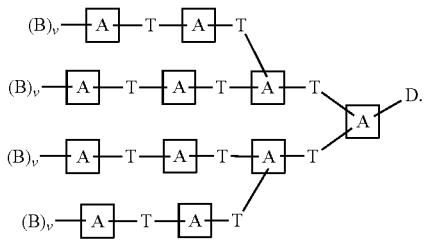

If

Description of Exemplary Groups

[A] (Node)

In certain embodiments, each occurrence of [A] is an optionally substituted group selected from the group consisting of acyl, aliphatic, heteroaliphatic, aryl, heteroaryl, and heterocyclic. In some embodiments, each occurrence of [A] is the same. In some embodiments, the central [A] is different from all other occurrences of [A]. In certain embodiments, all occurrences of [A] are the same except for the central [A].

In some embodiments, [A] is an optionally substituted aryl or heteroaryl group. In some embodiments, [A] is 6-membered aryl. In certain embodiments, [A] is phenyl.

In certain embodiments, [A] is a heteroatom selected from N, O, or S. In some embodiments, [A] is nitrogen atom. In some embodiments, [A] is an oxygen atom. In some embodiments, [A] is sulfur atom. In some embodiments, [A] is a carbon atom.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$, —N(R)SO$_2$, —SO$_2$N(R)—, a heterocyclic group, an aryl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$, —N(R)SO$_2$, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is

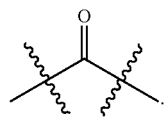 [SMILES: *C(*)=O]

In some embodiments, T is

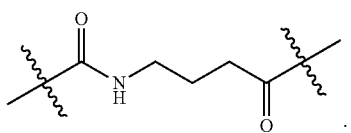 [SMILES: *C(=O)CCCNC(*)=O]

In some embodiments, T is

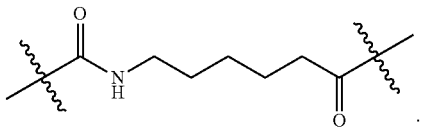 [SMILES: *C(=O)CCCCCNC(*)=O]

In some embodiments, T is

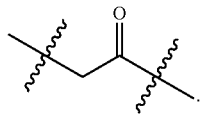

In some embodiments, T is

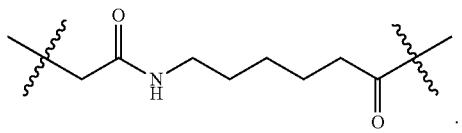 [SMILES: *CC(=O)NCCCCCC(*)=O]

In some embodiments, T is

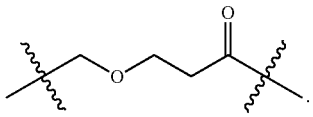 [SMILES: *COCCC(*)=O]

In certain embodiments, each occurrence of T is the same.

In certain embodiments, each occurrence of T (outside groups B and D) is a covalent bond and the conjugate is of the general formula (II):

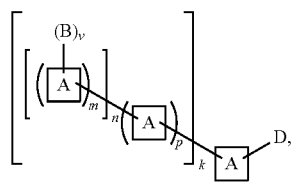

II wherein $\boxed{A}$, B, D, v, m, n, p, k, and j are as defined and described herein.

In certain embodiments of general formula (II), each occurrence of $\boxed{A}$ except for the central $\boxed{A}$ is a covalent bond, each occurrence of v=1, and the conjugate is of the formula (III):

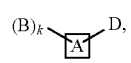

III wherein $\boxed{A}$, B, D, q, k, and j are as defined and described herein.

In certain such embodiments for formula (III), k=1.
In other embodiments, k=2.
In other embodiments, k=3.
In some embodiments, the present disclosure provides conjugates of general formula

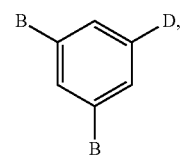

IIIa wherein B and D are as defined and described herein.

For example, in some embodiments, the present disclosure provides conjugates of formula:

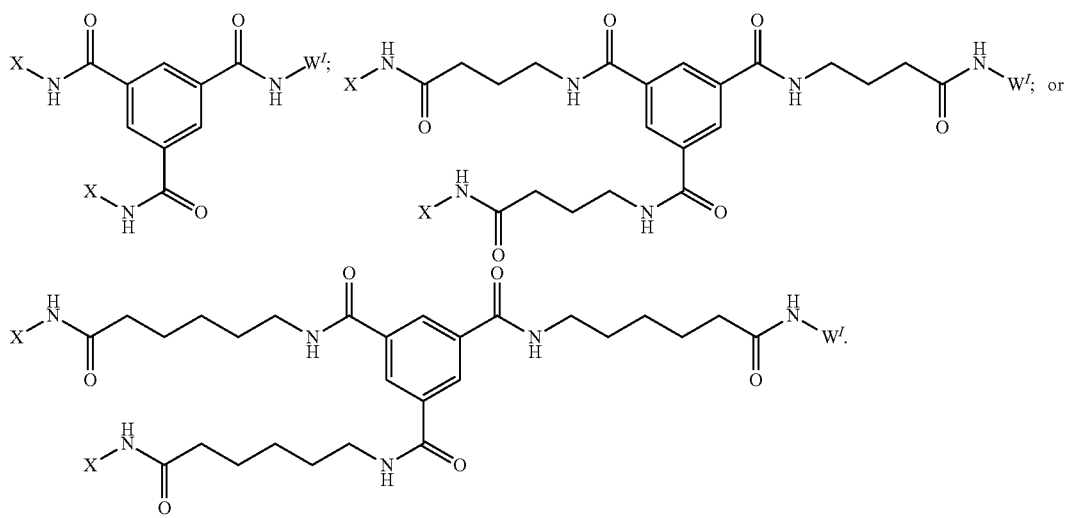

wherein $W^I$ and X are as defined and described herein.

In some embodiments, the present disclosure provides conjugates of general formula (IIIb):
wherein B and D are as defined and described herein.
For example, in some embodiments, the present disclosure provides conjugates of formula:
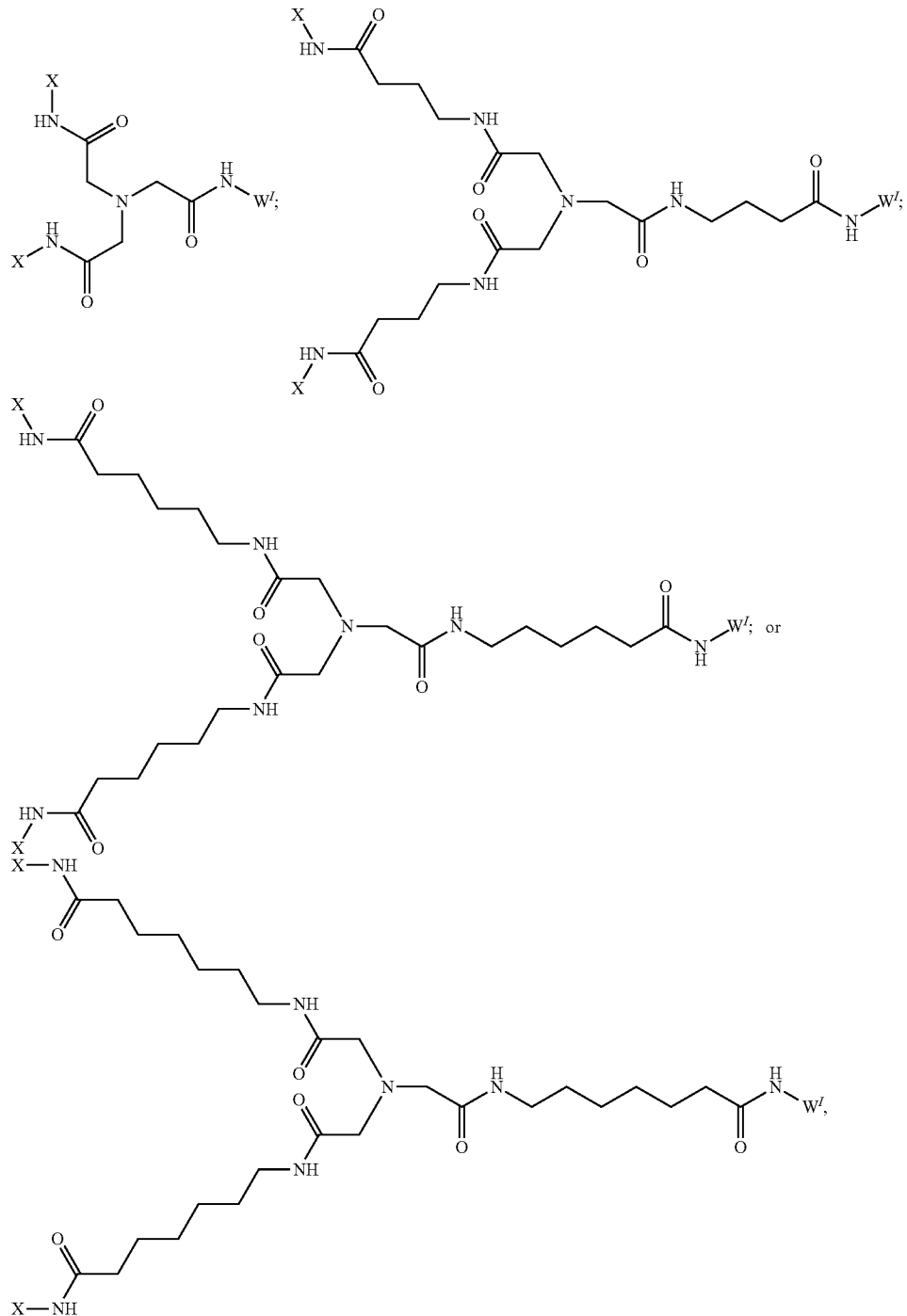
wherein $W^I$ and X are as defined and described herein.

For example, in some embodiments, the present disclosure provides conjugates of formula:

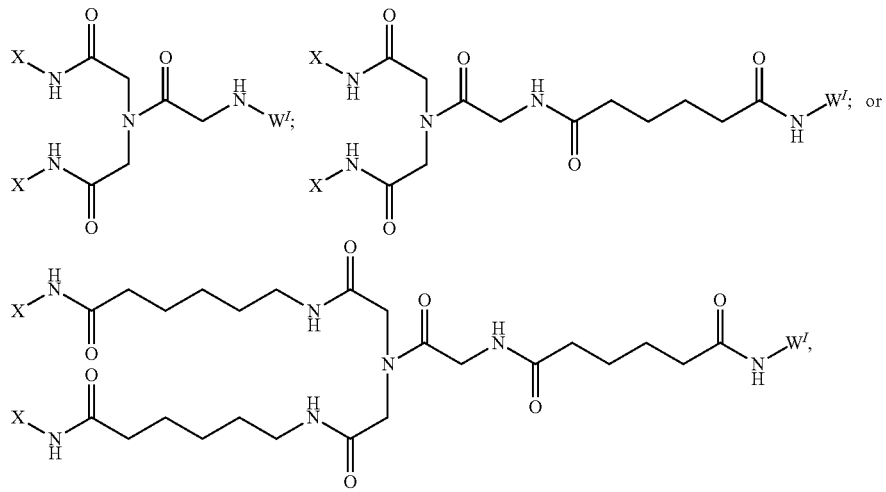

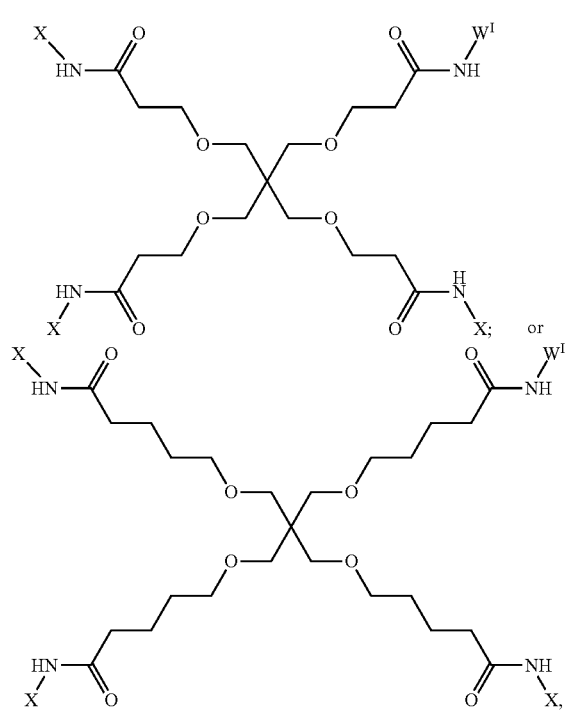

wherein $W^I$ and X are as defined and described herein.

In some embodiments, the present disclosure provides conjugates of general formula (IIIc):

 IIIc wherein B and D are as defined and described herein.

For example, in some embodiments, the present disclosure provides conjugates of formula:

wherein $W^I$ and X are as defined and described herein.

In some embodiments, the present disclosure provides conjugates of general formula (IIId) and (IIIe):

 IIId and

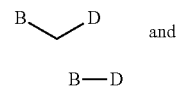 IIIe wherein B and D are as defined and described herein.

For example, in some embodiments, the present disclosure provides conjugates of formula:

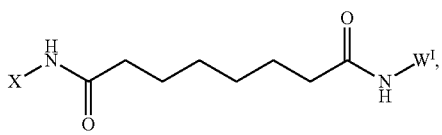

wherein $W^I$ and X are as defined and described herein.

B (Ligand)

—B is -T-$L^B$-X where X is a ligand that includes a saccharide; and $L^B$ is a covalent bond or a group derived from the covalent conjugation of an X with a T. Exemplary ligands and their saccharide components are described herein.

D (Insulin)

-D is -T-$L^D$-$W^I$ where $W^I$ is an insulin molecule and $L^D$ is a covalent bond or a group derived from the covalent conjugation of a $W^I$ with a T. Exemplary insulin molecules are described herein.

$L^B$ and $L^D$ (Covalent Conjugation)

One of ordinary skill will appreciate that a variety of conjugation chemistries may be used to covalently conjugate an X with a T and/or a $W^I$ with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or $W^I$. In some embodiments, L is an optionally substituted moiety derived from conjugating an optionally substituted carboxyl-reactive, thiol-reactive, amine-reactive, or hydroxyl-reactive moiety of X or $W^I$ with a carboxyl, thiol, amine, or hydroxyl group of T. In some embodiments, L is

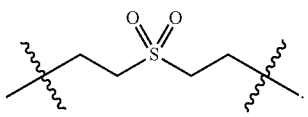

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below.

In various embodiments, carboxyl (or reactive ester) bearing components can be conjugated to —OH bearing frameworks (OBFs) using the procedure outlined by Kim et al., *Biomaterials* 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —$NH_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in *Bioconjugate Techniques*, $2^{nd}$ edition, Academic Press, 2008 and references cited therein). Briefly, a CBF with terminal activated carboxylic acid esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see see Hermanson in *Bioconjugate Techniques*, $2^{nd}$ edition, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques*, $2^{nd}$ edition, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine.

In various embodiments, azide bearing components can be coupled to an alkyne bearing framework (ABF) using the copper(I)-catalyzed modern version of the Huisgen-type azide-alkyne cycloaddition to give a 1,4-di-substituted 1,2,3- triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THF using N,N-diisopropylethylamine and Cu(PPh$_3$)$_3$Br as the catalyst system (e.g., see Wu et al., *Chem. Commun.* 5775-5777, 2005). The reaction may also be carried out in a 3:1 (THF:water) mixture using sodium ascorbate and CuSO$_4$.5H$_2$O as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., D. *Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF are added slowly and the solution allowed to mix for 30-60 minutes. After reaction, the crude solution is poured in an excess of acetone followed by dropwise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

k k is an integer from 1 to 12, inclusive. In certain embodiments, k=1 to 6, e.g., 1, 2, or 3.

p and m

Each occurrence of p is independently an integer from 1 to 5, inclusive. In certain embodiments, each occurrence of p is the same. In certain embodiments, p=1, 2 or 3. In certain embodiments, p=1.

Each occurrence of m is independently an integer from 1 to 5, inclusive. In certain embodiments, each occurrence of m is the same. In certain embodiments, m=1, 2 or 3. In certain embodiments, m=1.

n and v

Each occurrence of n is independently an integer from 0 to 5, inclusive, with the proviso that within each k-branch at least one occurrence of n is ≥1. Branches within a given k-branch are referred to herein as n-branches.

In certain embodiments, each occurrence of [A] in a p-bracketed moiety is substituted by a number of n-bracketed moieties corresponding to a value of n≥1, e.g., see formula (Ia) above. In some such embodiments, each occurrence of n in the conjugate is the same. In some of these embodiments, n=1 or 2.

In other embodiments, only terminal occurrences of [A] in a p-bracketed moiety are substituted by a number of n-bracketed moieties corresponding to a value of n≥1, e.g., see formula (Ib) above. In certain embodiments, each k-branch includes just one occurrence of n≥1 (i.e., all other occurrences of n=0). In some such embodiments, each occurrence of n in the conjugate is the same. In some of these embodiments, n=1 or 2.

Each occurrence of v is independently an integer from 0 to 5, inclusive, with the proviso that within each k-branch at least one occurrence of v is ≥1.

In certain embodiments, each occurrence of [A] in an m-bracketed moiety is substituted by a number of B moieties corresponding to the value of v≥1, e.g., see formula (Ic) above. In some such embodiments, each occurrence of v in the conjugate is the same. In some of these embodiments, v=1 or 2.

In other embodiments, only terminal occurrences of [A] in an m-bracketed moiety are substituted by a number of B moieties corresponding to a value of v≥1, e.g., see formula (Id) above. In certain embodiments, each k-branch includes just one occurrence of v≥1 (i.e., all other occurrences of v=0). In some such embodiments, each occurrence of v in the conjugate is the same. In some of these embodiments, v=1 or 2. In certain embodiments, each n-branch includes at least one occurrence of v≥1. In certain embodiment, each n-branch includes just one occurrence of v≥1 (i.e., all other occurrences of v=0). In some such embodiments, each occurrence of v in the conjugate is the same. In some of these embodiments, v=1 or 2.

Drug Loading

In general, the amount of drug that is loaded onto a conjugate can be controlled by adjusting the molecular weight of the conjugate framework and/or the level of chemical activation (i.e., when pendant groups are added to the framework). In various embodiments, the drug loading level may be in the range of 5 to 99% w/w of drug to conjugate. In various embodiments, loading levels within the narrower range of 50 to 99% may be used, e.g., in the range of 80 to 99%.
Other It is to be understood that while the preceding sections describe components of the conjugates (e.g., ligand, drug, framework) under separate headings, the present disclosure encompasses conjugates that are comprised of any and all of the disclosed ligands, drugs and frameworks.

Methods for Preparing Insulin-Conjugates

As described in the Examples, we have exemplified methods for preparing the aforementioned conjugates using human recombinant insulin as an exemplary insulin molecule and aminoethylglucose (AEG), aminoethylmannose (AEM), aminoethylbimannose (AEBM), aminoethyltrimannose (AETM), aminoethylfucose (AEF), β-aminoethyl-N-acetylglucosamine (AEGA), and/or glucosamine (GA) as exemplary ligands. Without limitation, conjugates with two ligands per conjugation site and with short distances between all framework components may be prepared using tris(hydroxymethyl)aminomethane (Tris), tris-succinimidyl aminotriacetate (TSAT), tris-succinimidyl-1,3,5-benzenetricarboxylate (TSB), and benzene-1,3,5-tricarboxy-(N-4-butyric-NHS-ester)amide (TSB-C4) as conjugate frameworks. If more space between framework components is desired, then succinimidyl (6-aminocaproyl)aminotriacetate (TSAT-C6), succinimidyl (6-amino(PEO-6))aminotriacetate (TSAT-PEO-6), benzene-1,3,5-tricarboxy-(N-6-aminocaproic-NHS ester)amide (TSB-C6), and benzene-1,3,5-tricarboxy-(N-10-aminodecanoic-NHS ester)amide (TSB-C10) may be used. The TSAT-C6 spacer arm chemistry imparts more hydrophobic character to the conjugate as compared to TSAT-PEO-6.

For example, for purposes of illustration, in one embodiment, both the ligand (e.g., AEG, AEM, AEMB and AETM) and insulin may be reacted to a TSAT-C6 framework through the terminal activated esters to produce insulin-TSAT-C6-AEG-2, insulin-TSAT-C6-AEM-2, insulin-TSAT-C6-AEMB-2, and insulin-TSAT-C6-AETM-2 conjugates. The various ligands are synthesized ahead of time as discussed in the Examples. In some embodiments, the A1 and B29 amino groups of insulin are BOC-protected as described in the Examples so that each insulin can only react at the Phe-B1 α-amino group. In some embodiments, the B1 and B29 amino groups of insulin are BOC-protected as described in the Examples so that each insulin can only react at the Gly-A1 α-amino group. Approximately one equivalent of BOC-insulin as a 40-50 mg/ml solution in DMSO is added at room temperature to a 50 mg/ml solution of TSAT-C6 in DMSO containing excess triethylamine and allowed to react for approximately one hour. Next, an excess of AEG, AEM, AEBM, and/or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted BOC2-insulin. The desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150 M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

In another aspect, reaction may take place at the B29 epsilon-amino group using unprotected insulin in carbonate buffer, since under those conditions the B29 amino group is the most reactive of the three amino groups present in wild-type insulin. In an exemplary synthesis, the framework containing N-terminal activated esters is dissolved at 60 mM in anhydrous DMSO followed by the addition of triethylamine (TEA). The solution is stirred rapidly for 10 minutes at room temperature. In parallel, a 448 mM solution of ligand is prepared in an appropriate volume of anhydrous DMSO. Once dissolved, enough ligand solution is added dropwise over the course of ten minutes to provide a number of reactive equivalents equal to 1.5 times the number of activated ester groups on the framework, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one hour at room temperature.

The insulin molecule is then dissolved separately at 17.2 mM in sodium carbonate buffer (0.1 M, pH 11) and the pH subsequently adjusted to 10.8 with 1.0 N sodium hydroxide. Once dissolved, the entire framework/DMSO/ligand/TEA solution is added dropwise over the course of 75 minutes to the insulin/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC. Once collected, the solution is rotovapped to remove acetonitrile and lyophilized to obtain pure conjugate.

In another aspect, B29-monosubstituted insulin-conjugates are synthesized using N-terminal protecting amino acid sequences using similar methods to those reported in U.S. Pat. No. 7,402,565. Specifically, N-terminal peptide sequences are engineered onto the insulin A-chain and B-chain such that the protecting amino acid sequences contain $Arg^{40}$ and $Arg^{B0}$ to give an insulin intermediate. Conjugation takes places at $Lys^{B29}$ on the insulin intermediate, while the N-termini are protected from conjugation side-products. The conjugated insulin intermediate is treated with trypsin to cleave the N-terminal protecting amino acid sequences to give an insulin-conjugate wherein solely $Lys^{B29}$ is conjugated. In some embodiments, the insulin intermediate is derived from a single chain insulin precursor as described in U.S. Pat. No. 7,402,565. In some embodiments, the insulin intermediate is a mutant that contains a conjugation site other than $Lys^{B29}$ and an analogous synthesis to the one described for $Lys^{B29}$ is performed.

It will be appreciated that these exemplary procedures may be used to produce other conjugates with different ligands and insulin molecules, different conjugation chemistries, different separations between framework components, and/or different valencies by substituting the TSAT-C6 framework with a different framework as described below.

For example, if yet more distance is required between framework components and/or a preserved charge is required at the site of conjugation, then an appropriately-sized amine-bearing diethyl acetal (e.g., aminopropionaldehyde diethyl acetal (APDA) or aminobutyraldehyde diethyl acetal (ABDA)) may be conjugated to one of the reactive groups on the frameworks listed here followed by complete reaction of the remaining reactive groups with the ligand of interest (e.g. AEM, AEBM, or AETM). A reactive aldehyde group can then be revealed from the diethyl acetal under acidic conditions followed by a reductive amination with insulin to complete the insulin conjugation step then ABDA-TSAT, ABDA-LCT-SAT, etc. may be employed.

In yet another example, tetrakis-(N-succinimidyl carboxypropyl)pentaerythritol (TSPE), may be used to attach three ligands per conjugation site for increased multivalency. It will also be appreciated by those skilled in the art that any of the above teachings may be used to produce hyperbranched (e.g., dendrimer-like) conjugates with even higher order valencies. For example, Rockendorf and Lindhorst provide a comprehensive review of current approaches for producing hyperbranched structures in *Topics in Current Chemistry.* 217: 202-238, 2001.

Furthermore, ligands already containing a predetermined degree of multivalency may again be reacted according to the procedures described above to produce even higher orders of ligand multiplicity. For example, a divalent AEM-2, AEBM-2, or AETM-2 molecule containing a terminal reactive amine may be prepared by conjugating two of each ligand to a suitable framework to which a reactive amine is also conjugated. A trivalent AEM-3, AEBM-3, or AETM-3 molecule containing a terminal reactive amine may be prepared by conjugating three of each ligand to a suitable framework to which a reactive amine is also conjugated. The $NH_2$-divalent saccharides may be reacted with the same frameworks described above to produce insulin-conjugates with 4 and 6 ligands per insulin molecule. The $NH_2$-trivalent saccharides may be reacted with the same frameworks described above to produce drug conjugates with 6 and 9 ligands per insulin molecule.

In all cases, it should be recognized that a mixture of different ligands may be conjugated to the same insulin molecule via a multivalent framework by adjusting the framework chemistry, valency, and the ligand: framework stoichiometry. For example, Insulin-AEM-1-AEBM-1, Insulin-AEBM-1-AETM-1, Insulin-AEM-2-AETM-2, and Insulin-AEM-1-AETM-2 may all be synthesized according to this mixed ligand method.

In some cases, it may be desirable to conjugate the ligand to the framework through a different means than the insulin molecule. For example, a divalent maleimide/monovalent activate ester functionalized framework (e.g., succinimidyl-3,5-dimaleimidophenyl benzoate (SDMB)) may be used to conjugate two sulfhydryl functionalized ligands and one insulin molecule in separate steps. For example, an insulin molecule may be conjugated to the activated ester portion of the framework using methods described herein. In a separate step, the aminoethyl saccharide (AEM, AEBM, AETM) may be converted to a terminal sulfhydryl-bearing ligand by reaction with 4-iminothiolane. Finally, the framework-di-maleimide-insulin conjugate may be mixed with an excess of sulfhydryl-functionalized saccharide to produce the resulting divalent-ligand-insulin conjugate.

Crystallization of Insulin-Conjugates

It has been surprisingly found that certain insulin-conjugates described herein can be crystallized without the use of additives such as protamine or zinc. Crystalline formulations of insulin-conjugates may be advantageous in improving batch to batch reproducibility, increasing formulation stability, and decreasing particle agglomeration over long periods of storage.

As described in the Examples, screening experiments can be performed to determine appropriate crystallization conditions. Generally, a solution of the insulin-conjugate to be crystallized is dissolved in water and suspended over a buffer, and solutions are observed for evidence of crystallization. The crystalline insulin-conjugate can then be prepared on a larger scale using an appropriate buffer identified in the screening experiment.

In certain embodiments, the framework of the crystalline insulin-conjugate is conjugated at the $Lys^{B29}$ position. In certain embodiments, the crystalline insulin-conjugate is one of the conjugates shown in FIG. 2. In certain embodiments, the crystalline insulin-conjugate is I-6, I-7, or I-9.

In certain embodiments, the buffer used for crystallization has a pH greater than 7. In certain embodiments, the buffer has a pH between about 7.5 and about 8.5. In certain embodiments, the buffer is a phosphate, TRIS, or HEPES buffer.

In certain embodiments, the buffer used for crystallization is a phosphate buffer. In certain embodiments, the buffer has a higher concentration of potassium than sodium. In certain embodiments, the buffer has a higher concentration of potassium phosphate dibasic than sodium phosphate monobasic. In certain embodiments, the buffer has a pH in the range of about 6 to 9. In certain embodiments, the buffer has a pH of about 8. In certain embodiments, the buffer has a pH of about 8.2. In certain embodiments, the buffer is sodium phosphate monobasic monohydrate, potassium phosphate dibasic, with a pH of about 8.2.

In certain embodiments, the crystallization occurs in the presence of one or more additives. In certain embodiments, the additive is m-cresol, phenol, protamine, poly(arginine), glycerol, zinc chloride, or zinc acetate. In certain embodiments, the additive is polyethylene glycol.

In certain embodiments, an organic solvent is added to facilitate crystallization. In certain embodiments, the organic solvent is methanol, ethanol, or isopropanol. In certain embodiments, the organic solvent is removed prior to the final preparation of a pharmaceutical composition.

Formulations of Crystalline Insulin-Conjugates

As discussed in the Examples, in certain embodiments it may be advantageous to administer a crystalline insulin-conjugate in a sustained fashion (i.e., in a form that exhibits an absorption profile that is more sustained than soluble recombinant human insulin), thus providing a sustained level of conjugate that can respond to fluctuations in glucose on a timescale that it more closely related to the typical glucose fluctuation timescale (i.e., hours rather than minutes). In certain embodiments, the sustained release formulation may exhibit a zero-order release of the conjugate when administered to a mammal under non-hyperglycemic conditions (i.e., fasted conditions).

It will be appreciated that any formulation that provides a sustained absorption profile may be used. In certain embodiments, sustained absorption may be achieved by combining the crystalline insulin-conjugate with other ingredients that slow its release properties into systemic circulation. For example, PZI (protamine zinc insulin) formulations may be used for this purpose. As described in the Examples, we have found that in certain embodiments the absorption profile and stability of PZI formulations prepared with amorphous insulin-conjugates are sensitive to the absolute and relative amounts of protamine and zinc included in the formulation. For example, whereas commercial PZI and NPH (neutral protamine Hagedorn) insulin formulations require only about 0.05 to about 0.2 mg protamine/mg insulin, some PZI-conjugate preparations required about 1 to about 5 mg protamine/mg conjugate in order to effectively sustain the absorption profile. Furthermore, while commercial protamine insulin preparations contain about 0.006 mg zinc/mg insulin, we have found that increasing the zinc concentration along with the protamine concentration can, in certain embodiments, lead to more stable, easily dispersible formulations. In some cases, the zinc content is in the range of about 0.05 to about 0.5 mg zinc/mg conjugate. Furthermore, we have also unexpectedly found that in certain embodiments, insulin-conjugates substituted at the B1-amine group require more protamine and zinc to effectively sustain the release profile versus an insulin-conjugate substituted at the B29-amine group.

In certain embodiments, a pre-crystallized insulin-conjugate dispersion is mixed with protamine to form a crystalline insulin-conjugate protamine formulation. In some embodiments, the dispersion is neutralized to physiological buffer strength during formulation.

In certain embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In certain embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In certain embodiments, a formulation of the present disclosure includes protamine and zinc in a ratio (w/w) in the range of about 100:1 to about 5:1, for example, from about 50:1 to about 5:1, e.g., about 40:1 to about 10:1. In certain embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

In certain embodiments, one or more of the following components is added to a formulation: an antimicrobial preservative, an isotonic agent, and/or an unconjugated insulin molecule.

In certain embodiments, a formulation of the present disclosure includes an antimicrobial preservative (e.g., m-cresol, phenol, methylparaben, or propylparaben). In certain embodiments the antimicrobial preservative is m-cresol. For example, in certain embodiments, a formulation may include from about 0.1 to about 1.0% v/v m-cresol. For example, from about 0.1 to about 0.5% v/v m-cresol, e.g., about 0.15 to about 0.35% v/v m-cresol.

In certain embodiments, a formulation of the present disclosure includes a polyol as isotonic agent (e.g., mannitol, propylene glycol or glycerol). In certain embodiments the isotonic agent is glycerol. In certain embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In certain embodiments, a formulation of the present disclosure includes an amount of unconjugated insulin molecule. In certain embodiments, a formulation includes a molar ratio of conjugated insulin molecule to unconjugated insulin molecule in the range of about 100:1 to 1:1, e.g., about 50:1 to 2:1 or about 25:1 to 2:1.

In certain embodiments the present disclosure provides a sustained release formulation comprising a crystalline conjugate of the present disclosure, wherein the formulation comprises protamine and zinc. In certain embodiments, the framework of the crystalline insulin-conjugate is conjugated at the $Lys^{B29}$ position. In certain embodiments, the crystalline insulin-conjugate is one of the conjugates shown in FIG. 2. In certain embodiments, the crystalline insulin-conjugate is I-6, I-7, or I-9.

In certain embodiments, the formulation includes from about 1 to about 5 mg protamine/mg conjugate; and from about 0.1 to about 0.25 mg zinc/mg conjugate.

In certain embodiments, the formulation includes protamine and zinc in a ratio (w/w) in the range of about 40:1 to about 10:1.

In certain embodiments, the formulation further comprises an amount of unconjugated insulin molecule. In certain embodiments, the formulation comprises a molar ratio of conjugated insulin molecule to unconjugated insulin molecule in the range of about 25:1 to about 2:1.

In certain embodiments, the formulation further comprises an antimicrobial preservative. In certain embodiments, the antimicrobial preservative is m-cresol. In certain embodiments, the formulation comprises from about 0.15 to about 0.35% v/v m-cresol.

In certain embodiments, the formulation further comprises an isotonic agent. In certain embodiments, the isotonic agent is glycerol. In certain embodiments, the isotonic agent is NaCl.

In certain embodiments, the formulation comprises from about 0.1 to about 0.2 M NaCl.

In certain embodiments, the formulation comprises:
protamine and zinc in a ratio (w/w) in the range of about 40:1 to about 10:1;
a molar ratio of conjugated insulin molecule to unconjugated insulin molecule in the range of about 25:1 to about 2:1;
about 0.15 to about 0.35% v/v m-cresol; and
glycerol or from about 0.1 to about 0.2 M NaCl.

In certain embodiments, the formulation comprises:
about 3.6 mg protamine/mg conjugate; and
about 0.2 mg zinc/mg conjugate.

In certain embodiments, the formulation comprises:
about 3.6 mg protamine/mg conjugate;
about 0.2 mg zinc/mg conjugate; and
a molar ratio of conjugated insulin molecule to unconjugated insulin molecule of about 5:1.

In certain embodiments, the formulation comprises:
about 3.6 mg protamine/mg conjugate;
about 0.2 mg zinc/mg conjugate;
a molar ratio of conjugated insulin molecule to unconjugated insulin molecule of about 5:1; and
about 0.2% v/v m-cresol.

In certain embodiments, the formulation comprises:
about 3.6 mg protamine/mg conjugate;
about 0.2 mg zinc/mg conjugate;
a molar ratio of conjugated insulin molecule to unconjugated insulin molecule of about 5:1;
about 0.2% v/v m-cresol; and
glycerol or about 0.15 M NaCl.

Uses of Crystalline Insulin-Conjugates

In another aspect, the present disclosure provides methods of using crystalline insulin-conjugates. In general, the crystalline conjugates can be used to controllably provide bioactive insulin in response to a saccharide (e.g., glucose or an exogenous saccharide such as mannose, alpha-methyl mannose, L-fucose, etc. as described herein). The disclosure encompasses treating a disease or condition by administering a crystalline insulin-conjugate of the present disclosure. Although the conjugates can be used to treat any patient (e.g., dogs, cats, cows, horses, sheep, pigs, mice, etc.), they are most preferably used in the treatment of humans. A crystalline insulin-conjugate can be administered to a patient by various routes. In general the most appropriate route of administration will depend upon a variety of factors including the nature of the disease or condition being treated, the condition of the patient, etc. In general, the present disclosure encompasses administration by oral, intramuscular, subcutaneous, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995. In various embodiments, a crystalline insulin-conjugate suspension may be administered subcutaneously, e.g., by injection. The suspension carrier can be an aqueous solution including, but not limited to, sterile water, saline or buffered saline.

In general, a therapeutically effective amount of a crystalline insulin-conjugate will be administered. By a "therapeutically effective amount" is meant a sufficient amount of the crystalline insulin-conjugate to treat the disease or condition at a reasonable benefit/risk ratio, which involves a balancing of the efficacy and toxicity of the conjugate. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the insulin. Although in general a large therapeutic index is preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the average daily dose of insulin is in the range of 10 to 200 U, e.g., 25 to 100 U (where 1 Unit of insulin is ~0.04 mg). In certain embodiments, an amount of conjugate with these insulin doses is administered on a daily basis. In certain embodiments, an amount of conjugate with 5 to 10 times these insulin doses is administered on a weekly basis. In certain embodiments, an amount of conjugate with 10 to 20 times these insulin doses is administered on a bi-weekly basis. In certain embodiments, an amount of conjugate with 20 to 40 times these insulin doses is administered on a monthly basis.

In certain embodiments, a crystalline insulin-conjugate of the present disclosure may be used to treat hyperglycemia in a patient (e.g., a mammalian patient). In certain embodiments, the patient is diabetic. However, the present methods are not limited to treating diabetic patients. For example, in certain embodiments, a conjugate may be used to treat hyperglycemia in a patient with an infection associated with impaired glycemic control. In certain embodiments, a crystalline insulin-conjugate may be used to treat diabetes.

In certain embodiments, when a crystalline insulin-conjugate or formulation thereof of the present disclosure is administered to a patient (e.g., a mammalian patient) it induces less hypoglycemia than an unconjugated version of the insulin molecule. In certain embodiments, a crystalline insulin-conjugate formulation of the present disclosure induces a lower HbA1c value in a patient (e.g., a mammalian patient) than a formulation comprising an unconjugated version of the insulin molecule. In certain embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In certain embodiments, the formulation leads to an HbA1c value of less than 7%, e.g., in the range of about 4 to about 6%. In certain embodiments, a formulation comprising an unconjugated version of the insulin molecule leads to an HbA1c value in excess of 7%, e.g., about 8 to about 12%.

It will be understood that the total daily usage of a provided conjugate for any given patient will be decided by the attending physician within the scope of sound medical judgment. The specific therapeutically effective amount for any particular patient will depend upon a variety of factors including the disease or condition being treated; the activity of the specific insulin molecule employed; the specific composition employed; the age, body weight, general health, sex and diet of the patient; the time of administration, route of administration and rate of excretion of the specific insulin molecule employed; the duration of the treatment; drugs used in combination or coincidental with the specific insulin molecule employed; and like factors well known in the medical arts. In various embodiments, a conjugate of the present disclosure may be administered on more than one occasion. For example, the present disclosure specifically encompasses methods in which a crystalline insulin-conjugate suspension is administered by subcutaneous injection to a patient on a continuous schedule (e.g., once a day, once every two days, once a week, once every two weeks, once a month, etc.).

In various embodiments, a crystalline insulin-conjugate of the present disclosure may be administered to a patient who is receiving at least one additional therapy. In various embodiments, the at least one additional therapy is intended to treat the same disease or disorder as the administered conjugate.

Insulin sensitizers (e.g., biguanides such as metformin, glitazones) act by increasing a patient's response to a given amount of insulin. A patient receiving an insulin sensitizer will therefore require a lower dose of a crystalline insulin-conjugate of the present disclosure than an otherwise identical patient would. Thus, in certain embodiments, a crystalline insulin-conjugate may be administered to a patient who is also being treated with an insulin sensitizer. In various embodiments, the crystalline insulin-conjugate of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the crystalline insulin-conjugates of the present disclosure are only effective for this subclass of patients when they provide high levels of bioactive insulin in a suitable timeframe. In certain embodiments, the treatment of this subclass of patients may be facilitated by combining the two approaches. Thus in certain embodiments, a traditional insulin-based therapy is used to provide a baseline level of insulin and a crystalline insulin-conjugate of the present invention is administered to provide a controlled supplement of bioactive insulin when needed by the patient. Thus, in certain embodiments, crystalline insulin-conjugates may be administered to a patient who is also being treated with insulin. In various embodiments, the insulin may be administered at up to 75% of the normal dose required in the absence of a conjugate of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Exogenous Trigger

As mentioned previously, the methods, conjugates and compositions that are described herein are not limited to glucose responsive-conjugates. As demonstrated in the Examples, several exemplary glucose-responsive conjugates were also responsive to exogenous saccharides such as alpha-methyl mannose and L-fucose. It will therefore be appreciated that in certain embodiments a conjugate may be triggered by exogenous administration of a saccharide other than glucose such as alpha-methyl mannose and L-fucose or any other saccharide that can alter the PK or PD properties of the conjugate.

Once a conjugate has been administered as described above (e.g., as a sustained release formulation) it can be triggered by administration of a suitable exogenous saccharide. In a certain embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide. It is also be to be understood that the methods of administration for the conjugate and exogenous saccharide may be the same or different. In various embodiments, the methods of administration are different (e.g., for purposes of illustration a crystalline insulin-conjugate may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the crystalline insulin-conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in *Remington's Pharmaceutical Sciences*, 19th ed., Mack Publishing Co., Easton, Pa., 1995.

It will also be appreciated that the relative frequency of administration of a crystalline insulin-conjugate of the present disclosure and an exogenous saccharide may be the same or different. In certain embodiments, the exogenous saccharide is administered more frequently than the conjugate. For example, in certain embodiment, the conjugate may be administered daily while the exogenous saccharide is administered more than once a day. In certain embodiment, the conjugate may be administered twice weekly, weekly, biweekly or monthly while the exogenous saccharide is administered daily. In certain embodiments, the conjugate is administered monthly and the exogenous saccharide is administered twice weekly, weekly, or biweekly. Other variations on these schemes will be recognized by those skilled in the art and will vary depending on the nature of the conjugate and formulation used.

EXAMPLES

The structures of exemplary conjugates I-5 to I-11 and I-17 that are described and used in the Examples are shown in FIG. 2.

It is to be understood that these methods can be modified to produce other conjugates that fall within the scope of the invention.

Example 1

Synthesis of Azidoethylglucose (AzEG)

a. Synthesis of Bromoethyleglucose

DOWEX 50Wx4 resin (Alfa Aesar, Ward Hill, Mass.) was washed with deionized water to remove color. A mixture of 225 gm D-glucose (1.25 mol; 1 equiv., Alfa Aesar) and 140 gm DOWEX 50Wx4 was treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction was monitored by TLC (20% methanol/dichloromethane (DCM)). Reaction was complete after about four hours, and it was allowed to cool to room temperature. The solution was filtered to remove the resin, and the resin washed with ethyl acetate and DCM. The resulting filtrate was stripped to an amber oil in a rotory evaporator. A total of 400 gm after stripping.

The amber oil was purified on silica gel (4 kg silica packed in DCM) in the following manner. The crude was dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) were pooled and stripped to dryness to afford 152 gm of 1-α-bromoethyl-glucose (42%).

b. Conversion of Bromoethylglucose to Azidoethylglucose (AzEM)

A 5 L round bottom three-necked flask, equipped with a heating mantle, an overhead stirrer, and a thermometer, was charged with 150 gm bromoethylglucose (525 mmol). The oil was dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution was cooled to room temperature and concentrated to dryness on the rotovap. The solid residue was digested with 3×500 mL of 5:1 vol. $CHCl_3$:MeOH at 40 C. The combined organic portions were filtered and evaporated to dryness to afford azidoethylglucose (86 gm) as an off-white solid. TLC (20% MeOH/DCM; char with $H_2SO_4$): single spot, indistinguishable from the starting material.

c. Repurification of Azidoethylglucose 32 gm of azidoethylglucose was taken into 100 mL water. The turbid solution was filtered through a glass microfibre filter (Whatman GF/B). The golden filtrate was evaporated to a solid on a rotovapor. The solid was taken into methanol (100 mL) and the turbid solution was again filtered through a glass microfibre filter. The resulting pale yellow filtrate was stripped to a solid under vacuum.

The solid was taken into a minimum of methanol (50 mL) and ethyl acetate (150 mL) was added slowly with stirring. The heavy slurry was cooled and filtered. The solid was air dried (hygroscopic) and put in a 60 C oven overnight. TLC has very little origin material. Yield 15.4 gm. The Mother Liquor was evaporated under vacuum to a yellow gum. No attempt was made to further purify this material at this time.

Example 2

Synthesis of Azidoethylmannose (AzEM)

a. Synthesis of Bromoethylmannose

DOWEX 50Wx4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50Wx4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotory evaporator.

The amber oil is purified on silica gel (4 kg silica packed in DCM) in the following manner. The crude is dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5 L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. $CHCl_3$:MeOH at 40 C. The combined organic portions are filtered and evaporated to dryness to afford azidoethylmannose as an off-white solid.

c. Repurification of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 3

Synthesis of Azidoethylmannobiose (AzEBM)

The AzEM compound from Example 2 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 4

Synthesis of Azidoethylmannotriose (AzETM)

a. 1-α-bromo-2,3,4,6-tetrabenzoyl-mannose

To a 500 mL 3-neck flask containing a stir bar and nitrogen inlet was added 40 gm (60.9 mmole) of pentabenzoylmannose and 80 mL methylene chloride. The resulting solution was cooled in an ice bath to <5 C, and 80 mL 33% HBr-acetic acid solution was added via an addition funnel at such a rate to maintain the reaction temperature <10 C. Upon complete addition (~30 min.) the ice bath was removed and stirring was continued for 3 hours.

The reaction solution was diluted with an equal volume (160 mL) of DCM and extracted successively with water (2×500 mL), saturated bicarbonate (2×50 mL) and Brine (1×50 mL), dried over magnesium sulfate and the solvent evaporated to give 41 gm of solid foam. (Theoretical yield 40.1 gm) and was stored under $N_2$ in a freezer. This material was used without further purification. The reaction was monitored by TLC: silica gel (Hexane/Ethyl Acetate, 7/3) starting material $R_f$ 0.65, product $R_f$ 0.8 UV visualization. $^1H$ NMR ($CDCl_3$) δ 8.11 (d, 2H), 8.01 (m, 4H), 7.84 (d, 2H), 7.58 (m, 4H), 7.41 (m, 6H), 7.28 (t, 2H), 6.58 (s, 1H), 6.28 (m, 2H), 5.8 (m, 1H), 4.75 (dd, 1H) 4.68 (dd, 1H) 4.5 (dd, 1H).

b. 1-Azidoethyl-2,4-dibenzoylmannose

To a 1.0 L, 3-neck flask containing a stir bar, nitrogen inlet and 300 mL of anhydrous acetonitrile was added 25 gm 1-azidoethylmannose (100.4 mmole), and 50 mL triethyl orthobenzoate (220 mmole, 2.2 equiv.). The resulting slurry was stirred at room temperature and 0.8 mL (10 mmole) trifluoroacetic acid (TFA) was added neat. The solution cleared within 10 minutes and stirring was continued for an additional two hours, then 25 mL of 10% aqueous TFA was added and stirring was continued for an additional 2 hours to hydrolyze the intermediate to the ester isomers. The solvent was evaporated under vacuum to a viscous oil, which was triturated with 50 mL DCM and again evaporated to a viscous oil. Toluene (70 mL) was added to the residue and the viscous solution was seeded with 2,4-dibenzoylazidoethylmannose. A fine precipitate formed within 15 minutes and stirring was continued overnight at room temperature. The resulting heavy suspension was set in the freezer for 2-4 hours, then filtered and the solid washed with ice cold toluene (2×10 mL). The solid was air dried to a constant weight to give 21 gm (TY 22.85 gm @ 50% isomeric purity) of ~95% isomeric purity. The product was taken into 40 mL toluene, stirred for 1 hour and then set in the freezer for an additional 2 hours. The solid was filtered and washed (2×10 mL) with ice cold toluene and air dried to a constant weight to give 18.5 gm of the single isomer product 2,4-dibenzoylazidoethylmannose in 83% yield. The mother liquors contained the undesired isomer and a small amount of the desired isomer. The reaction was monitored by TLC: SG (Hexane/Ethyl Acetate 7/3) Starting Material $R_f$ 0.0, orthoester intermediate $R_f$ 0.9. (Hexane/Ethyl Acetate: 8/2) SM $R_f$ 0.8, desired isomer $R_f$ 0.4, un-desired isomer $R_f$ 0.2 $^1H$ NMR 300 MHz ($CDCl_3$) δ 8.12 (t, 4H), 7.66

(t, 2H), 7.5 (m, 4H), 5.56 (t, 1H), 5.48 (m, 1H), 5.14 (m, 1H), 4.5 (dd, 1H), 4.0 (m, 2H), 3.8 (m, 3H), 3.56 (m, 1H), 3.44 (m, 1H).

c. Perbenzoylated-man(α-1,3)-man(α-1.6)-α-1-azidoethylmannopyranoside

To a 1.0 L 3-neck flask with a stir bar, nitrogen inlet was added 41 gm crude 1-bromo-tetrabenzoymannose (60.9 mmole, ~2.5 equiv.) in 185 mL DCM. To this was added 11.2 gm 2,4-dibenzoylazidoethylmannose (24.5 mmole) followed by 11.2 gm 4 A sieves. The slurry was stirred a room temperature for 10 minutes and cooled to −15° C. in a methanol/ice bath.

In a separate dark vessel was added 190 mL toluene followed by 15.1 gm silver-trifluoromethanesulfonate (AgOTf) (58.8 mmole, 2.4 equiv.) and was stirred into solution in the dark. This solution was transferred to a large addition funnel, and added drop-wise to the stirring suspension while protecting the reaction from light. The reaction temperature was maintained <−10 C by adjusting the AgOTf addition rate. Upon complete addition (~30 minutes) the cold bath was removed and the reaction stirred for an additional 2 hours until a single product remained by TLC (SG, Hexane/Ethyl Acetate: 7/3, Bromo $R_f$ 0.9, azido $R_f$ 0.4, trios product $R_f$ 0.5, uv visualization).

Triethylamine (7 mL, 5.0 equiv.) was added followed by 200 mL DCM. The resulting slurry was filtered through a pad of silica gel and celite and washed with 2×75 mL DCM. The solvent was evaporated under vacuum and the residue taken into ethyl acetate and washed sequentially with water (2×100 mL), bicarb (2×50 mL), brine (1×75 mL) and dried over magnesium sulfate. The solvent was evaporated under vacuum to give 39 gm of solid foam (TY 39.5 gm). $^1$H NMR 300 MHz (CDCl$_3$) δ 8.3 (d, 2H), 8.2 (m, 8H), 7.85 (d, 4H), 7.75 (dd, 4H), 7.3-7.65 (m, 30H), 7.2 (t, 2H), 6.05 (m, 4H), 5.9 (t, 2H), 5.63 (m, 2H), 5.38 (s, 2H), 5.18 (d, 1H), 4.65 (m, 4H), 4.5 (m, 2H), 4.35 (m, 4H), 3.8 (m, 2H), 3.54 (m, 2H).

d. Man(α-1,3)-man(α-1.6)-α-1-azidoethylmannopyranoside

To a stirring suspension of 3.0 gm perbenzoylated-man (α-1,3)-man(α-1.6)-α-1-azidoethylmannopyranoside (1.86 mmole) in 40 mL methanol was added 0.2 mL 4.28M sodium methoxide in methanol. The resulting suspension was stirred 20 hours at room temperature giving a clear solution. The completion of the reaction was monitored by TLC, (SG, hexane/ethyl acetate: 8/2 SM $R_f$ 0.4, product $R_f$ 0.0).

The methanol was evaporated under vacuum giving an oily semi-solid. The residue was taken into ethyl acetate (50 mL) and stirred for 3 hours. The solid was filtered, washed with fresh ethyl acetate (2×20 mL) and air dried to a constant weight to give 1.09 gm (TY 1.07 gm) of product. The mother liquors contained residual methyl benzoate, the de-protection by-product.

Example 5

Synthesis of aminoethyl-saccharides (AEG, AEM, AEBM, AETM) from azidoethyl-saccharides (AzEG, AzEM, AzEBM, AzETM)

The azido-terminated compounds from Examples 1-4 are readily hydrogenated at room temperature by using palladium/carbon catalyst, a small amount of acetic acid, and ethanol as a solvent to give the corresponding amine-terminated compounds. FIG. 1 shows the chemical structures of AEG, AEM, AEBM, AETM. The process is identical to the one described for AETM below, except that those skilled in the art will understand that the amounts of reagents, solvents, etc. should be scaled to the number of moles of saccharide-ligand to be hydrogenated.

a. Man (α-1,3)-Man(α-1.6)-α-1-aminoethylmannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC (SG, Methanol, SM $R_f$ 0.75, Pdt $R_f$ 0.0, PMA vis.). The suspension was filtered over celite, which was rinsed with ethanol (2×50 mL) and the filtrate concentrated under vacuum.

HPLC of this material (C18, 3% Acetonitrile/97% 0.1% H$_3$PO$_4$, 220 nm, 2 ml/min) gave uv adsorption of the injection column void material, Rt 2.5 minutes, indicative of benzoate ester.

The filtrate was diluted with 70 mL water and 12 mL of 1N NaOH and the solution stirred overnight at room temperature (HPLC: no uv material at column void Rt 2.5 min., uv material at Rt 10.5 minutes co-eluting with benzoic acid). 2 gm of decolorizing charcoal were added and the stirring suspension heated to 80 C, cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid byproducts. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for 5 hours to give 4.1 gm of a white granular solid (TY 5.1 gm). The NMR was clean of any aromatic protons. $^1$H NMR 300 MHz (D$_2$O) δ 5.08 (s, 1H), 4.87 (s, 1H), 4.81 (s, 1H), 4.8-3.6 (m, 18H), 2.9 (m, 2H).

Example 6

Synthesis of NH$_2$—B29-BOC2(A1,B1)-Insulin a. Fmoc-1-(B29)-Insulin

In a typical synthesis, 4 gm of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.2 equivalents of 9-fluorenylmethyl N-succinimidyl carbonate (Fmoc-NHS) (Sigma Aldrich, St. Louis, Mo.) is slowly added to the insulin-TEA solution as a 1.0 M solution of the Fmoc-NHS in THF. The reaction is mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 μl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 20% of the Fmoc1 product, 65% of the Fmoc2 product, and 15% of unreacted insulin.

A preparative reverse phase HPLC method is used to isolate the pure desired Fmoc1-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltraPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired Fmoc1 peak elutes at approximately 3 minutes after the unreacted RHI peak, followed closely by the Fmoc2-insulin peak. Once collected, the solution is rotovapped to remove acetonitrile and lyophilized to obtain pure Fmoc1-insulin powder. Identity is verified by LC-MS (HT Laboratories, San Diego, Calif.) and site of conjugation determined by N-terminal sequencing (Western Analytical, St. Louis, Mo.).

b. BOC2(A1,B1)-Fmoc-(B29)-Insulin

In a typical synthesis, 1 g of Fmoc1-(B29)-insulin is dissolved in 25 ml of anhydrous DMSO at room temperature followed by the addition of 1 ml of triethylamine (TEA). The solution is stirred for 30 minutes at room temperature. Next, 0.379 ml (2.2 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 1 ml of a stock solution containing 250 ul of ethanolamine in 5 ml of DMSO followed by mixing for five minutes. After quenching, the entire solution is poured into 400 ml of acetone and mixed briefly with a spatula. Next, 8×100 µl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×100 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains greater than 90% of the desired BOC2-Fmoc-1 product.

A preparative reverse phase HPLC method is used to isolate the pure BOC2-Fmoc-1-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltraPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2-Fmoc-1 peak elutes at approximately 5 minutes after the Fmoc1-insulin starting material. Once collected, the solution is rotovapped to remove acetonitrile and lyophilized to obtain pure BOC2(A1,B1)-Fmoc(B29)-insulin powder. Identity is verified by LC-MS (HT Laboratories, San Diego, Calif.) and site of conjugation determined by N-terminal sequencing (Western Analytical, St. Louis, Mo.).

c. $NH_2$—(B29)-BOC2(A1,B1)-Insulin

The Fmoc protecting group of the BOC2(A1,B1)-Fmoc (B29) is removed by dissolving the lyophilized powder obtained according to the previous step in 20% piperidine in dimethylformamide (DMF) for 30 minutes at 4 C followed by 10× superdilution in 25 mM HEPES pH 8.2 buffer containing 0.150 M NaCl. The pH is adjusted to between 7.0 and 8.0 using NaOH solution after which the material is passed through a Biogel P2 column to remove Fmoc, DMF, and any other contaminating salts. The $NH_2$—(B29)-BOC2(A1,B1)-insulin is lyophilized into a powder if needed or used directly in aqueous solution if desired.

Example 7

Insulin Conjugation with Multivalent Activated Esters in Organic Solvent

A framework containing N terminal activated esters is dissolved at 60 mM in 1 ml of anhydrous DMSO followed by the addition of 400 ul (excess) of triethylamine (TEA). The solution is stirred rapidly for 10 minutes at room temperature. In parallel, a 122 mM solution of ligand is prepared in an appropriate volume of anhydrous DMSO. Once dissolved, enough ligand solution is added dropwise over the course of ten minutes to provide a number of reactive equivalents equal to exactly the number of activated ester groups on the framework, N, minus one. For example, if there are N=3 activated ester groups on the framework, then $(1\times(3-1)\times 60$ mM/122 mM)=0.98 ml of ligand solution are added. If there are N=4 activated ester groups on the framework, then $(1\times(4-1)\times 60$ mM/122 mM)=1.5 ml of ligand solution are added, and so on. After the ligand solution is added, the solution is stirred for two hours at room temperature.

The insulin is then dissolved separately in 7.5 ml of anhydrous DMSO at a concentration of 8.1 mM. Once dissolved, the entire insulin solution is added over the course of one minute to the framework/DMSO/ligand/TEA solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the insulin molecule, framework, and ligand used. Once collected, the solution is rotovapped to remove acetonitrile and lyophilized to obtain pure conjugate whose identity may be verified by LC-MS (HT Laboratories, San Diego, Calif.).

Example 8

B29-Insulin Conjugates with Multivalent Saccharides Produced in Organic Solvent from Unprotected Insulin This example makes use of the fact that in unprotected insulin, the Lys-B29 epsilon-amino moiety is the most reactive amine, followed by the A1 and then the B1. Therefore, when unprotected insulin is used, the resulting conjugate should be predominantly substituted at the Lys-B29 position. Using the method described in Example 7 and recombinant human insulin (MW=5808 Da, Sigma Aldrich, St. Louis, Mo.), the following insulin conjugates were prepared using the TSAT-C6 activated ester framework purchased from Molecular Biosciences (Boulder, Colo.). The AEM and AETM were synthesized as described previously. The appropriately sized size exclusion medium was Biogel P2 (Bio-Rad Laboratories, Hercules, Calif.), and the appropriately sized ultrafiltration membrane molecular weight cutoff was 3 kDa.

| Conjugate | Framework | Framework MW | Ligand | AE-sugar MW | Purity (HPLC) | MW (LC-MS) | Sugar/Insulin |
|---|---|---|---|---|---|---|---|
| I-7: TSAT-C6-AEM-2 (B29) | TSAT-C6 | 822 | AEM | 223 | 93% | 6729 | 2.0 |
| I-6: TSAT-C6-AETM-2 (B29) | TSAT-C6 | 822 | AETM | 547 | 95% | 7378 | 2.0 |

According to N-terminal sequencing, approximately 85% of the AEM-containing framework was conjugated to insulin via the Lys-B29 and approximately 87% of the AETM-containing framework was conjugated to insulin via the Lys-B29.

Example 9

Insulin Conjugation with Multivalent Activated Esters in Aqueous Solvent

This example describes an alternative to the method described in Example 7 in which the reaction is performed in aqueous solvent instead of organic solvent.

The framework containing N terminal activated esters is dissolved at 60 mM in 6.25 ml of anhydrous DMSO followed by the addition of 2 ml (excess) of triethylamine (TEA). The solution is stirred rapidly for 10 minutes at room temperature. In parallel, a 448 mM solution of ligand is prepared in an appropriate volume of anhydrous DMSO. Once dissolved, enough ligand solution is added dropwise over the course of ten minutes to provide a number of reactive equivalents equal to 1.5 times the number of activated ester groups on the framework, N, minus one. For example, if there are N=3 activated ester groups on the framework, then (1.5×(3−1)×60 mM/448 mM)×6.25 ml=2.5 ml of ligand solution are added. If there are N=4 activated ester groups on the framework, then (1.5×(4−1)×60 mM/448 mM)×6.25 ml=3.8 ml of ligand solution are added, and so on. After the ligand solution is added, the solution is stirred for one hour at room temperature.

The insulin molecule is then dissolved separately at 17.2 mM in 2.67 ml of a 0.1M, pH 11 sodium carbonate buffer and the pH subsequently adjusted to 10.8 with 1.0N sodium hydroxide. Once dissolved, the entire framework/DMSO/ligand/TEA solution is added dropwise over the course of 75 minutes to the insulin/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC on a Waters SymmetryPrep C18, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the insulin molecule, framework, and ligand used. Once collected, the solution is rotovapped to remove acetonitrile and lyophilized to obtain pure conjugate whose identity may be verified by LC-MS (HT Laboratories, San Diego, Calif.).

Example 10

B29-AEM-2-Insulin Conjugate I-7 Synthesized in Aqueous Solvent from Unprotected Insulin This example makes use of the fact that in unprotected insulin, the Lys-B29 epsilon-amino moiety is the most reactive amine, followed by the A1 and then the B1. Therefore, when unprotected insulin is used, the resulting conjugate should be predominantly substituted at the Lys-B29 position. Using the method described in Example 9 and recombinant human insulin (MW=5808, Sigma Aldrich, St. Louis, Mo.), an AEM-2 insulin conjugate was prepared using the TSAT-C6 activated ester framework purchased from Molecular Biosciences (Boulder, Colo.). The AEM used as the insulin analog was synthesized as described previously. The appropriately sized size exclusion medium was Biogel P2 (Bio-Rad Laboratories, Hercules, Calif.), and the appropriately sized ultrafiltration membrane molecular weight cutoff was 3 kD. The final product (95% pure by HPLC) was found to have the desired MW of 6729 g/mol (LC-MS), representing a total of 2.0 AEM molecules conjugated per insulin, with greater than 85% of the conjugate molecules conjugated at the Lys-B29 site (N-terminal sequencing).

Example 11

Conjugates Prepared Using Natural Insulins from Other Species Such as Bovine and Porcine Insulins from other species which contain at least one reactive amine functionality (e.g., bovine and porcine insulin) may be coupled using any of the methods used to conjugate recombinant human insulin. Those skilled in the art will appreciate that the molecular weights of the resulting conjugates made from bovine or porcine insulins will differ from those made from recombinant human insulin by the amounts listed in the following table.

| Type of Insulin | Molecular Weight (g/mol) | Difference in MW human insulin (g/mol) |
|---|---|---|
| Human insulin | 5808 | — |
| Porcine insulin | 5778 | −30 |
| Bovine insulin | 5733 | −75 |

Those skilled in the art will also appreciate that the resulting conjugates made from bovine or porcine insulin may have chromatographic peak retention times that differ slightly from those conjugates made from human insulin, due to the small differences in structures between the insulins.

Example 12

Conjugates Prepared with Insulin Analogs Such as Lispro, Aspart, Glulysine, Glargine, and Detemir All known insulin analogs which contain at least one reactive amine functionality (e.g., lispro, aspart, glulisine, glargine, and detemir) may be coupled using any of the methods used to conjugate recombinant human insulin. Those skilled in the art will appreciate that the molecular weights of the resulting conjugates made from insulin analogs will differ from those made from recombinant human insulin by the amounts listed in the following table.

| Type of Insulin | Molecular Weight (g/mol) | Difference in MW human insulin (g/mol) |
|---|---|---|
| Human insulin | 5808 | — |
| Insulin lispro | 5808 | — |
| Insulin aspart | 5832 | +24 |
| Insulin glulisine | 5823 | +15 |
| Insulin glargine | 6063 | +255 |
| Insulin detemir | 5913 | +105 |

Those skilled in the art will also appreciate that the resulting conjugates made from insulin analogs may have chromatographic peak retention times that differ slightly from those conjugates made from human insulin, due to the small differences in structures between the insulins.

Example 13

Figure 3:
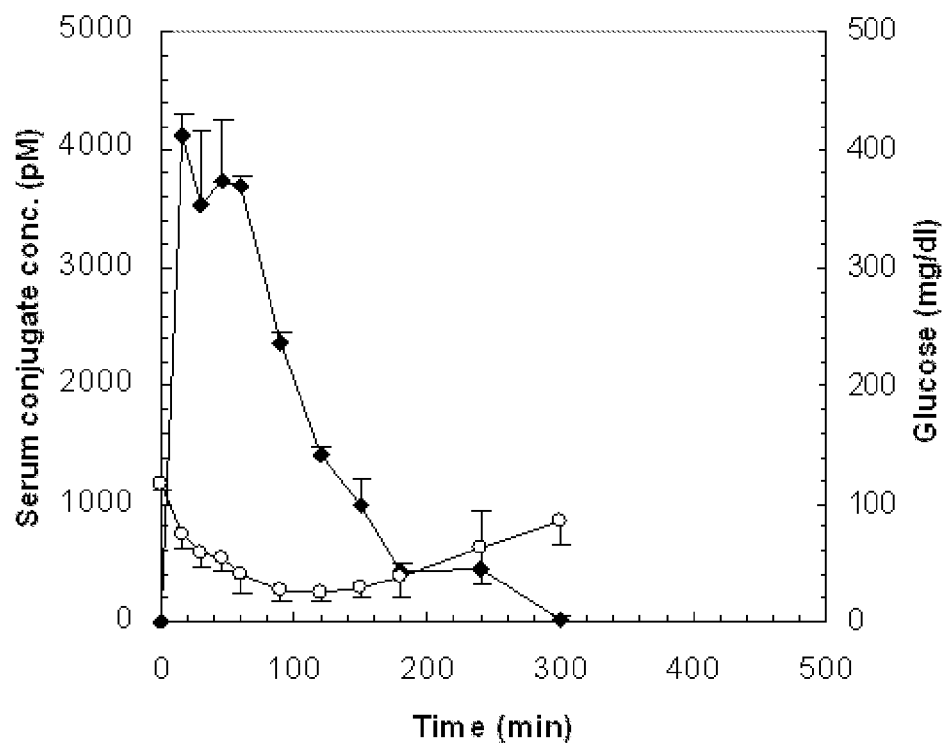
FIG. 3: Plot of (♦) serum insulin and (○) blood glucose levels following subcutaneous injection in non-diabetic, male SD rats at time 0 with conjugate I-7 (5 U/kg). Data represents the average and standard deviation for n=3 rats.

PK and Bioactivity of a B29-Substituted Version of the AEM-2-TSAT-C6-Insulin Conjugate This example describes the serum insulin and blood glucose depression profiles obtained for a subcutaneously administered exemplary conjugate. The exemplary conjugate, I-7 in FIG. 2, was synthesized using TSAT-C6 as the framework, AEM as the ligand, and recombinant human insulin to produce a B29-substituted conjugate. In this case, the conjugate was injected at 5 U/kg behind the neck of fasted normal non-diabetic rats (Male Sprague-Dawley, 400-500 g, n=3). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 3, the B29-substituted conjugate is rapidly absorbed into and eliminated from serum following a subcutaneous injection.

Example 14

Effect of a-MM on PK and Bioactivity as a Function of Ligand Affinity

In this example, the TSAT-C6 framework was used and the following conjugates were synthesized according to the methods described in Example 9 (note glucosamine-HCl or GA-HCl was purchased from Sigma-Aldrich (St. Louis, Mo.) and used without further purification):

| Conjugate | Framework | Framework MW | Ligand | AE-sugar MW | Purity (HPLC) | MW (LC-MS) | Sugar/Insulin |
|---|---|---|---|---|---|---|---|
| I-7: TSAT-C6-AEM-2 (B29) | TSAT-C6 | 822 | AEM | 223 | 95% | 6729 | 2.0 |
| I-5: TSAT-C6-GA-2 (B29) | TSAT-C6 | 822 | GA-HCl | 216 | 95% | 6641 | 2.0 |

According to N-terminal sequencing, approximately 90% of each saccharide-containing framework was conjugated to insulin via the Lys-B29. TSAT-C6-AEM-2 (B29) and TSAT-C6-GA-2 (B29) are shown in FIG. 2 as conjugates I-7 and I-5, respectively.

Conjugates (5 U/kg) were injected behind the neck of fasted normal non-diabetic rats (Male Sprague-Dawley, 400-500 gm, n=3). After a 15 minute delay a 4 g/kg dose of a-MM was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (ISO Insulin ELISA, Mercodia, Uppsala, Sweden). A control was performed by injecting saline instead of a-MM after 15 minutes.

Figure 4:
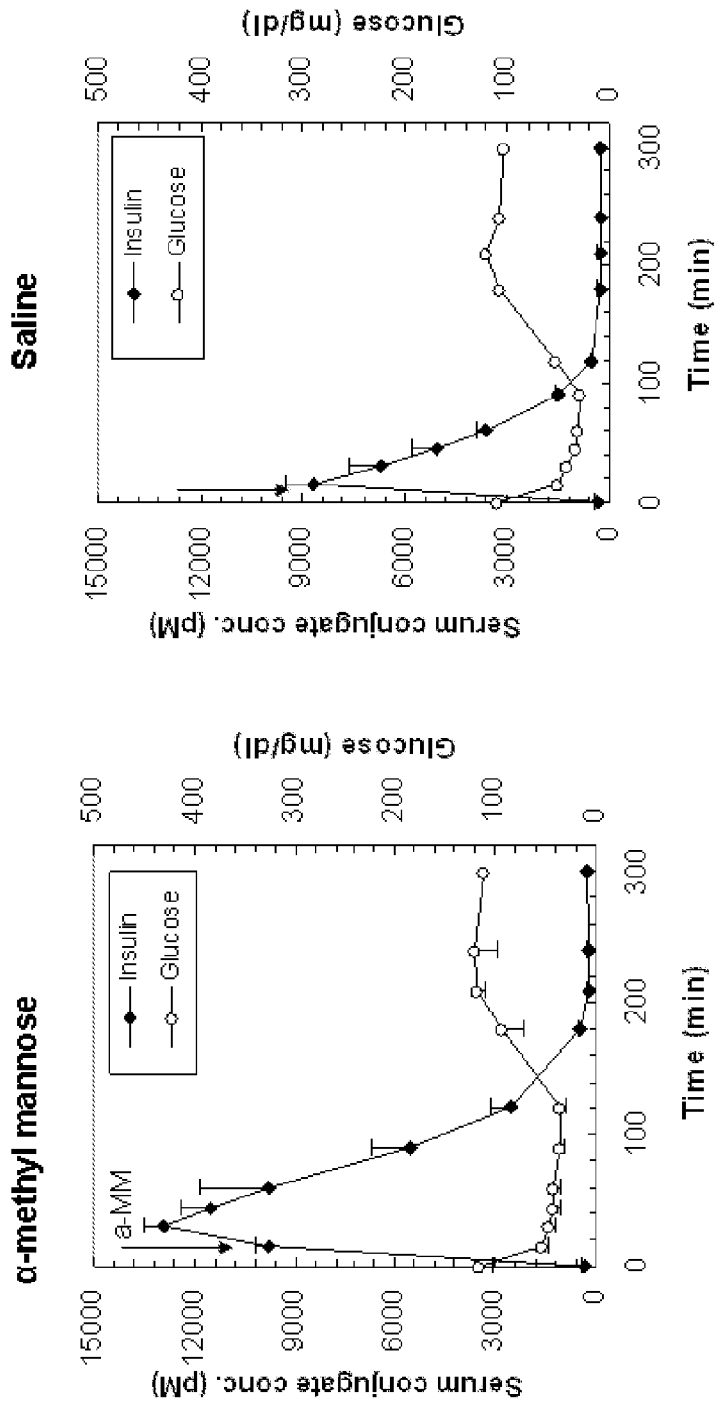
FIG. 4: Plot of serum insulin and blood glucose levels following subcutaneous injection in non-diabetic, male SD rats (n=3) at time 0 with conjugate I-7 followed by IP injection of alpha-methyl mannose (left) or saline (right) after 15 minutes.
Figure 5:
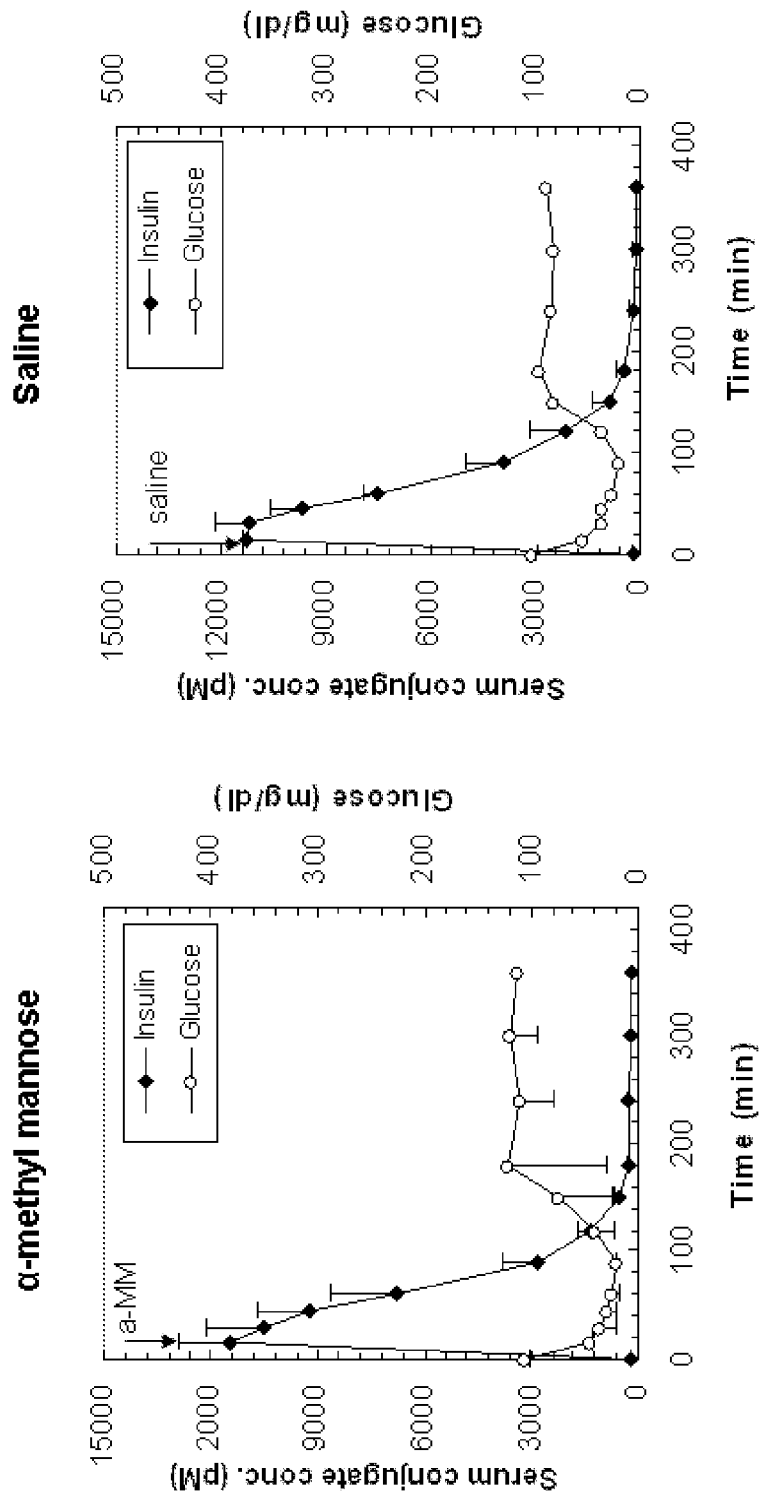
FIG. 5: Plot of serum insulin and blood glucose levels following subcutaneous injection in non-diabetic, male SD rats (n=3) at time 0 with conjugate I-5 followed by IP injection of alpha-methyl mannose (left) or saline (right) after 15 minutes.

FIGS. 4 and 5 show the results obtained when a-MM was administered by IP injection 15 minutes after the sub-Q injection of I-7 and I-5, respectively. As shown, the increase in PK/PD profile that resulted from injection of a-MM was very significant ($p<0.05$) for conjugate I-7 when compared to the saline injection control group. The I-5 conjugate profile was unaffected by the a-MM injection.

Example 15

Effect of a-MM on PK and Bioactivity as a Function of Ligand Valency

In this example, we set out to determine the pharmacokinetic and pharmacodynamic behavior of conjugates to which an increasing number of exemplary saccharide ligands have been covalently attached. All conjugates were synthesized according to the methods described in Example 9 using the frameworks and saccharide ligands specified below:

| Conjugate | Framework | Framework MW | Ligand | AE-sugar MW | Purity (HPLC) | MW (LC-MS) | Sugar/Insulin |
|---|---|---|---|---|---|---|---|
| I-8: DSS-AEM-1 (B29) | DSS | 368 | AEM | 223 | >95% | 6168 | 1.0 |
| I-9: TSPE-AEM-3 (B29) | TSPE | 813 | AEM | 223 | >95% | 6829 | 3.0 |
| I-10: DSS-AETM-1 (B29) | DSS | 368 | AETM | 547 | >95% | 6491 | 1.0 |
| I-11: TSPE-AETM-3 (B29) | TSPE | 813 | AETM | 547 | >95% | 7800 | 3.0 |

According to N-terminal sequencing, approximately 90% of each saccharide-containing framework was conjugated to insulin via the Lys-B29. The conjugates are shown in FIG. 2 as I-8, I-9, I-10, and I-11.

The same type of experiment described in Example 14 was repeated for the conjugates described in the table above. In each case, the same dose of conjugate (5 U/kg) was injected behind the neck of fasted normal non-diabetic rats (Male Sprague-Dawley, 400-500 gm, n=3). After a 15 minute delay a 4 g/kg dose of a-MM was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (ISO Insulin ELISA, Mercodia, Uppsala, Sweden). A control was performed by injecting saline instead of a-MM after 15 minutes.

Figure 6:
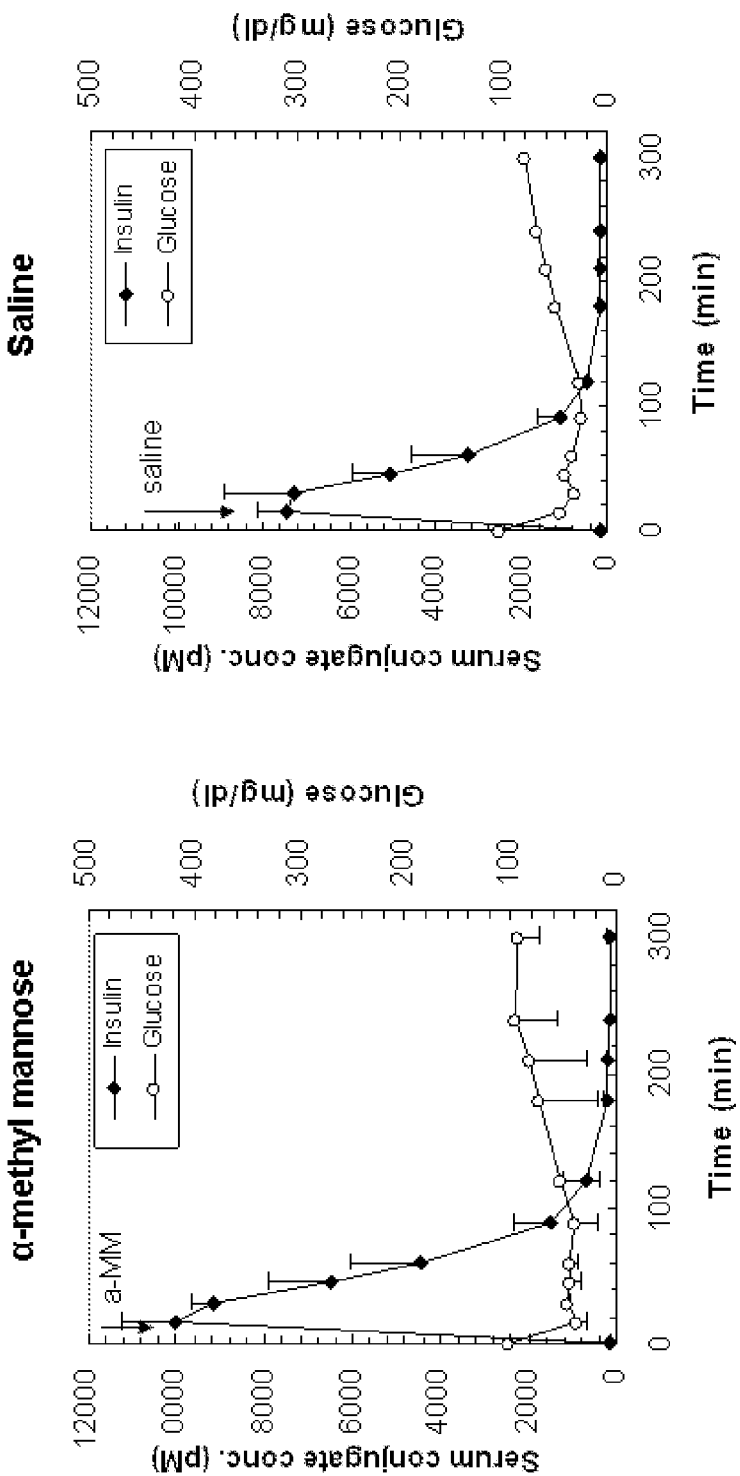
FIG. 6: Plot of serum insulin and blood glucose levels following subcutaneous injection in non-diabetic, male SD rats (n=3) at time 0 with conjugate I-8 followed by IP injection of alpha-methyl mannose (left) or saline (right) after 15 minutes.
Figure 7:
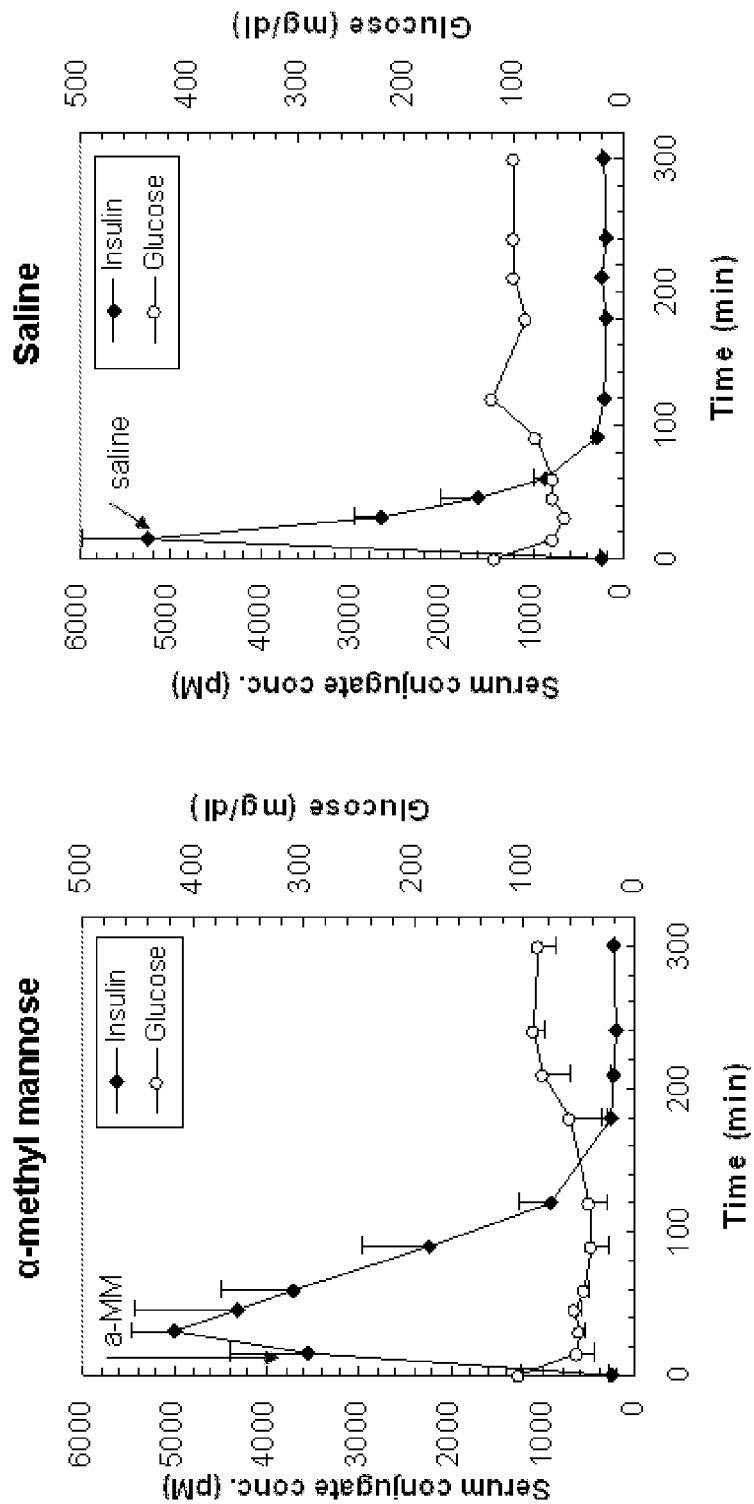
FIG. 7: Plot of serum insulin and blood glucose levels following subcutaneous injection in non-diabetic, male SD rats (n=3) at time 0 with conjugate I-9 followed by IP injection of alpha-methyl mannose (left) or saline (right) after 15 minutes.

FIGS. 6 and 7 show the results obtained when a-MM was administered by IP injection 15 minutes after the sub-Q injection of I-8 and I-9, respectively. As shown, the increase in PK/PD profile that resulted from injection of a-MM was very significant ($p<0.05$) for I-9 and less so for I-8 when compared to the saline injection control group.

Figure 8:
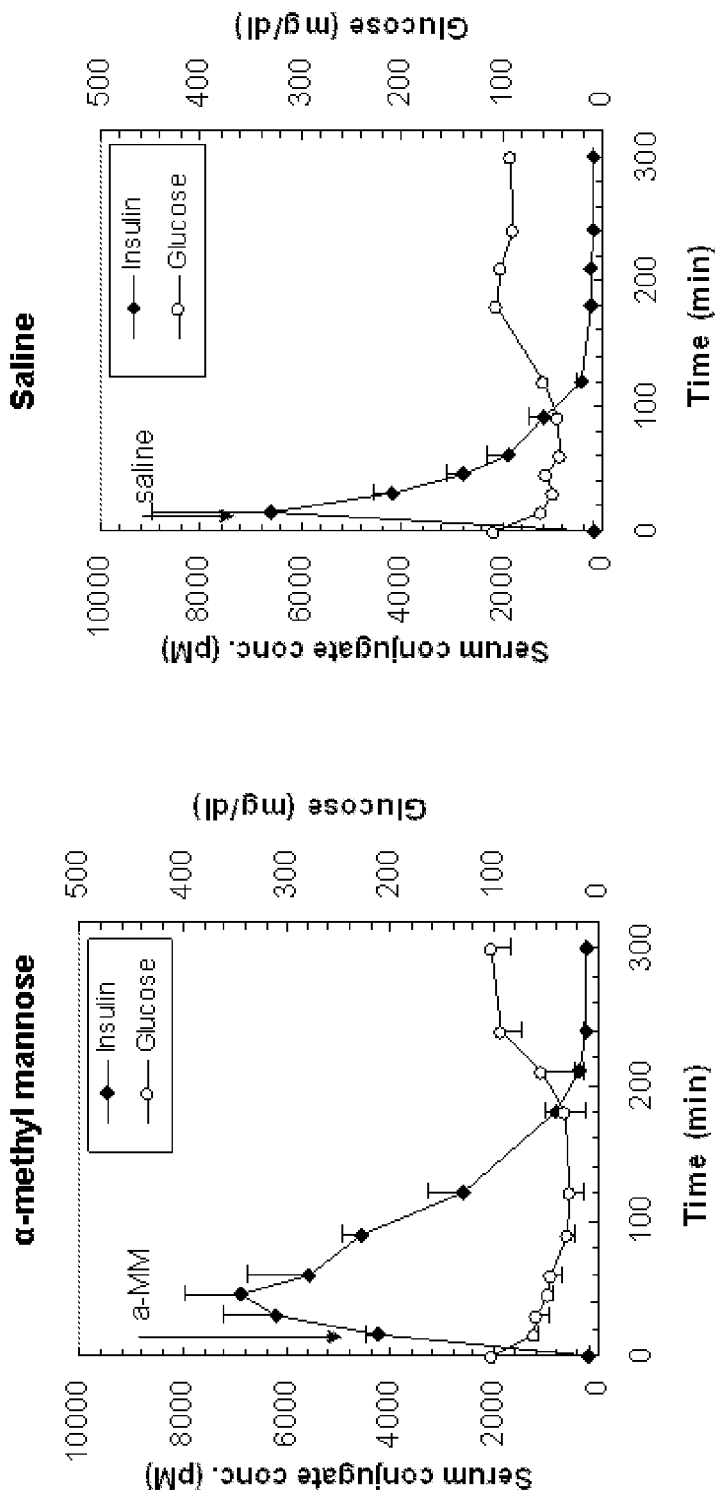
FIG. 8: Plot of serum insulin and blood glucose levels following subcutaneous injection in non-diabetic, male SD rats (n=3) at time 0 with conjugate I-10 followed by IP injection of alpha-methyl mannose (left) or saline (right) after 15 minutes.
Figure 9:
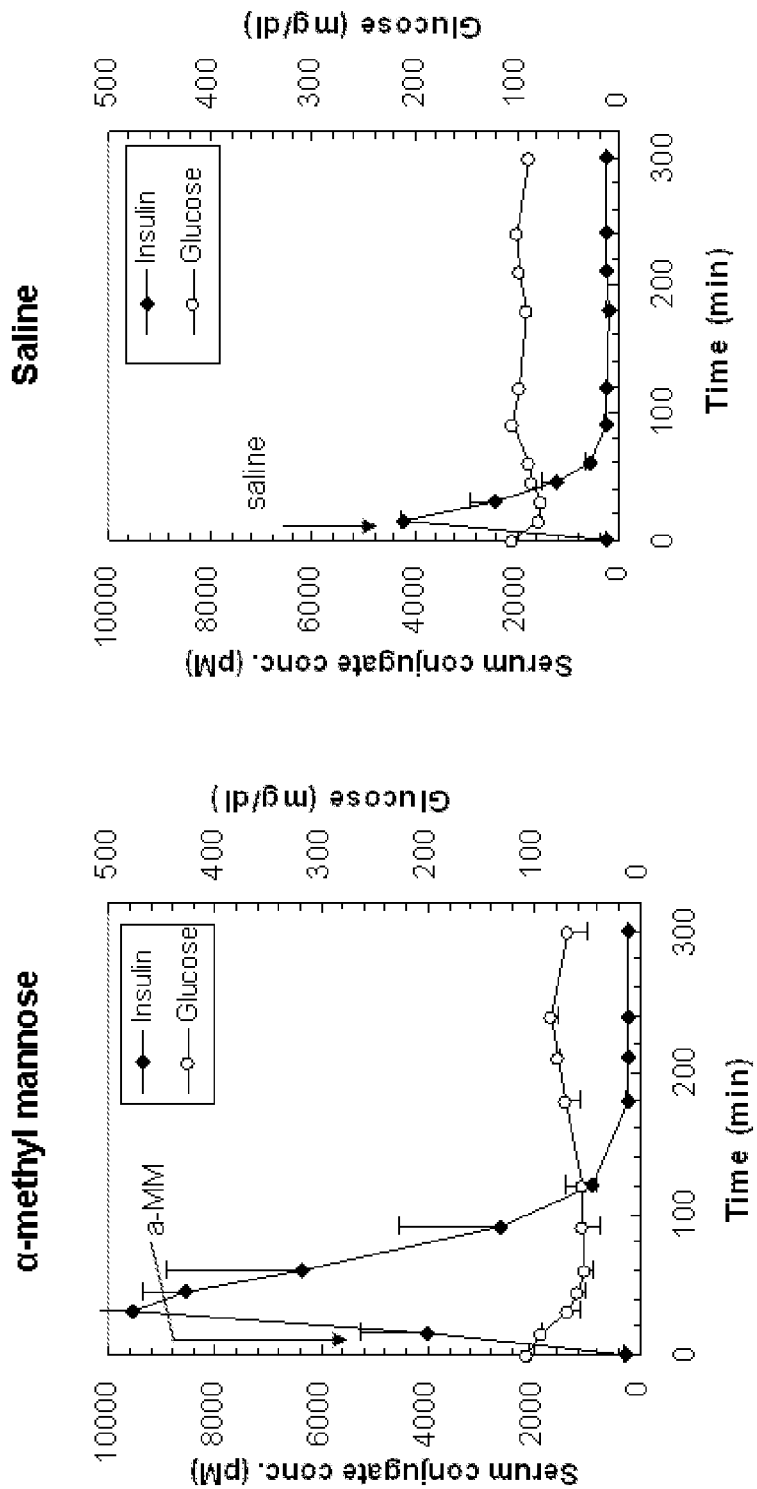
FIG. 9: Plot of serum insulin and blood glucose levels following subcutaneous injection in non-diabetic, male SD rats (n=3) at time 0 with conjugate I-11 followed by IP injection of alpha-methyl mannose (left) or saline (right) after 15 minutes.

FIGS. 8 and 9 show the results obtained when a-MM was administered by IP injection 15 minutes after the sub-Q injection of I-10 and I-11, respectively. As shown, the increase in PK/PD profile that resulted from injection of a-MM was very significant ($p<0.05$) for I-11 and slightly less so for I-10 when compared to the saline injection control group.

Example 16

In Vivo Half Life/Elimination Rate Comparison

The following experiments were conducted using exemplary conjugates to determine the rate at which they were cleared from serum in vivo versus unconjugated insulin. All conjugates used in this study were synthesized according to the general methods described in Example 9.

In each case the soluble conjugate was dosed at 0.4 mg conjugate/kg body weight into dual jugular vein cannulated male Sprague-Dawley rats (Taconic, JV/JV, 350-400 g, n=3). A sterile conjugate solution or control insulin was injected intravenously via one JV cannula, followed immediately by a chase solution of heparin-saline to ensure that all of the conjugate dose was administered into the animal. The second cannula was used to collect blood samples at t=0 (pre-dose), and at 1, 2, 4, 8, 15, 30, 60, 90, 120, and 180 minutes post-dose.

Blood glucose values were measured using commercially available test strips (Precision Xtra, Abbott Laboratories, Abbott Park, Ill.). In addition, blood from each timepoint was centrifuged at 4 C to collect the serum. Serum insulin or serum conjugate concentrations were subsequently measured with a commercially available ELISA kit (Iso-Insulin ELISA, Mercodia, Uppsala, Sweden).

Figure 10:
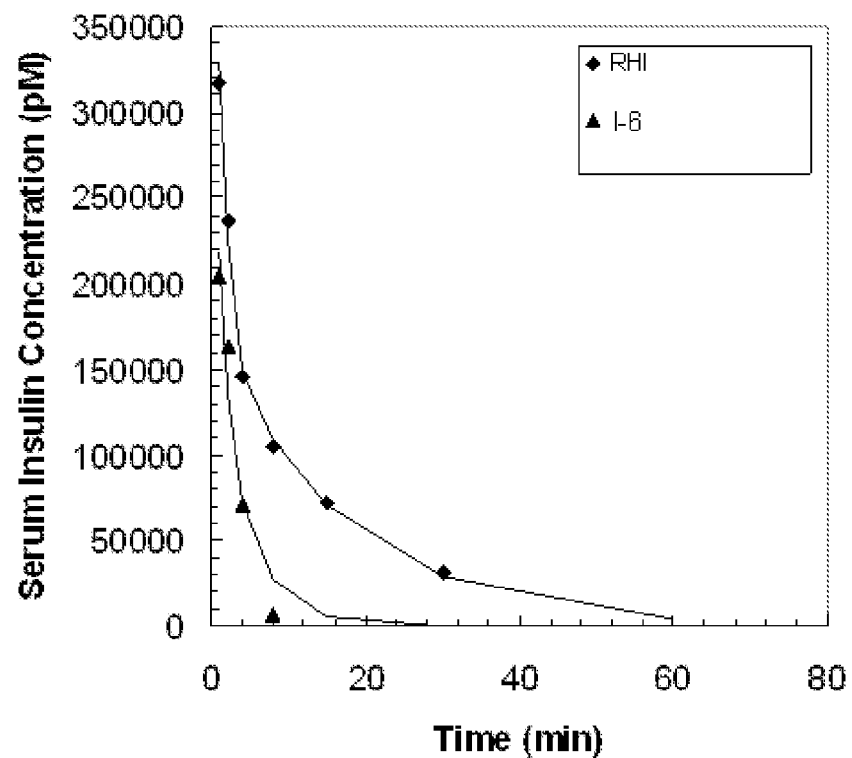
FIG. 10: Plot of serum insulin concentration as a function of time for 0.4 mg/kg i.v. injections of (♦) RHI and (▲) conjugate I-6 into non-diabetic, male SD rats (n=3 per group). Data (average of n=3) is fit using a two-compartment bi-exponential model.

FIG. 10 shows the serum concentration of either RHI or TSAT-C6-AETM-2 conjugate, shown as I-6 in FIG. 2, as a function of time following the intravenous injection. Clearly, I-6 is eliminated much more rapidly from serum than is RHI. The data is best fit using a two-compartment bi-exponential model with the following general formula: $C(t)=A_o \text{EXP}(-at)+B_o \text{EXP}(-bt)$ where t is time, C(t) is the concentration in serum as a function of time, $A_o$ is the first compartment concentration constant, a is the first compartment exponential time constant, $B_o$ is the second compartment concentration constant, and b is the second compartment exponential time constant. The elimination half-lives (in minutes) associated with each compartment are $t\frac{1}{2}(a)=0.693/a$ and $t\frac{1}{2}(b)=0.693/b$. In FIG. 10, for RHI the $t\frac{1}{2}(a)=0.76$ and $t\frac{1}{2}(b)=11.46$ and for I-6 the $t\frac{1}{2}(a)=0.47$ and $t\frac{1}{2}(b)=2.87$. In other words, the $t\frac{1}{2}(b)$ for I-6 is about four times shorter than the $t\frac{1}{2}(b)$ for RHI.

The following table summarizes the $t\frac{1}{2}$ parameters for a number of conjugates tested using exactly the same procedure described above (structures are shown in FIG. 2):

| Formulation | $t\frac{1}{2}$ (a) | $t\frac{1}{2}$ (b) | Ratio to RHI $t\frac{1}{2}$ (a) | Ratio to RHI $t\frac{1}{2}$ (b) |
|---|---|---|---|---|
| RHI | 0.76 | 11.46 | 1.00 | 1.00 |
| I-5: TSAT-C6-GA-2 | 0.81 | 12.02 | 1.07 | 1.05 |
| I-8: DSS-AEM-1 | 0.90 | 9.61 | 1.18 | 0.84 |
| I-7: TSAT-C6-AEM-2 | 0.45 | 2.77 | 0.60 | 0.24 |
| I-9: TSPE-AEM-3 | 0.66 | 2.62 | 0.87 | 0.23 |
| I-10: DSS-AETM-1 | 0.82 | 4.48 | 1.08 | 0.39 |
| I-6: TSAT-C6-AETM-2 | 0.47 | 2.87 | 0.62 | 0.25 |
| I-11: TSPE-AETM-3 | 0.22 | 1.33 | 0.29 | 0.12 |

This data is consistent with the hypothesis that the exemplary conjugates are eliminated from serum more rapidly than unconjugated insulin, the extent of which is governed by the affinity of the particular conjugate for the endogenous lectin and the number of ligands substituted per conjugate.

Example 17

In Vivo Half Life/Elimination Rate Under Glucose Infusion

In this example, it was further hypothesized that the clearance rate of exemplary conjugates could be inhibited by the presence of physiological concentrations of glucose. In order to determine the rate at which the conjugates were cleared from serum in vivo under hyperglycemic conditions, the following experiment was conducted. In each case, I-7 was dosed at 0.4 mg conjugate/kg body weight into dual jugular vein cannulated male Sprague-Dawley rats (Taconic, JV/JV, 350-400 g, n=3).

One hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials $(C(t)=a\exp(-k_a t)+b\exp(-k_b t))$ according to the two-compartment model, where $t\frac{1}{2}(a)=(\ln 2)/k_a$ and $t\frac{1}{2}(b)=(\ln 2)/k_b$. The following table summarizes the $t\frac{1}{2}$ parameters for I-7 with and without the glucose infusion along with those obtained for RHI from Example 16:

| Infusion | Formulation | $t\frac{1}{2}$ (a) | $t\frac{1}{2}$ (b) | Ratio to RHI $t\frac{1}{2}$ (a) | Ratio to RHI $t\frac{1}{2}$ (b) |
|---|---|---|---|---|---|
| None | RHI | 0.76 | 11.46 | 1.00 | 1.00 |
| Saline | TSAT-C6-AEM-2 (I-7) | 0.45 | 2.77 | 0.60 | 0.24 |
| Glucose (400 mg/dl) | TSAT-C6-AEM-2 (I-7) | 0.64 | 5.11 | 0.84 | 0.45 |

We can conclude from these data that glucose is able to inhibit the accelerated serum elimination for this conjugate thereby doubling the Phase b elimination half life from 2.77 to 5.11 minutes.

Example 18

In Vivo Half Life/Elimination Rate Under a-MM Infusion

In this example, it was further hypothesized that the clearance rate of insulin-conjugates could be inhibited by the presence of arbitrarily high concentrations of inhibitory saccharides other than glucose, such as α-methyl-mannose (a-MM). In order to determine the rate at which exemplary conjugates were cleared from serum in vivo in the presence of a-MM, the following experiment was conducted. In each case the soluble conjugate was dosed at 0.4 mg conjugate/kg body weight into dual jugular vein cannulated male Sprague-Dawley rats (Taconic, JV/JV, 350-400 g, n=3).

One hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

In addition, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials $(C(t)=a\exp(-k_a t)+b\exp(-k_b t))$ according to the two-compartment model, where $t\frac{1}{2}(a)=(\ln 2)/k_a$ and $t\frac{1}{2}(b)=(\ln 2)/k_b$. The following table summarizes the $t\frac{1}{2}$ parameters for the TSAT-C6-AEM-2 conjugate with and without the a-MM infusion along with those obtained with glucose infusion from Example 17 and those obtained for RHI with no saccharide infusion from Example 16:

| Infusion | Formulation | $t\frac{1}{2}$ (a) | $t\frac{1}{2}$ (b) | Ratio to RHI $t\frac{1}{2}$ (a) | Ratio to RHI $t\frac{1}{2}$ (b) |
|---|---|---|---|---|---|
| None | RHI | 0.76 | 11.46 | 1.00 | 1.00 |
| Saline | TSAT-C6-AEM-2 (I-7) | 0.45 | 2.77 | 0.60 | 0.24 |
| a-MM | TSAT-C6-AEM-2 (I-7) | 0.92 | 10.09 | 1.21 | 0.88 |
| Glucose (400 mg/dl) | TSAT-C6-AEM-2 (I-7) | 0.64 | 5.11 | 0.84 | 0.45 |

We can conclude from these data that not only does a-MM inhibit the accelerated serum elimination for this conjugate, it does so to an even greater extent than does glucose. In this case, the Phase b elimination half life nearly quadruples from 2.77 to 10.09 minutes.

Example 19

Long Acting Insulin Conjugates Using Protamine, Zinc, and Other Excipients

In order to generate long acting conjugates, we prepared PZI (protamine zinc insulin) formulations from B29-substituted conjugates prepared based on the methods of Example 9. The excipients used in these formulations comprise protamine, zinc, m-cresol, and salt all of which are obtained commercially from Sigma-Aldrich (St. Louis, Mo.). The concentrations of these components may be varied in order to obtain an optimally flat, sustained absorption rate. In addition, in some cases it was found that the addition of a small amount of unmodified insulin helped stabilize the formulation. In these cases, the concentration of unmodified insulin contained in the sample was varied to obtain an optimally flat, sustained absorption rate. In all formulations tested, the following recipe was used:

| Component | Variable | Volume (ml) |
|---|---|---|
| Conjugate solution at 2.7 mg/ml | % unmodified insulin content (M/M) | 1.000 |
| 250 mM HEPES buffered saline | NaCl concentration (M) | 0.111 |

| Component | Variable | Volume (ml) |
|---|---|---|
| Zinc acetate solution | Zinc concentration (mg/ml) | 0.124 |
| Cresol solution in water | v/v % | 0.159 |
| pH 7.2 Protamine solution in 25 mM HEPES buffered saline | Protamine concentration (mg/ml) | 4 × 0.194 aliquots |

Unless otherwise specified, once the formulations were prepared after addition of the components in the order described in the table above, they were gently mixed for 30 minutes prior to in vivo testing.

To test the sustained release profile for a given formulation as well as the glucose-responsive PK profile, the following experiment was conducted. The formulation was injected at a predetermined dose (~15 U/kg in most cases unless otherwise specified) behind the neck of fasted normal non-diabetic rats (Male Sprague-Dawley, 400-500 gm, n=3). After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden). According to the manufacturer's assay specifications, the Iso-Insulin ELISA is 71% cross-reactive with rat insulin. The serum samples were diluted by 10× in order to minimize the amount of endogenous rat insulin detected in each sample but the possibility of rat insulin detection could not be completely ruled out. Therefore, the results are generally reported as "measured insulin," which can consist of some amount of endogenous rat insulin in addition to the conjugate or RHI, depending on the experiment. Nevertheless, all samples collected in each of the following examples were treated identically and can be directly compared for differences in performance.

Example 20

Effect of Protamine Concentration on Long Acting Insulin Conjugate Performance

The purpose of this example was to demonstrate the effect of protamine concentration on the time action and glucose-responsive PK profile of an exemplary conjugate. In this example I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration (mg/ml) = see below | 0.124 |
| Cresol solution in water | 3% v/v | 0.159 |
| pH 7.2 Protamine solution in 25 mM HEPES buffered saline | Protamine concentration (mg/ml) = see below | 4 × 0.194 aliquots |

| Formulation | Zinc concentration (mg/ml) | Protamine concentration (mg/ml) |
|---|---|---|
| 1xP-1xZ | 1.15 | 1.25 |
| 4xP-4xZ | 4.60 | 5.00 |
| 10xP-4xZ | 4.60 | 12.50 |

Figure 11:
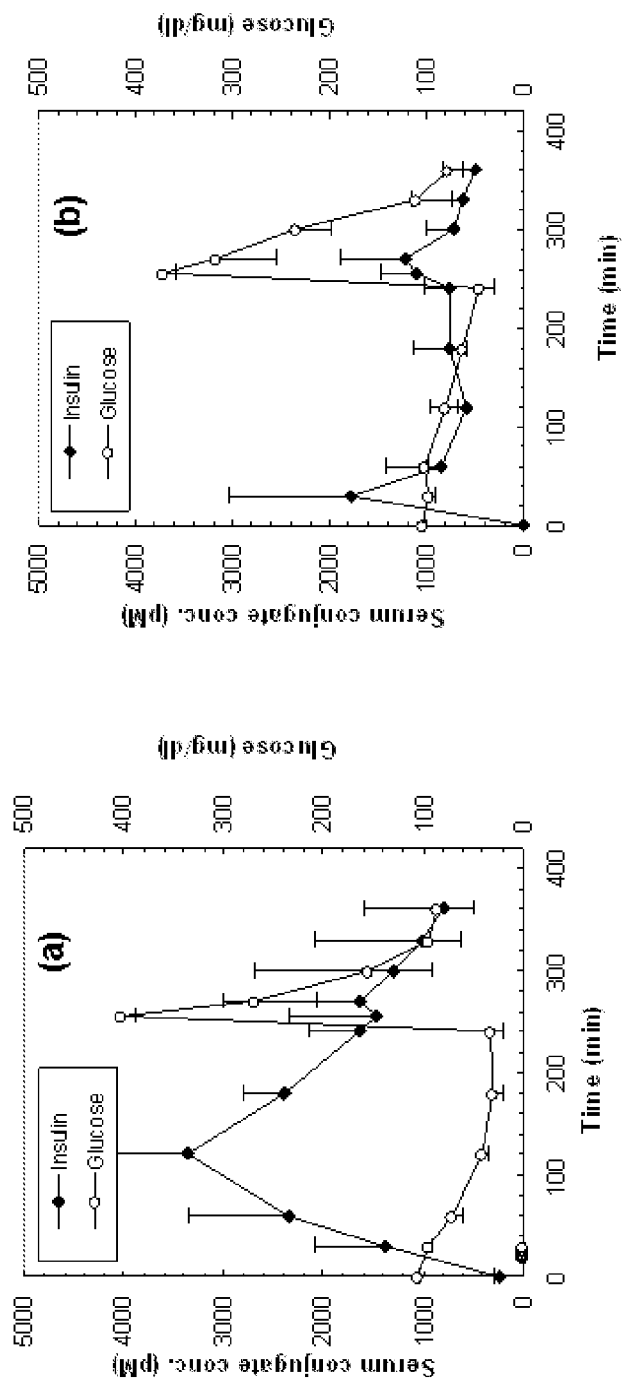
FIG. 11: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared as described in Example 20: (a) 1×P–1×Z, (b) 4×P–4×Z, and (c) 10×P–4×Z.
Figure 11:
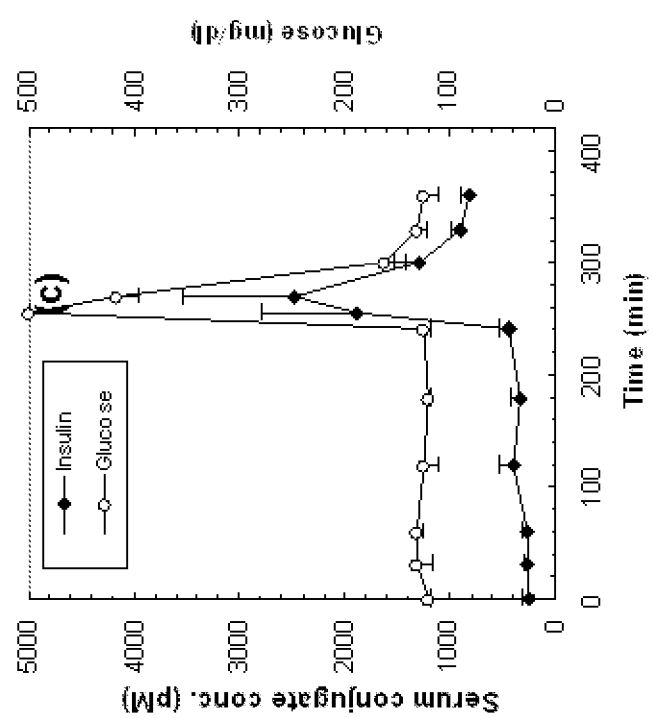
Figure 12:
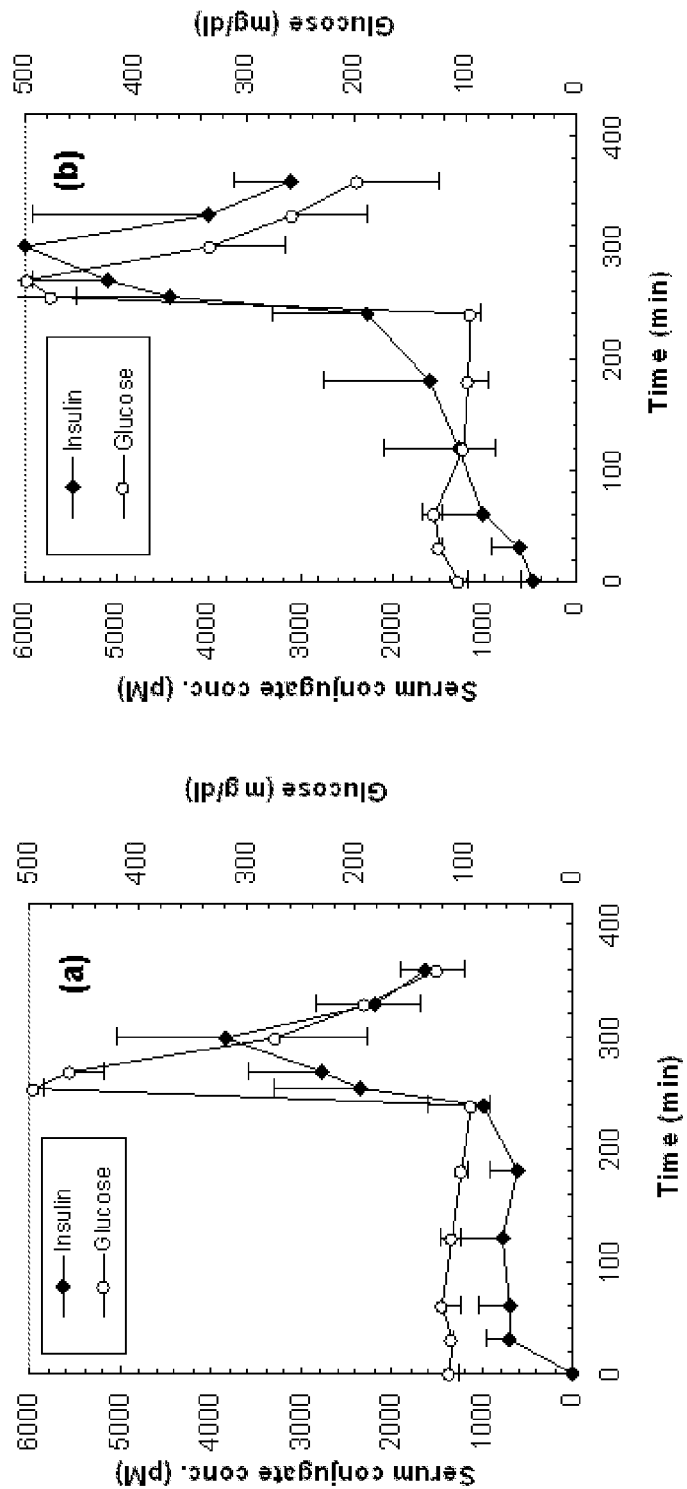
FIG. 12: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared as described in Example 21: (a) 4×P–1×Z and (b) 4×P–2×Z.
Figure 13:
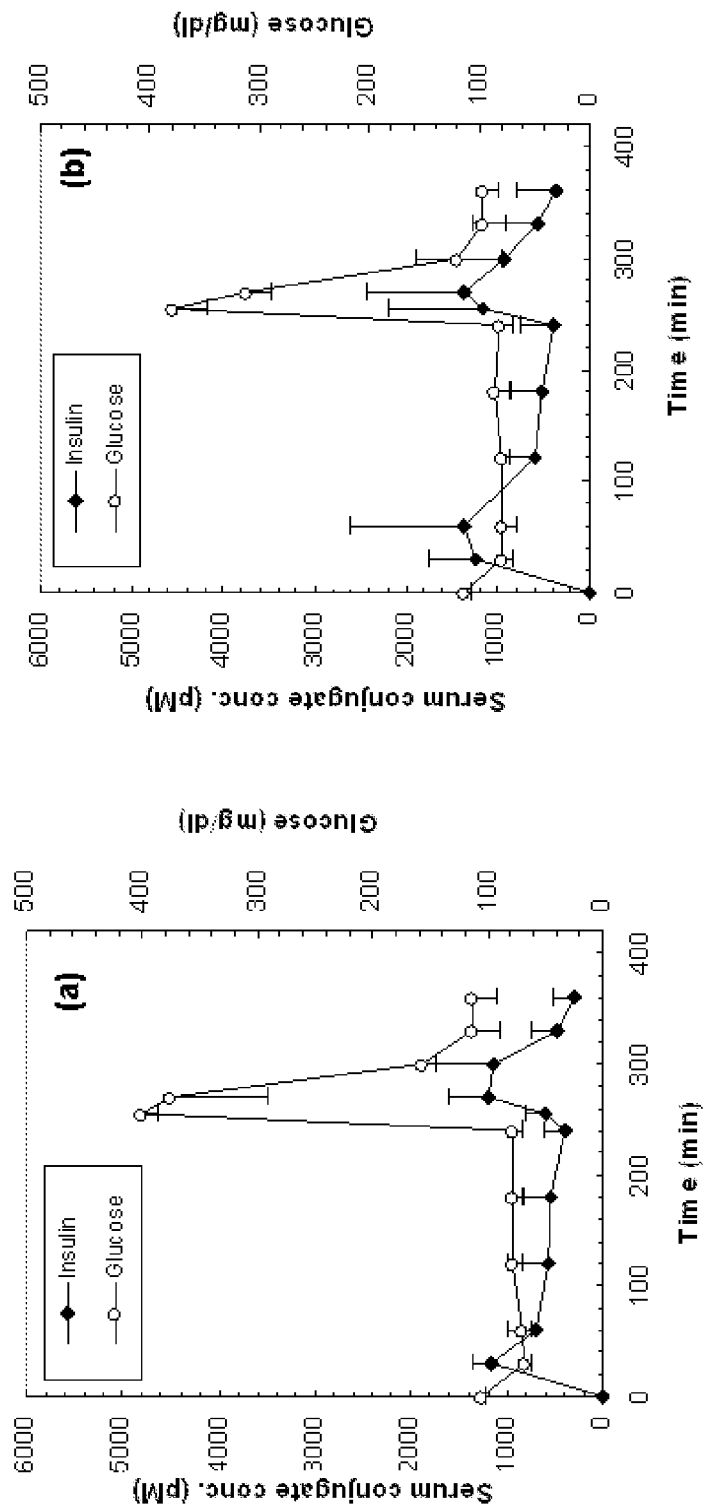
FIG. 13: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared as described in Example 21: (a) 10×P–1×Z and (b) 10×P–2×Z.

The four hour IP glucose injection (4 g/kg) experiments were performed by dosing 15 U/kg (body weight in grams/1.87=microliters of injection volume) of each of the three formulations described above. The results shown in FIG. 11a-c demonstrate that as the protamine concentration in the formulation increases, the more protracted the resulting formulation and the more pronounced the—measured increase in serum insulin profile after the four hour glucose injection. The 1xP-1xZ formulation releases a significant portion of the insulin conjugate payload over a short period of time immediately following the injection such that very little signal is detected after the IP glucose challenge. On the other hand, the 10xP-4xZ formulation releases a low basal amount of insulin over the first four hours with no hypoglycemia and subsequently attains >4× increase in measured insulin concentration immediately following the IP glucose injection.

Example 21

Effect of Zinc Concentration on Long Acting Insulin Conjugate Performance

The purpose of this example was to demonstrate the effect of zinc concentration on the formulation stability, time action and glucose-responsive PK profile of an exemplary conjugate. In this example I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration (mg/ml) = see below | 0.124 |
| Cresol solution in water | 3% v/v | 0.159 |
| pH 7.2 Protamine solution in 25 mM HEPES buffered saline | Protamine concentration (mg/ml) = see below | 4 × 0.194 aliquots |

| Formulation | Zinc concentration (mg/ml) | Protamine concentration (mg/ml) |
|---|---|---|
| 4xP-1xZ | 1.15 | 5.00 |
| 4xP-2xZ | 2.30 | 5.00 |
| 10xP-1xZ | 1.15 | 12.5 |
| 10xP-2xZ | 2.30 | 12.5 |

The four hour IP glucose injection (4 g/kg) experiments were performed by dosing 15 U/kg (body weight in grams/1.87=microliters of injection volume) of each of the four formulations described above. The results shown in FIGS. 12a-b and 13a-b demonstrate that within experimental error, the concentration of zinc does not have a significant effect on the overall sustained release nature of the formulation or the glucose-responsive profile. In all cases, a statistically significant increase in measured insulin concentration was observed following the IP glucose injection. As demonstrated in Example 20, the higher protamine (10×P) formulations release less conjugate over time than the lower protamine (4×P) formulations regardless of the zinc concentration. However, when the formulations were left at room temperature for greater than 24 hours, both 10×P formulations transformed from an easily dispersible particulate solution into a sticky, agglomerated, two-phase solution. This did not happen with the corresponding 10×P–4×Z formulation. Similarly, the 4×P–1×Z formulation was found to transform the same way as the 10×P–1×Z formulation whereas the 4×P–2×Z was relatively stable at room temperature for weeks. Therefore, the zinc concentration for a given protamine concentration can be adjusted to prepare easily dispersible formulations that are stable over long periods of time.

Example 22

Effect of m-cresol Concentration on Long Acting Insulin Conjugate Performance

The purpose of this example was to demonstrate the effect of m-cresol concentration on the time action and glucose-responsive PK profile of an exemplary conjugate. In this example I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | v/v % = see below | 0.159 |
| pH 7.2 Protamine solution in 25 mM HEPES buffered saline | Protamine concentration = 12.5 mg/ml | 4 × 0.194 aliquots |

| Formulation | Cresol concentration |
|---|---|
| No cresol | 0 |
| 4× cresol | 12% v/v |

Figure 14:
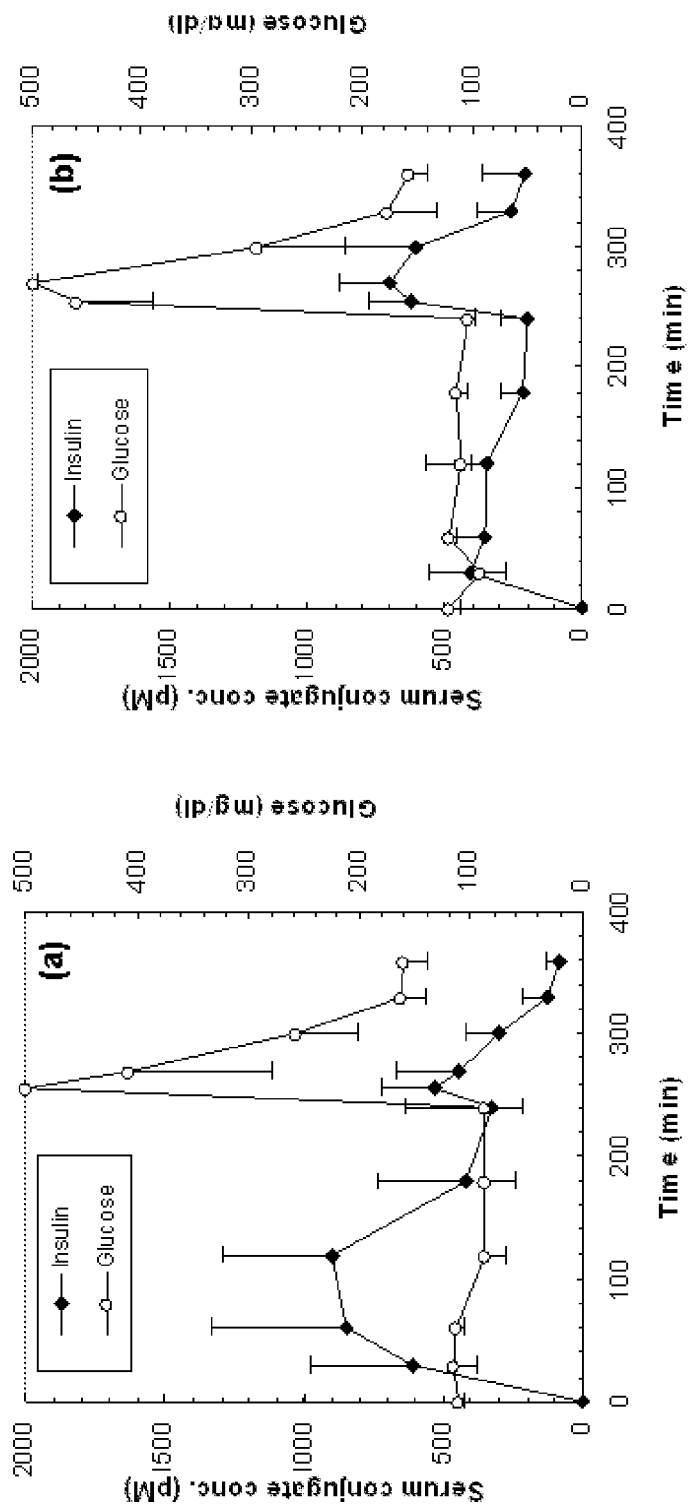
FIG. 14: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared as described in Example 22: (a) no cresol and (b) 4× cresol.

The four hour IP glucose injection (4 g/kg) experiments were performed by dosing 15 U/kg (body weight in grams/1.87=microliters of injection volume) of the two formulations described above. The results shown in FIG. 14a-b demonstrate that the presence of m-cresol maintains a more protracted formulation. The no cresol formulation releases a significant portion of the insulin conjugate payload over a short period of time immediately following the injection such that very little increase in measured insulin concentration is observed when challenged with IP glucose. On the other hand, the 4× cresol formulation releases a low basal amount of insulin over the first four hours with no hypoglycemia and subsequently attains a 3-4× increase in measured insulin concentration immediately following the IP glucose injection.

Example 23

Effect of Salt/Isotonic Agent Concentration on Long Acting Insulin Conjugate Performance The purpose of this example was to demonstrate the effect of salt concentration and choice of isotonic agent on the time action and glucose-responsive PK profile of an exemplary conjugate. In this example I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | unmodified insulin = 16.7% | 1.000 |
| 250 mM HEPES buffered saline | NaCl or glycerol concentration (M) = see below | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

| Formulation | NaCl concentration |
|---|---|
| No salt | 0.0M |
| 3.3× salt | 5.0M |
| Glycerol | Neat glycerol solution instead of buffered saline |

Figure 15:
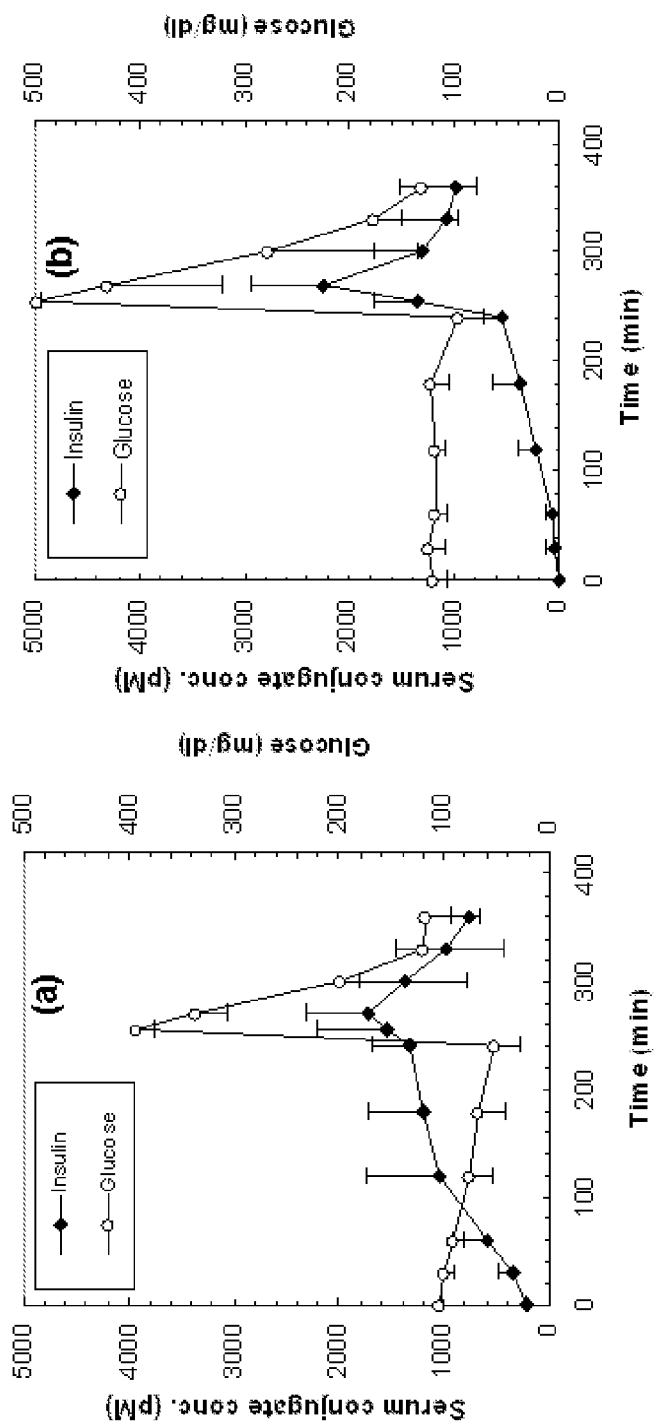
FIG. 15: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared as described in Example 23: (a) no salt, (b) 3.3× salt, and (c) glycerol.
Figure 15:
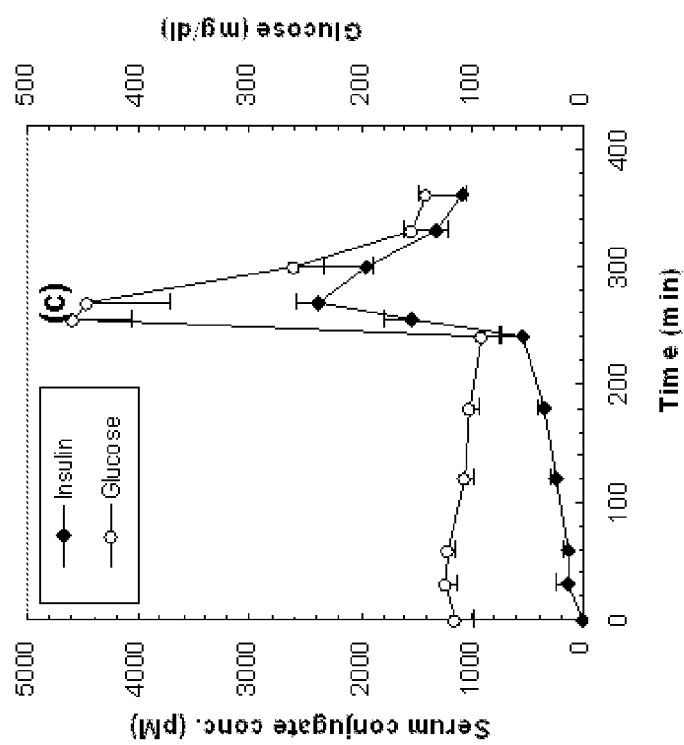

The four hour IP glucose injection (4 g/kg) experiments were performed by dosing 15 U/kg (body weight in grams/1.87=microliters of injection volume) of each of the three formulations described above. The results shown in FIG. 15a-c demonstrate that the presence of salt in the formulation maintains a more protracted formulation. The no salt formulation released a significant portion of the insulin conjugate payload over the first four hours of the experiment such that very little increase in measured insulin concentration is observed when challenged with IP glucose. On the other hand, the 3.3× salt formulation released a low basal amount of conjugate over the first four hours with no hypoglycemia and subsequently attained a ~4× increase in measured insulin concentration immediately following the IP glucose injection. This performance was similar to that obtained with the 10×P–4×Z formulation from Example 20, which was exactly the same as the 3.3× salt formulation but contained approximately ⅓ the salt concentration (1.5 M as compared to 5.0 M). Finally, substituting glycerol for NaCl as the isotonic agent does not appear to adversely affect the protracted nature of the formulation.

Example 24

Effect of Unmodified Insulin Concentration on Long Acting Insulin Conjugate Performance The purpose of this example was to demonstrate the effect of including different concentrations of unmodified insulin on the time action and glucose-responsive PK profile of an exemplary conjugate. In this example I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | % unmodified insulin = see below | 1.000 |

-continued

| Component | Variable | Volume (ml) |
|---|---|---|
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

| Formulation | % unmodified insulin |
|---|---|
| 1/24 | 4.17 |
| 1/12 | 8.33 |
| 1/6 | 16.7 |

Figure 16:
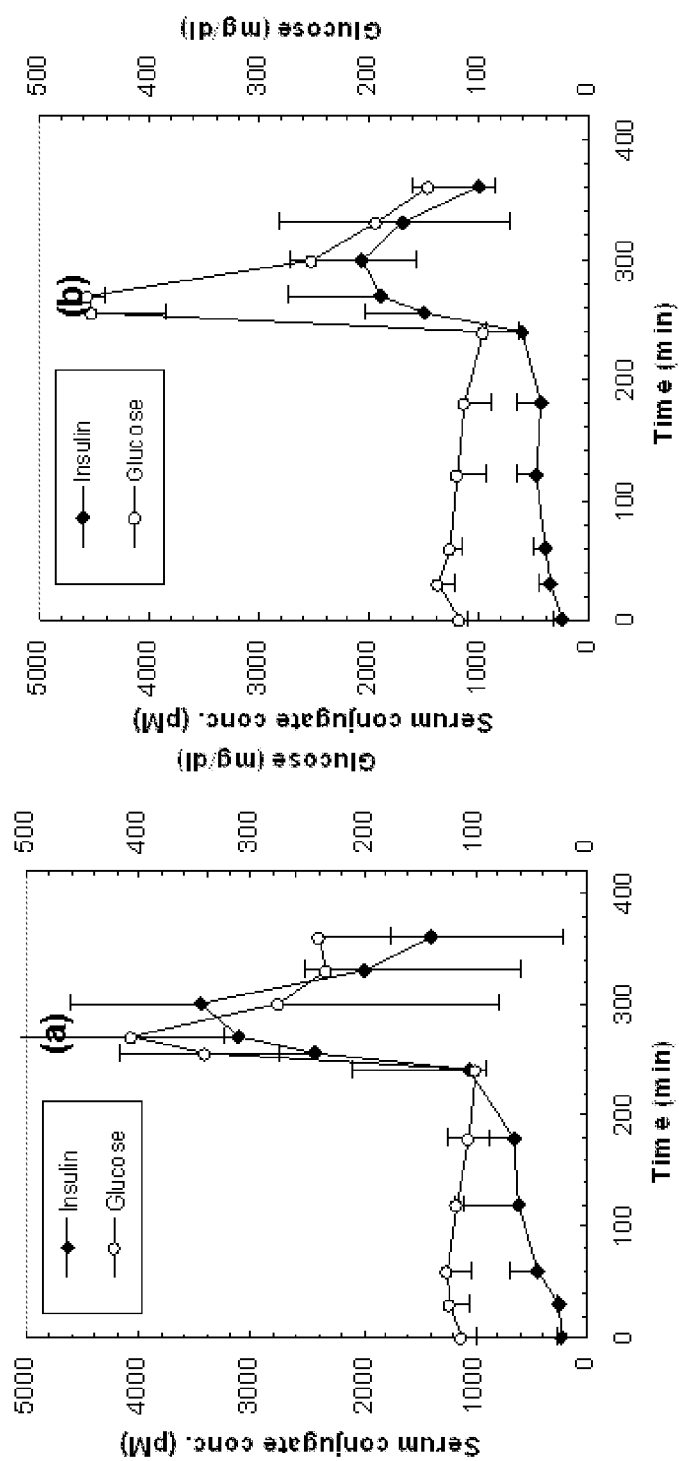
FIG. 16: Plots of serum insulin (♦) and blood glucose (○) levels following subcutaneous injection in non-diabetic, male SD rats (n=3 per dose) at time 0 with long-acting conjugate I-6 followed by IP injection of glucose (4 g/kg) at 240 minutes. Formulations were prepared containing increasing amounts of unmodified insulin as described in Example 24: (a) 1/24, (b) 1/12, and (c) 1/6.
Figure 16:
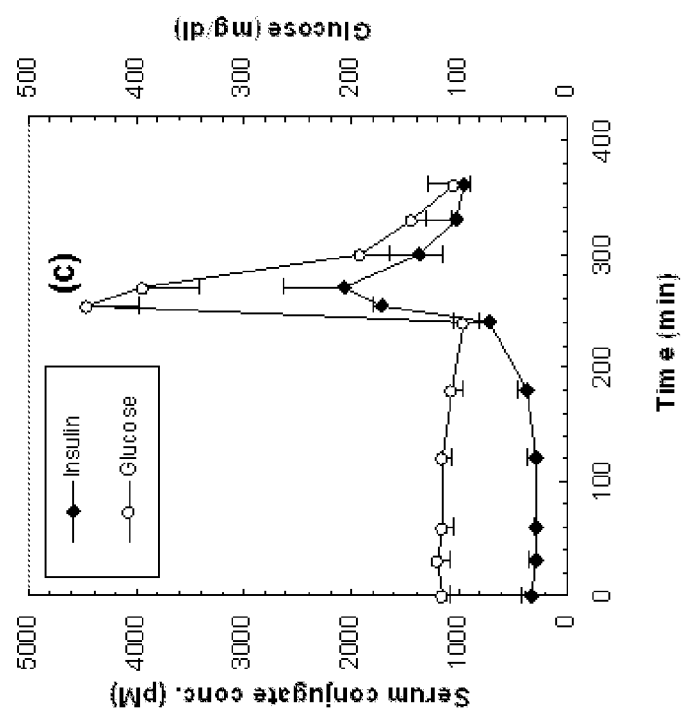

The four hour IP glucose injection (4 g/kg) experiments were performed by dosing 15 U/kg (body weight in grams/1.87=microliters of injection volume) of each of the three formulations described above. The results shown in FIG. 16a-c demonstrate that the presence of unmodified insulin in the formulation beneficially produces a more protracted formulation with substantial increase in measured insulin concentration following an IP glucose injection. Furthermore, the presence of unmodified insulin helps preserve the formulation performance even after several weeks of room temperature incubation (see Example 26 below).

Example 25

Long Acting Insulin Conjugates—Dose Response Effect

In this example, we evaluated the dose-response effect of a particular formulation of a long-acting exemplary conjugate. Conjugate I-6, synthesized according to the methods described in Example 9, was tested using the generalized formulation and in vivo protocol described in Example 19:

| Component | Variable | Volume (ml) |
|---|---|---|
| TSAT-C6-AETM-2 (I-6) solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

The four hour IP glucose injection (4 g/kg) experiment was performed by dosing 5 or 15 U/kg (body weight in grams/1.87=microliters of injection volume) of the formulation described above.

Figure 17:
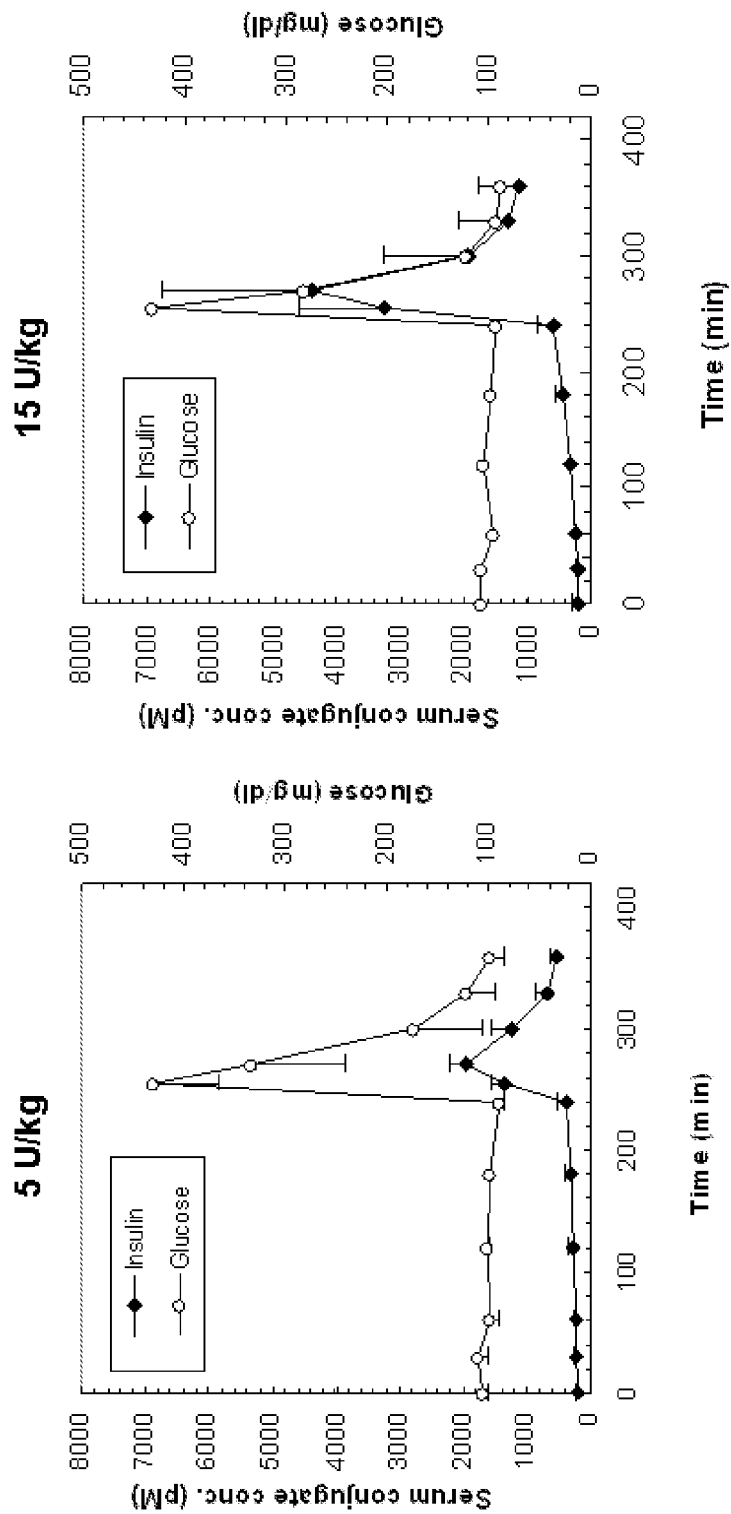
FIG. 17: Plot of serum insulin (♦) and blood glucose (○) levels following subcutaneous injection in non-diabetic, male SD rats (n=3 per dose) at time 0 with a long-acting conjugate I-6 prepared according to Example 25 followed by IP injection of glucose (4 g/kg) at 240 minutes.

As shown in FIG. 17, the conjugate exhibited a flat PK profile until the glucose was injected. The increase in measured insulin concentration following the IP glucose challenge was dramatic and dose-dependent (compare data obtained with a 5 U/kg (left) and 15 U/kg (right) dose of conjugate).

Example 26

Stability of Exemplary Long-Acting, Glucose-Responsive Conjugates

Figure 18:
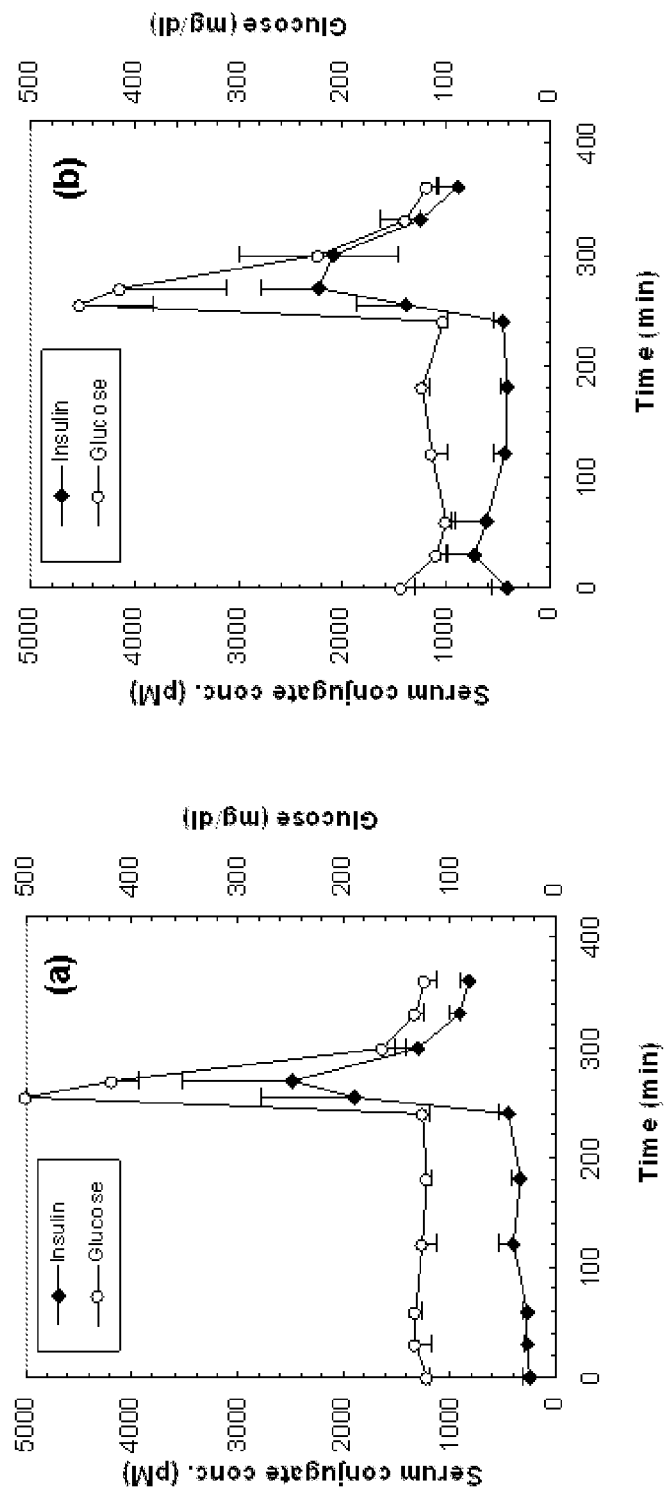
FIG. 18: Plot of serum insulin (♦) and blood glucose (○) levels following subcutaneous injection in non-diabetic, male SD rats (n=3 per dose) at time 0 with long-acting conjugate I-6 prepared according to Example 26 followed by IP injection of glucose (4 g/kg) at 240 minutes. The material was injected after storage at 2-8 C for (a) one week or (b) two weeks.
Figure 19:
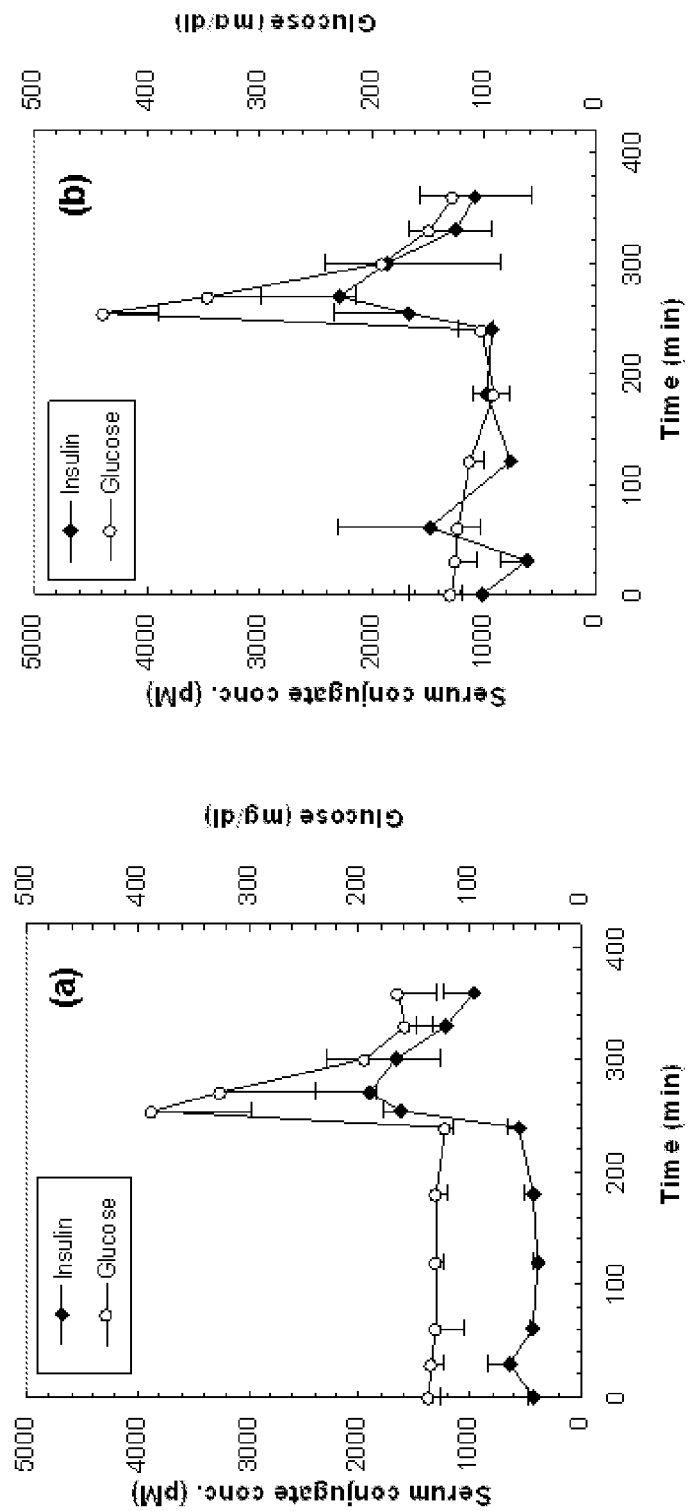
FIG. 19: Plot of serum insulin (♦) and blood glucose (○) levels following subcutaneous injection in non-diabetic, male SD rats (n=3 per dose) at time 0 with long-acting conjugate I-6 prepared according to Example 26 followed by IP injection of glucose (4 g/kg) at 240 minutes. The material was injected after storage at room temperature for (a) one week or (b) two weeks.

In this example, we synthesized the same exact long acting formulation from Example 25 at a 2× scale. Half of the material was stored at 2-8 C and the other half stored at room temperature for one week or two weeks. After the specified storage time, the material was redispersed and tested using the same four hour IP glucose injection protocol described in Example 25 at a 15 U/kg dose (body weight in grams/1.87=microliters of injection volume). As shown in FIGS. 18-19, this formulation demonstrates similar performance even after being stored refrigerated (FIG. 18) or at room temperature (FIG. 19) for at least two weeks.

Example 27

Performance of Long Acting Conjugates Prepared from Conjugates with Varying Ligand Affinity and Multivalency In this example, we set out to determine the time action and glucose-responsive PK profile of long-acting formulations of conjugates constructed from different types and numbers of ligands. All conjugates for this example were synthesized according to the methods described in Example 9 using the frameworks and saccharide ligands specified below:

| Conjugate | Framework | Framework MW | Ligand | AE-sugar MW | Purity (HPLC) | MW (LC-MS) | Sugar/Insulin |
|---|---|---|---|---|---|---|---|
| I-8: DSS-AEM-1 (B29) | DSS | 368 | AEM | 223 | >95% | 6168 | 1.0 |
| I-7: TSAT-C6-AEM-2 (B29) | TSAT-C6 | 822 | AEM | 223 | 95% | 6729 | 2.0 |
| I-9: TSPE-AEM-3 (B29) | TSPE | 813 | AEM | 223 | >95% | 6829 | 3.0 |
| I-10: DSS-AETM-1 (B29) | DSS | 368 | AETM | 547 | >95% | 6491 | 1.0 |
| I-11: TSPE-AETM-3 (B29) | TSPE | 813 | AETM | 547 | >95% | 7800 | 3.0 |
| I-17: C6-amide-AEM-2 (B29) | C6-amide | 838 | AEM | 223 | 95% | 6745 | 2.0 |

The following long-acting formulation was used for each conjugate:

| Component | Variable | Volume (ml) |
|---|---|---|
| Conjugate solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

The four hour IP glucose injection (4 g/kg) experiments were performed by dosing 15 U/kg (body weight in grams/

Figure 20:
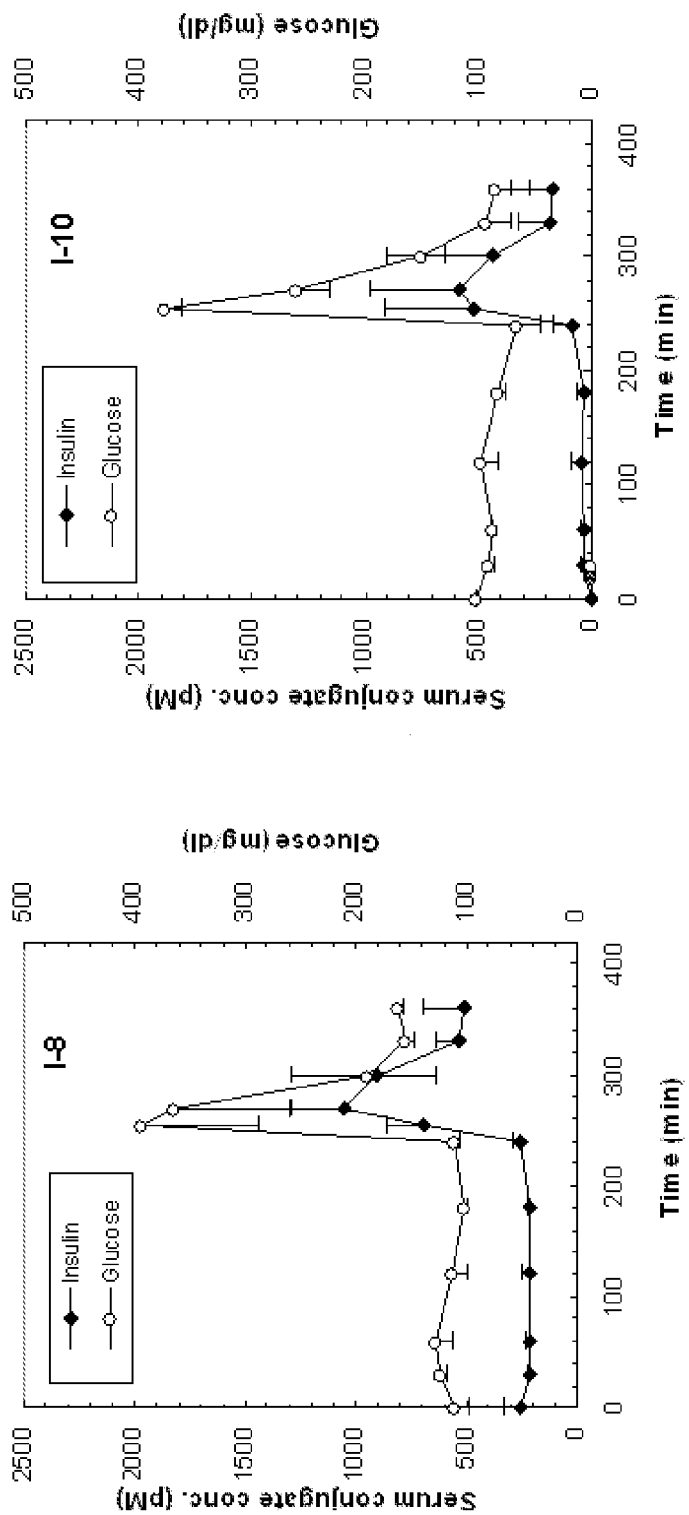
FIG. 20: Plot of serum insulin (♦) and blood glucose (○) levels following subcutaneous injection in non-diabetic, male SD rats (n=3 per dose) at time 0 with long-acting conjugate formulations (I-8, I-10, I-7, I-17, I-9, I-11) prepared according to Example 27 followed by IP injection of glucose (4 g/kg) at 240 minutes.
Figure 20:
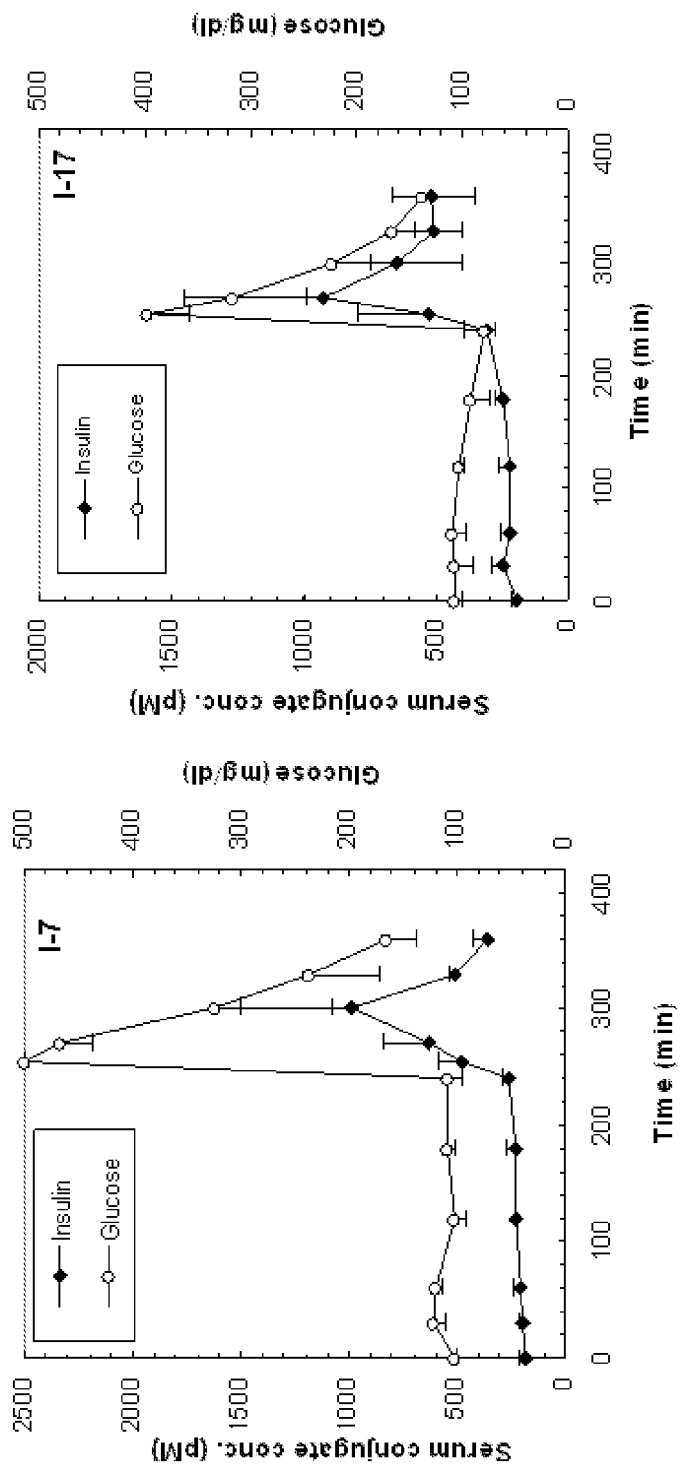
Figure 20:
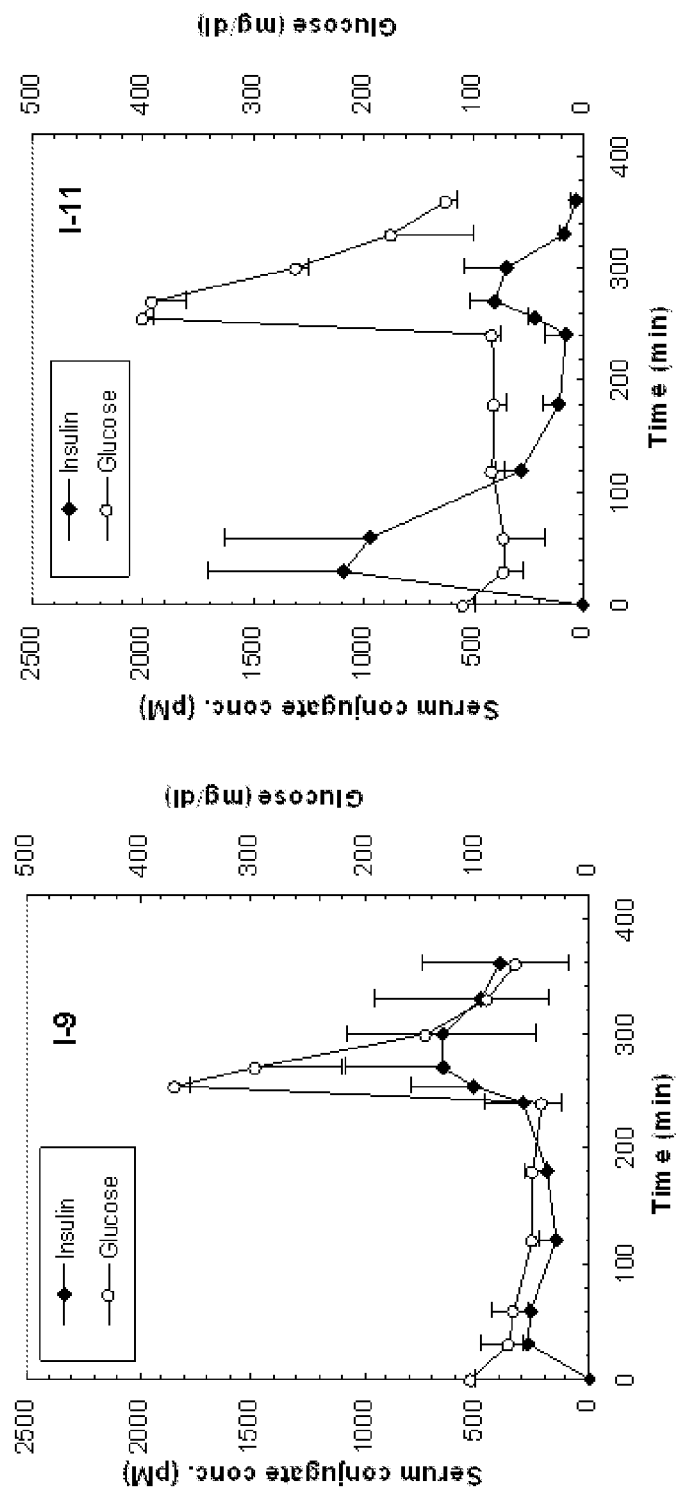

1.87=microliters of injection volume) of each of the conjugates described above. As shown in FIG. 20, all conjugates exhibited a protracted absorption profile with some element of increase in measured serum insulin concentration following the 4 hour glucose injection. It appears that there was some significant conjugate absorption in the first four hours after injection of the long acting TSPE-AETM-3 conjugate I-11. However, all other conjugates exhibited flat absorption profiles like the ones observed for TSAT-C6-AETM-2 conjugates. These results correlate well with the fact that the half-lives of these conjugates are all less than unmodified insulin as described in Examples 16-17 and that each of them demonstrates an a-MM-induced increase in PK/PD profile as described in Examples 14-15.

Example 28

Performance of Long Acting Conjugates Under IP a-MM Testing Conditions

In this example, we tested the a-MM-responsive profile of long-acting formulations of conjugates constructed from TSAT-C6-AETM-2 (I-6) and TSAT-C6-GA-2 (I-5) conjugates. Both conjugates were prepared according to the general methods described in Example 9. In addition, the following long-acting formulation was used for each conjugate:

| Component | Variable | Volume (ml) |
|---|---|---|
| Conjugate solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

To test the sustained release nature of the formulations as well as the a-MM-responsive PK profile, the following experiment was conducted. The formulations were injected at 15 U/kg (body weight in grams/1.87=microliters of injection volume) behind the neck of fasted normal non-diabetic rats (Male Sprague-Dawley, 400-500 gm, n=3). After a 240 minute delay, an a-MM dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden).

Figure 21:
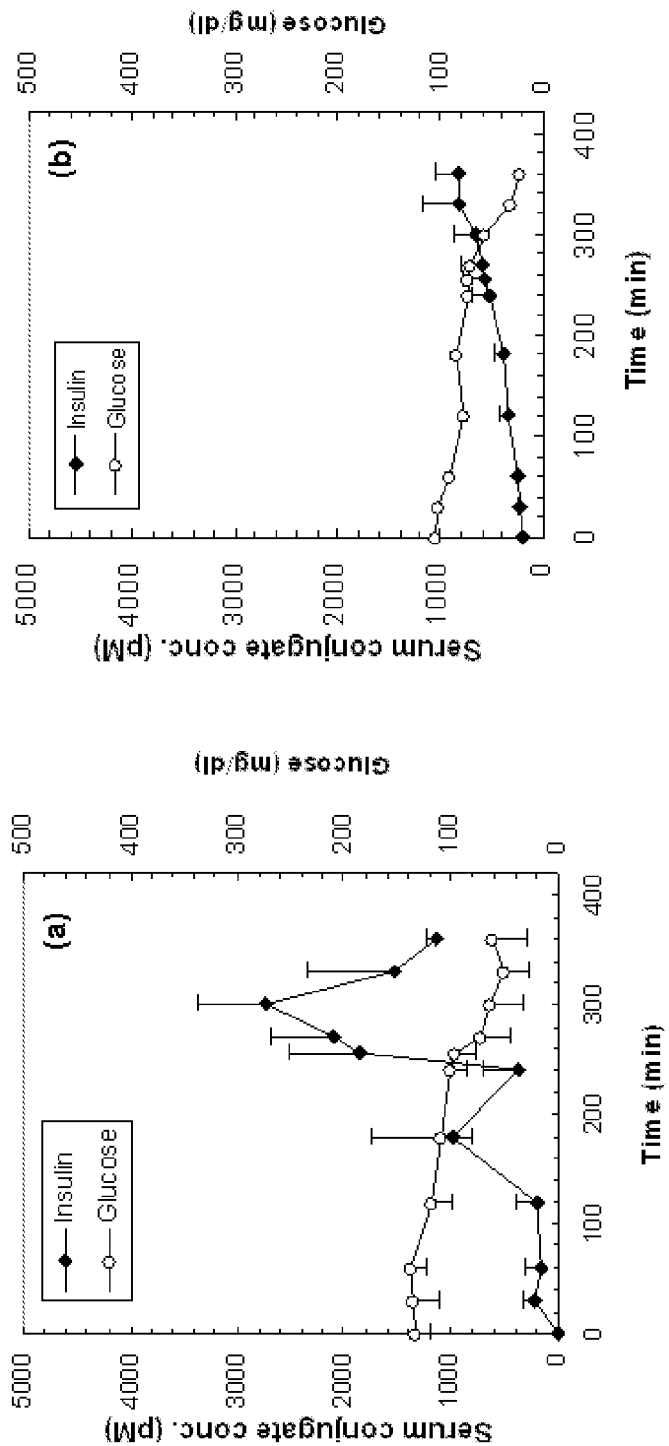
FIG. 21: Plot of serum insulin (♦) and blood glucose (○) levels following subcutaneous injection in non-diabetic, male SD rats (n=3 per dose) at time 0 with long-acting formulations of conjugates I-6 (a) and I-5 (b) prepared according to Example 28 followed by IP injection of alpha-methyl mannose (4 g/kg) at 240 minutes.

As shown in FIG. 21a, the peak:baseline serum concentration ratio following the IP α-MM injection for the long-acting TSAT-C6-AETM-2 (I-6) formulation is even higher than that observed for the same formulation when glucose is substituted for a-MM. Furthermore, the TSAT-C6-GA-2 (I-5) formulation (FIG. 21b) does not demonstrate any increase in serum conjugate concentration following the a-MM challenge. These results correlate well with the fact that the elimination half life of the TSAT-C6-GA-2 (I-5) conjugate is nearly identical to unmodified insulin (Example 16), and that it exhibited no a-MM-induced change in PK (Example 14).

Example 29

Long Acting Conjugates in Diabetics and Non-Diabetics

In order to confirm the in vivo utility of the long acting TSAT-C6-AETM-2 (I-6) formulation, we administered it (5, 10 and 20 U/kg) to normal and STZ-induced diabetic rats (Male Sprague-Dawley, 400-500 gm, n=6). The formulation was prepared using the following procedure:

| Component | Variable | Volume (ml) |
|---|---|---|
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figure 22:
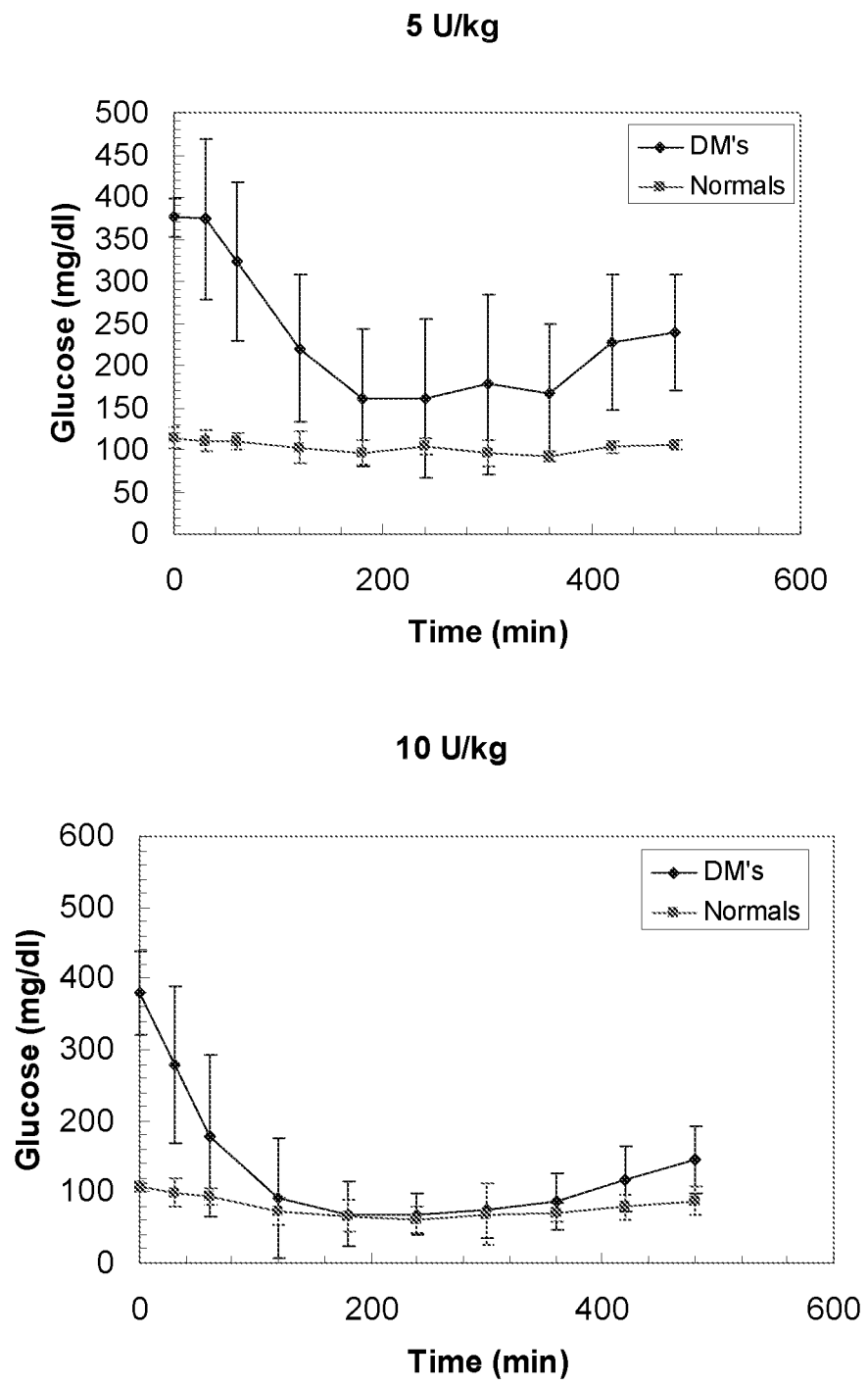
FIG. 22: Plot of blood glucose levels following subcutaneous injection in non-diabetic (normals) and diabetic (DM's) male SD rats at time 0 with PZI conjugate I-6. The conjugate was administered at 5, 10 and 20 U/kg. As shown, the non-diabetic male SD rats did not show any hypoglycemia while the glucose levels in diabetic male SD rats showed a clear dose proportional response that lasted for over 8 hours at the highest dose.
Figure 22:
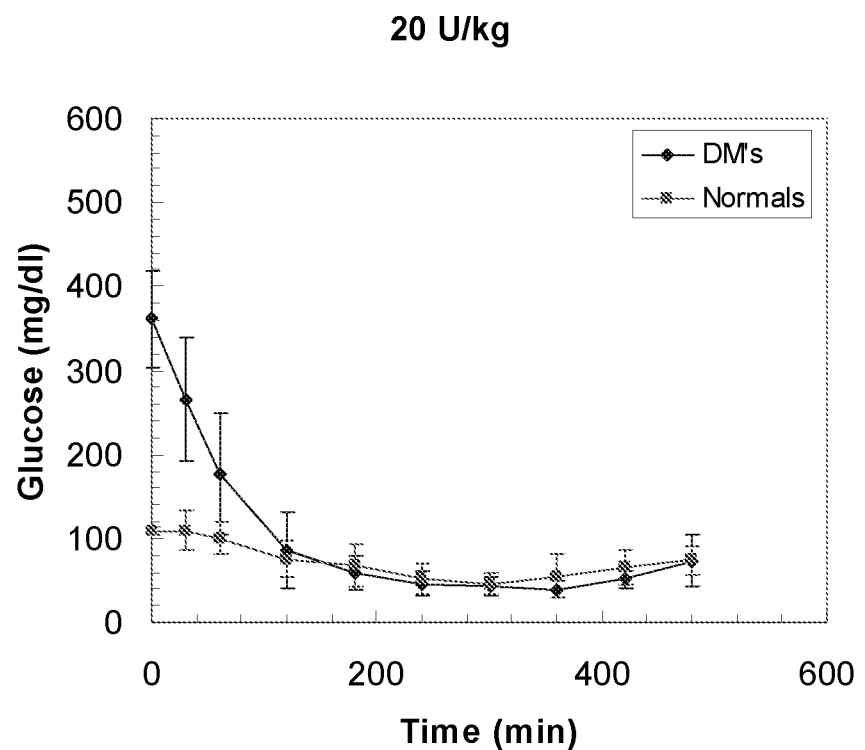

No external IP injections of glucose were used to trigger the bioactivity of the conjugates. Instead we relied on the endogenous levels of glucose in the rats to control the PK and PD profile of the conjugate formulation. Blood samples were collected via tail vein bleeding at various time points after the initial conjugate injection. Blood glucose values were measured using commercially available test strips (Precision Xtra, Abbott Laboratories, Abbott Park, Ill.). As shown in FIG. 22, no hypoglycemia was observed at early or late time points for the normal or diabetic rats. The glucose profiles observed with the diabetic rats are dramatic and demonstrate that the conjugates were activated by the higher glucose concentrations and exerted their glucose-lowering effect in a dose proportional manner over a long time period (over 8 hours at the highest dose).

Figure 23:
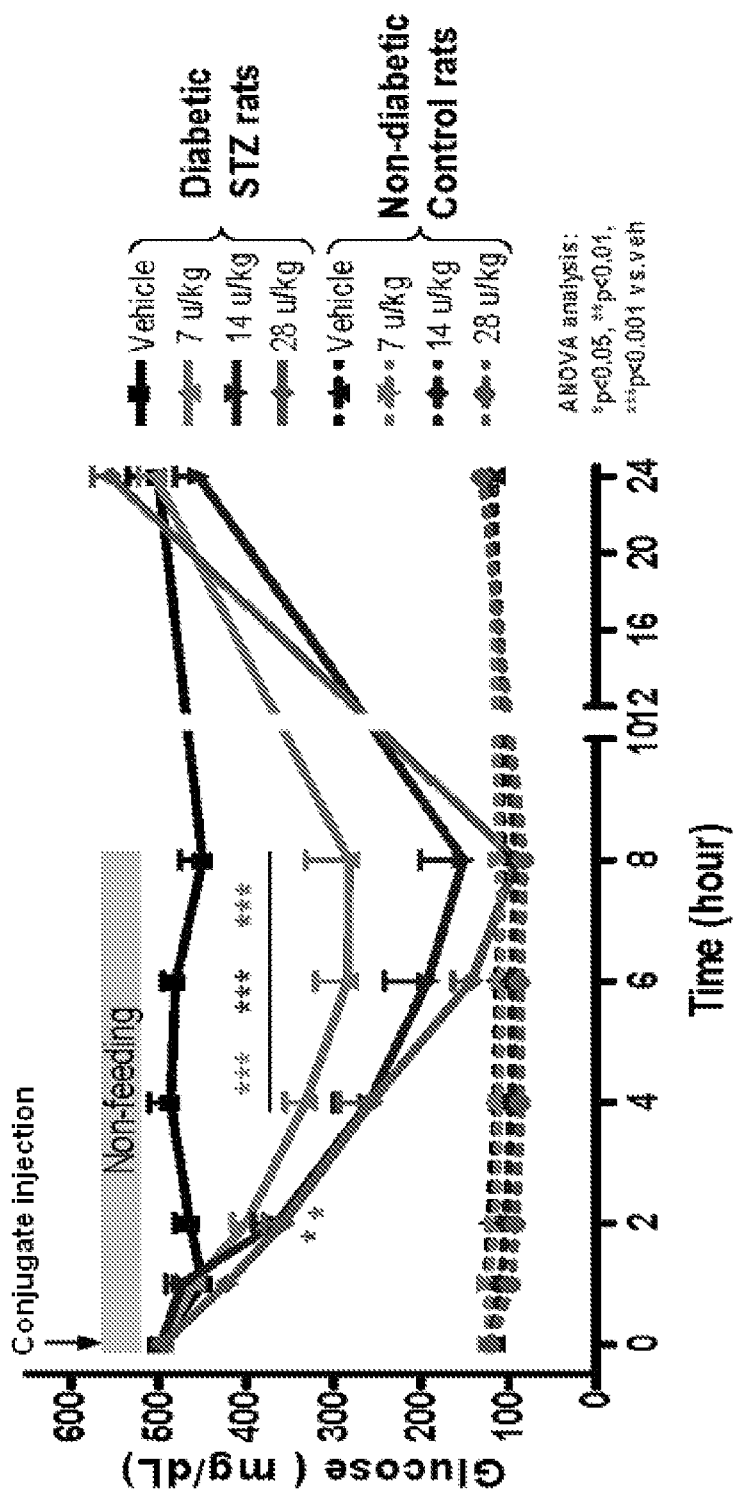
FIG. 23: Plot of blood glucose levels over 24 hours following subcutaneous injection in non-diabetic (normals) and diabetic (DM's) male SD rats at time 0 with PZI conjugate I-6. The conjugate was administered at 7, 14 and 28 U/kg.

The experiment was repeated using different doses (7, 14 and 28 U/kg) and a longer time period (24 hours). Results from that experiment are shown in FIG. 23.

Example 30

In Vivo Half Life/Elimination Rate Comparison

In order to determine the rate at which the I-6 conjugate was cleared from serum in vivo in the presence or absence of inhibitory sugars such as glucose or a-MM, the following experiment was conducted. In each case the soluble conjugate (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Figure 24:
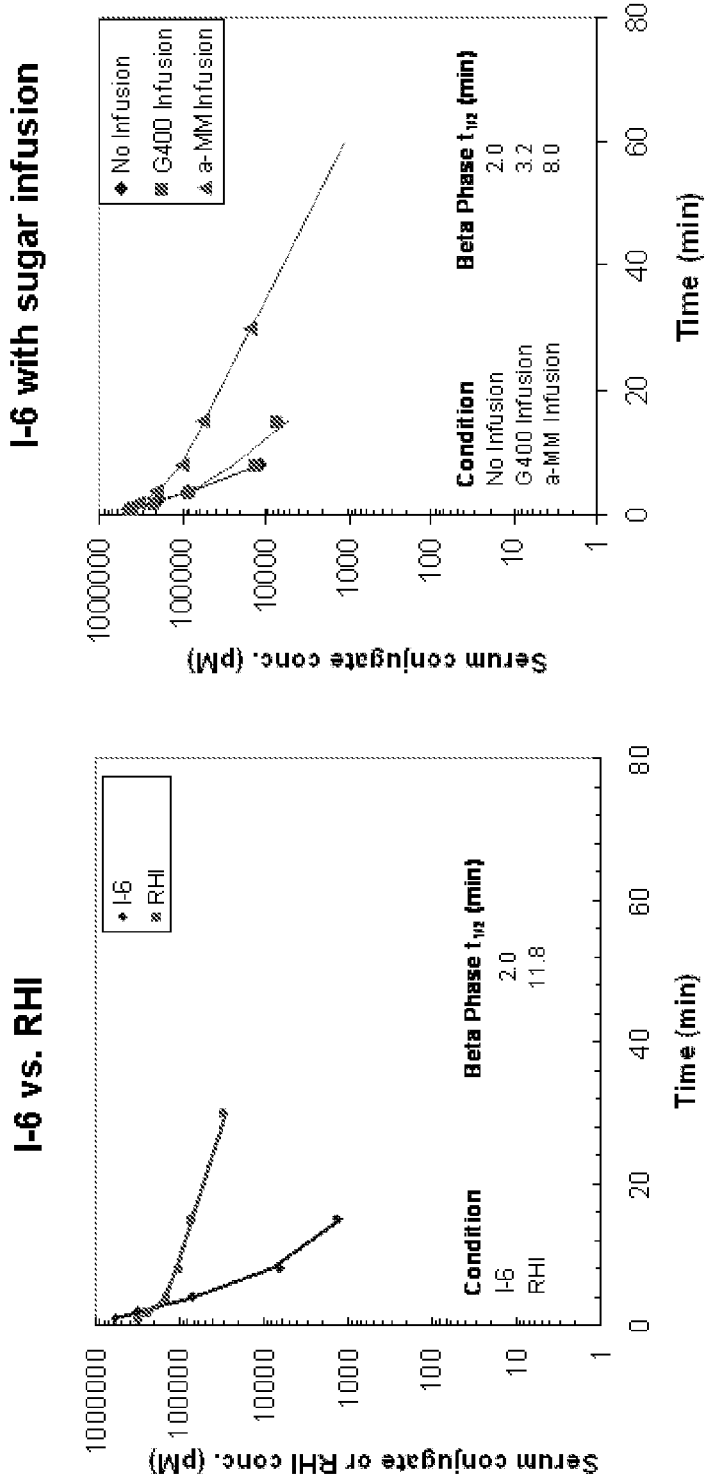
FIG. 24: Plots of serum insulin concentration as a function of time following injection of conjugate I-6 or RHI with and without glucose or α-methyl mannose.

Throughout the experiment, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t\frac{1}{2}(a)=(\ln 2)/k_a$ and $t\frac{1}{2}(b)=(\ln 2)/k_b$. Results are shown in FIG. 24. The left panel demonstrates the significantly higher (>5×) elimination rate for the I-6 conjugate versus RHI in the absence of a-MM or glucose. The right panel shows that the elimination rate decreases somewhat (~50%) in the presence of glucose (G400 infusion) and quite substantially (~400%) in the presence of a-MM (a-MM infusion).

Example 31

Glucose-Responsive PK for I-6 i.v. Infusion

In this example, the i.v. elimination rate experiment described in Example 30 was modified from a single i.v. bolus of 0.4 mg conjugate/kg body weight to a continuous i.v. infusion. The goal of the experiment was to maintain a constant input rate of conjugate (or RHI as a control) for six hours with an i.p. injection of glucose administered at the four hour time point to determine the resulting effect on serum conjugate (or RHI) concentration. Dual jugular vein cannulated male Sprague-Dawley rats (Taconic, JV/JV, 350-400 g, n=3) were used in each experiment such that one jugular vein line was used for conjugate or RHI infusion and the other for blood collection.

For RHI, a 50 mU/ml solution was sterile filtered through a 0.2 um filtration membrane and infused at 0.07 ml/min to provide a constant input rate of 3.5 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 4 g/kg dose of glucose was administered via i.p. injection followed by blood collection at t=255, 270, 300, 330 and 360 min.

For the I-6 conjugate, a 150 mU/ml solution was sterile filtered through a 0.2 μm filtration membrane and infused at 0.10 mL/min to provide a constant input rate of 15 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 1, 2, or 4 g/kg dose of glucose was administered via i.p. injection followed by blood collection at t=255, 270, 300, 330 and 360 min.

Throughout the experiments, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden).

Figure 25:
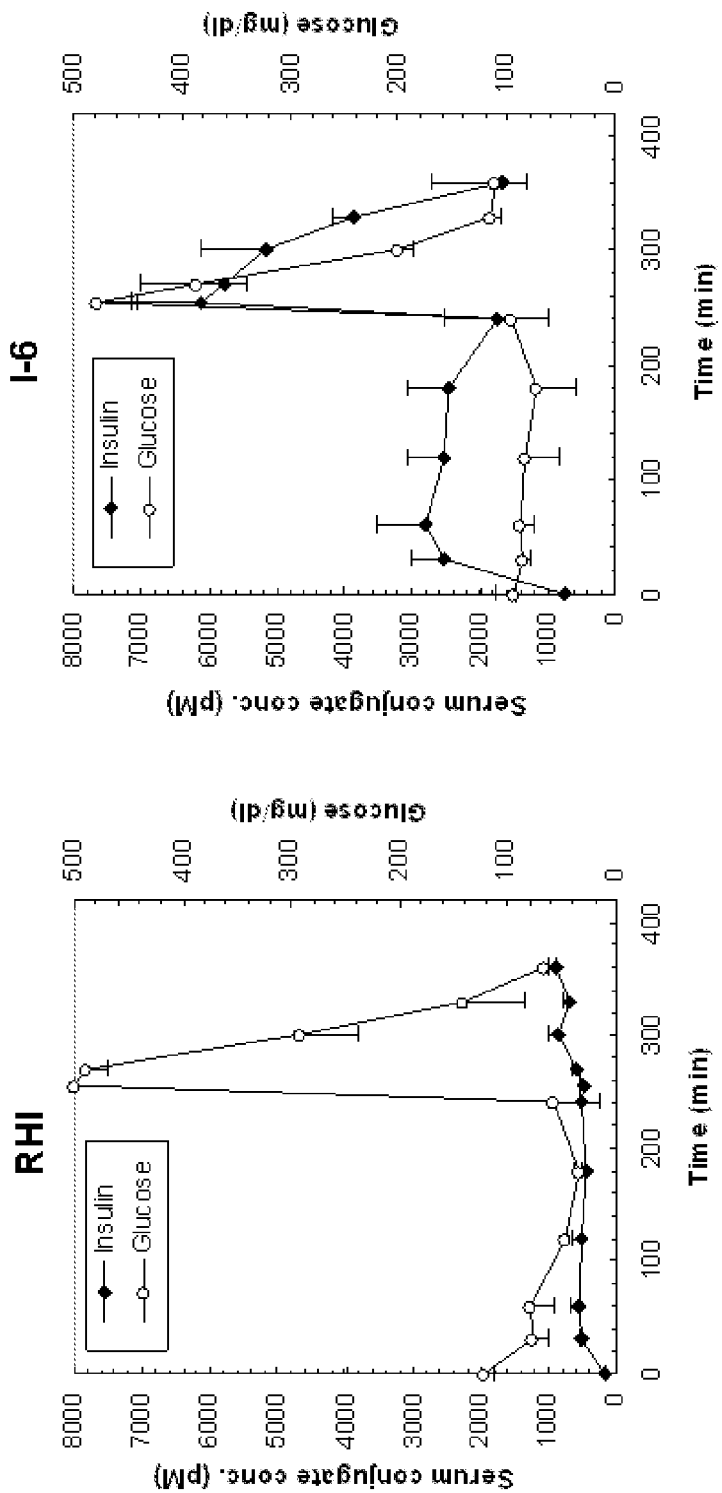
FIG. 25: The first two panels show plots of serum insulin (♦) and blood glucose (○) levels following constant intravenous (i.v.) infusion of RHI (3.5 mU/min) or I-6 (15 mU/min) in non-diabetic, male SD rats (n=3). IP injection of glucose (4 g/kg) was given at 240 minutes. The next three panels compare plots of serum insulin (♦) and blood glucose (○) levels following constant intravenous (i.v.) infusion of RHI (3.5 mU/min) or I-6 (15 mU/min) in non-diabetic, male SD rats (n=3) when an IP injection of glucose (4, 2, or 1 g/kg) was given at 240 minutes.
Figure 25:
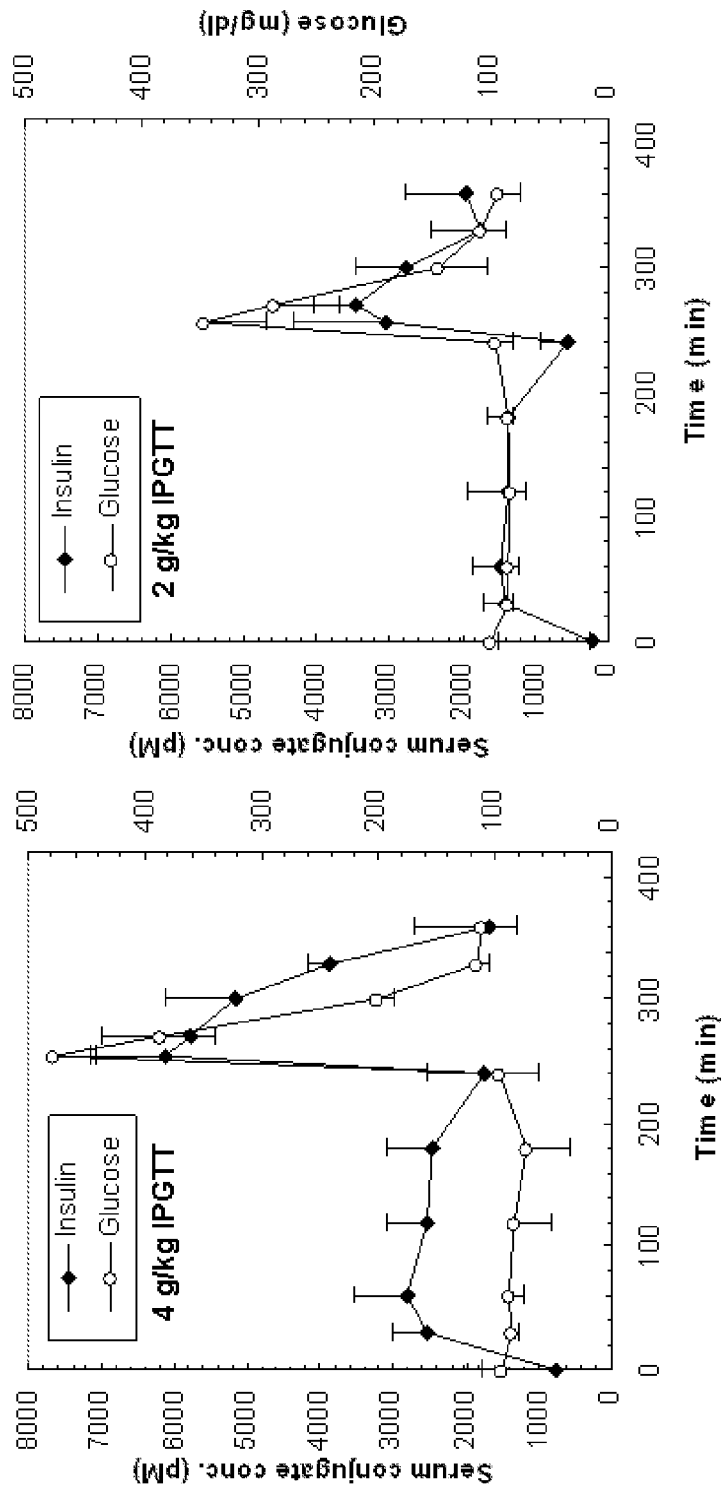
Figure 25:
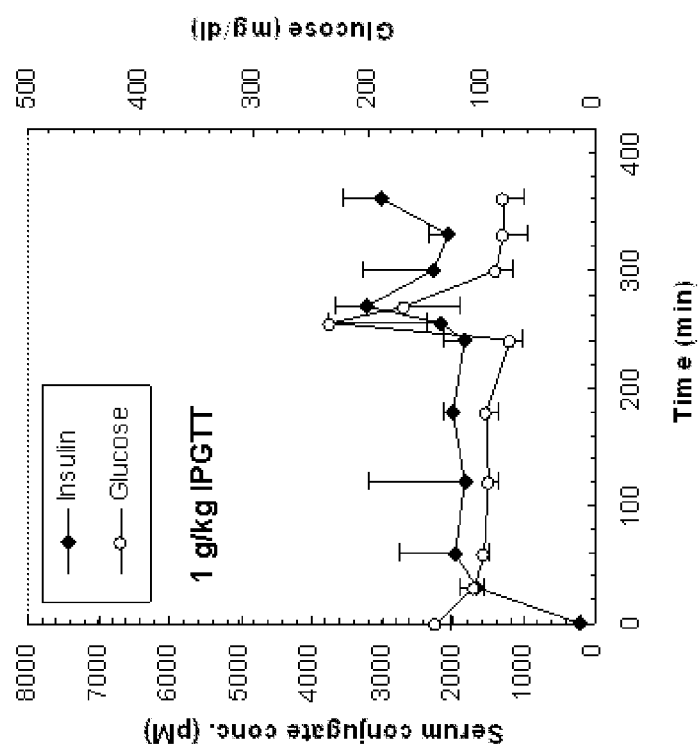

The first two panels of FIG. 25 compare the blood glucose and serum insulin/conjugate concentration profiles for a 3.5 mU/min infusion of RHI and 15 mU/min infusion of I-6 before and after a 4 g/kg i.p. glucose injection. RHI infusion causes significant hypoglycemia prior to glucose injection compared to the I-6 infusion. Following the i.p. glucose injection, the measured serum insulin concentration of I-6 immediately increases by over 300% as the blood glucose concentration increases followed by a rapid return to baseline levels as the glucose concentration decreases. On the other hand, there is no significant change in measured serum insulin concentration for RHI after i.p. glucose injection under the same experimental conditions. The next three panels of FIG. 25 show that the extent to which the measured insulin concentration increases during i.p. glucose injection is directly related to the dose of glucose administered and the resulting blood glucose levels. For example, only a 50% peak to baseline change in serum insulin concentration is observed for the 1 g/kg glucose injection versus the 300% peak to baseline change observed for the 4 g/kg dose.

Example 32

In Vivo Elimination Rate for Insulin-Conjugates with and without Sugar

In order to determine the rate at which the I-9 conjugate was cleared from serum in vivo in the presence or absence of inhibitory sugars such as glucose or a-MM, the following experiment was conducted. In each case the soluble conjugate (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 μL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Figure 26:
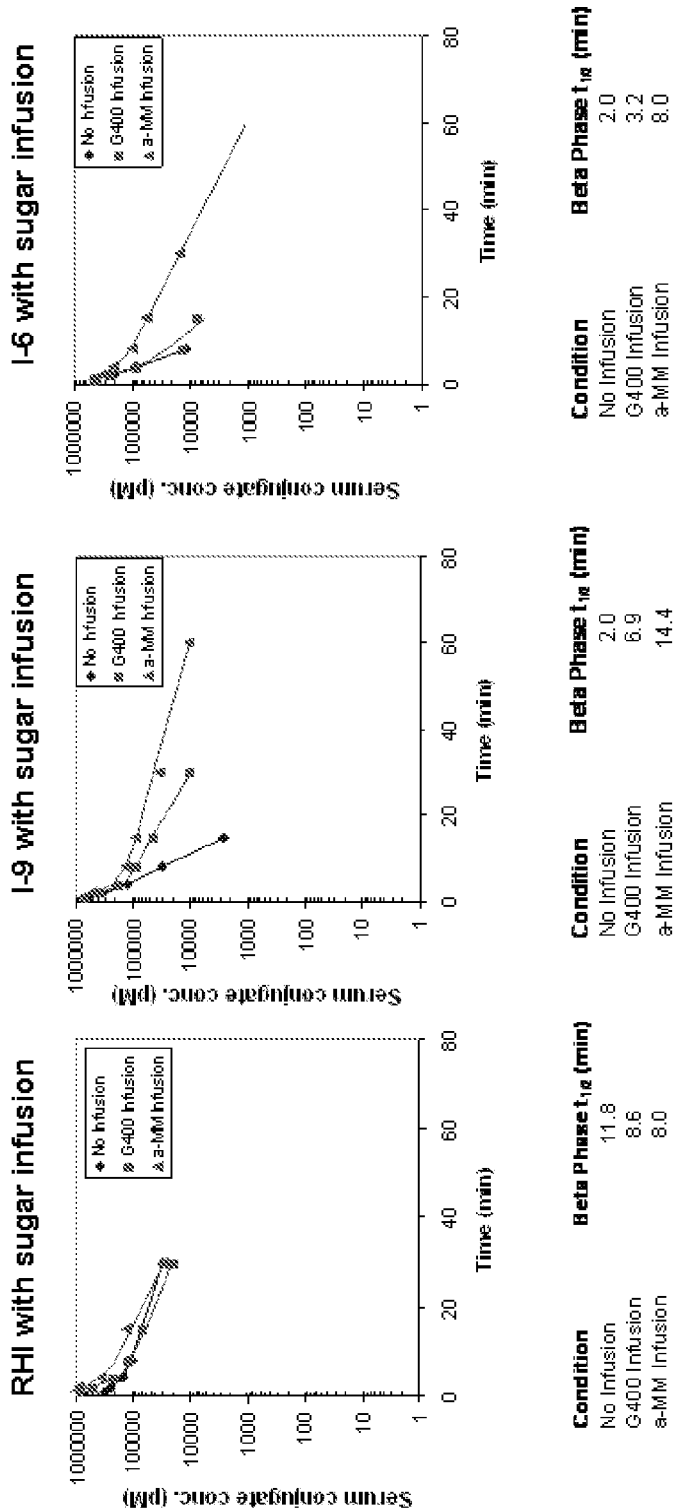
FIG. 26: Plots of serum insulin concentration as a function of time following injection of conjugates with and without glucose or α-methyl mannose. Rats were infused i.v. with sugar solution at t=−60 min and throughout study. Each conjugate was injected at 10 U/kg i.v. at time 0, and serum conjugate concentrations were measured.

Throughout the experiment, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t\frac{1}{2}(a)=(\ln 2)/k_a$ and $t\frac{1}{2}(b)=(\ln 2)/k_b$. The first panel of FIG. 26 shows that the elimination rate of unmodified insulin is not affected in the presence of sugars (glucose G400 or a-MM). For the sake of comparison, the last panel of FIG. 26 showing conjugate I-6 with sugar infusion is replotted from the Example 31 results. The middle panel of FIG. 26 showing conjugate I-9 with sugar infusion shows a much more pronounced decrease in elimination rate (~350% vs. ~50%) in the presence of glucose (G400 infusion) versus the I-6 conjugate. Conjugate I-9 also demonstrates a more significant decrease in elimination rate (~700% vs. ~400%) in the presence of a-MM (a-MM infusion) versus the I-6 conjugate.

Example 33

Crystallization of Conjugate Solutions in Aqueous Buffer

The dispersions of long-acting conjugates synthesized according to Examples 25-27 were confirmed to be amorphous (non-crystalline) by light and scanning electron microscopy. Conventional unconjugated insulin dispersions formulated under similar conditions, on the other hand, are usually crystalline. Crystalline formulations of insulin conjugates may be advantageous in improving batch to batch reproducibility, increasing formulation stability, and decreasing particle agglomeration over long periods of storage. Therefore, we set out to determine whether an appropriate set of aqueous conditions exist that are amenable to crystallizing our conjugates.

A set of 48 crystallization screening solutions (HR2-144) was purchased from Hampton Research, Inc. (Alta Vista, Calif.) along with the specially designed Hanging prop Vapor Diffusion plates. Briefly, a thin bead of cover slide sealant was applied to the upper edge of each of the 24 reservoirs on each of two plates. 1 ml of Index reagent 1 was pipetted into reservoir A1, and 1 ml of Index reagent 2 was pipetted into reservoir A2, and so on. 2 microliters of a 2.5 mg/ml conjugate solution in deionized water was added to the center of a clean, siliconized 22 mm diameter circle cover slide and mixed with 2 microliters of the Index reagent 1 from reservoir 1. The cover slide was inverted and sealed over the A1 reservoir so that the droplet was hanging above the reservoir solution. This entire process was repeated for all 48 Index solutions tested, and the plates were allowed to sit at room temperature overnight prior to observation through a light microscope.

Figure 28:
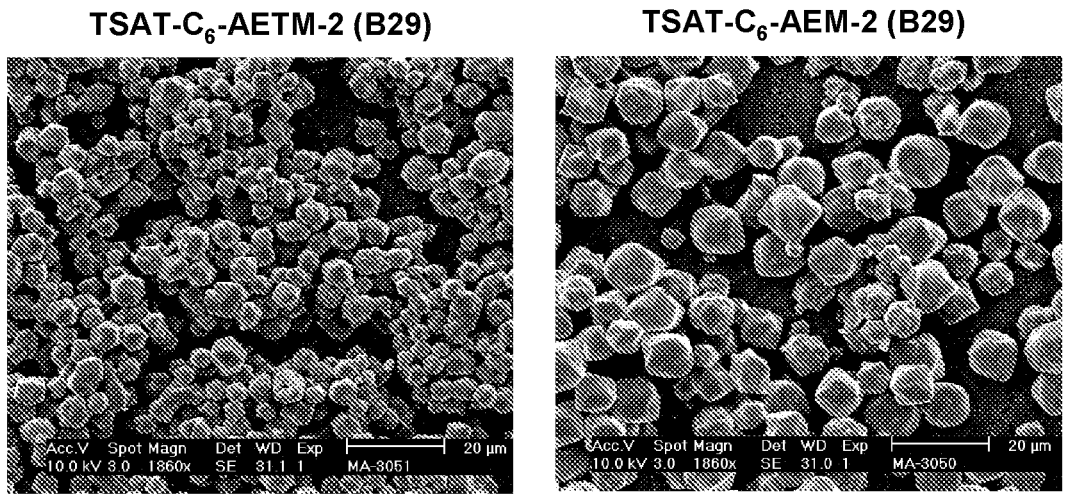
FIG. 28: SEM micrographs of representative crystals formed by mixing Index Buffer 19 with an equal volume of a 2.5 mg/ml solution of conjugate in deionized water (left: I-6; right: I-7).

The results of the screening experiment are summarized in FIG. 27. Most of the 48 Index solutions did not produce crystalline particles or any precipitation at all for that matter. Index Buffer 19 (pH 8.2, 0.056 M Sodium phosphate monobasic monohydrate with 1.344 M Potassium phosphate dibasic) clearly produced the largest quantity of well-defined crystals. Further testing using Index Buffer 19 revealed substantial crystal formation with the TSAT-C$_6$-AEM-2 (B29) and TSPE-AEM-3 (B29) conjugates I-6 and I-9. The structures of these compounds are shown in FIG. 2. FIG. 28 shows scanning electron micrograph (SEM) images of representative crystals formed using Buffer 19 with the TSAT-C$_6$-AETM-2 (B29) and TSAT-C$_6$-AEM-2 (B29) conjugates I-6 and I-7.

Example 34

Long-Acting Neutral Protamine Formulations from Pre-Crystallized Conjugates

A scaled-up batch of crystals synthesized using a 50/50 v/v mixture (0.5 ml of 2.5 mg/ml TSAT-C$_6$-AETM-2 (B29) conjugate I-6 and 0.5 ml of Index Buffer 19) was prepared and allowed to sit for 24 hours at room temperature to enable full and complete crystallization. To 0.5 ml of the resulting dispersion, 0.0795 ml of a 3% m-cresol solution was added followed by 0.097 ml of a 50 mg/ml protamine solution (pH adjusted to 7.0). The resulting dispersion was mixed gently for approximately 2 hours prior to dosing in rats.

The following experiment was conducted to test the sustained release and glucose-responsive PK profiles profile for the crystalline dispersion (no protamine or m-cresol added) as well as the protamine/cresol-containing dispersion described above. Behind the necks of fasted non-diabetic rats (Male Sprague-Dawley, 400-500 gm, n=2 each), the non-protamine crystal dispersion was injected with a volume (in microliters) equal to the animals' body weight (in grams) divided by 2.19, and the protamine/cresol-containing crystal dispersion was injected with a volume (in microliters) equal to the animals' body weight (in grams) divided by 1.62. After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden).

Figure 29:
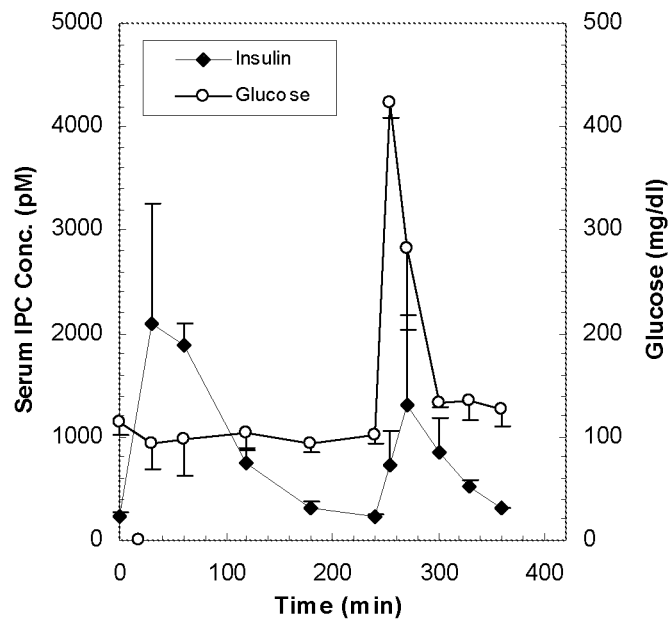
FIG. 29: Plot of (♦) serum insulin-conjugate concentrations and (○) blood glucose levels in fasted, non-diabetic male SD rats (n=2) resulting from a 15 U/kg sub-Q injection of conjugate I-6 crystal dispersion (no protamine or m-cresol) at time 0 followed by a 4 g/kg i.p. glucose tolerance test (IPGTT) at 240 min. Serum insulin levels were measured using an iso-insulin ELISA. Data are plotted as the average values±one standard deviation.
Figure 30:
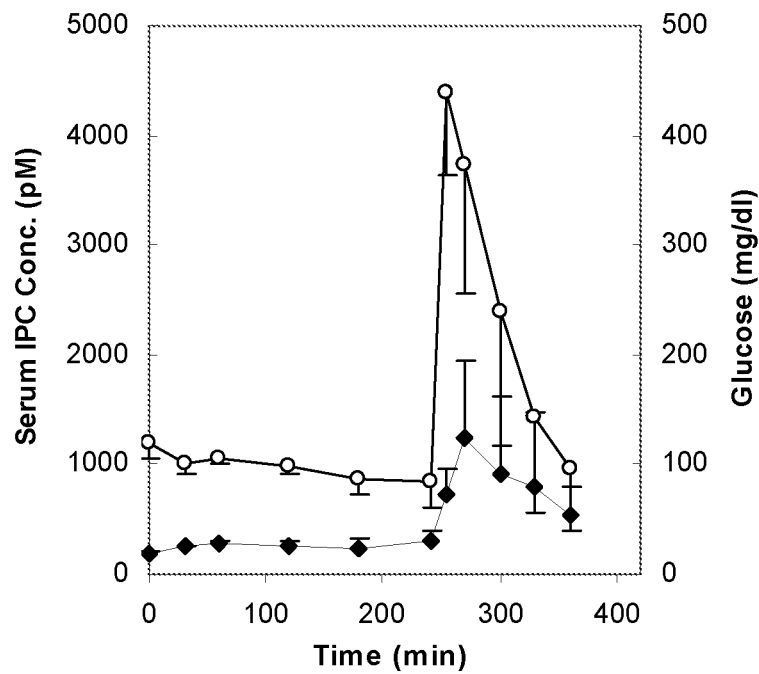
FIG. 30: Plot of (♦) serum insulin-conjugate concentrations and (○) blood glucose levels in fasted, non-diabetic male SD rats (n=2) resulting from a 15 U/kg sub-Q injection of conjugate I-6 crystal dispersion containing protamine and m-cresol at time 0 followed by a 4 g/kg i.p. glucose tolerance test (IPGTT) at 240 min. Serum insulin levels were measured using an iso-insulin ELISA. Data are plotted as the average values±one standard deviation.

As shown in FIG. 30, the protamine/m-cresol-containing crystals exhibited an extremely flat, protracted absorption profile with a significant glucose-responsive increase in serum concentration following the 4 hour glucose injection. The crystalline dispersion without protamine and m-cresol, however, exhibited a large bolus release of conjugate immediately after injection followed by some glucose-responsive increase in serum concentration following the 4 hour glucose injection (FIG. 29). These results indicate the value of combining protamine and m-cresol with the crystals to maintain the desired long-acting pharmacokinetic profile.

This same experiment was repeated with the TSAT-C$_6$-AEM-2 (B29) conjugate I-7. A scaled-up batch of crystals synthesized using a 50/50 v/v mixture (1.0 ml of 2.5 mg/ml conjugate+1.0 ml of Index Buffer 19) was prepared and allowed to sit for 24 hours at room temperature to enable full and complete crystallization. To 1.0 ml of the resulting dispersion from each conjugate, 0.159 ml of a 3% m-cresol solution was added followed by 0.194 ml of a 50 mg/ml protamine solution (pH adjusted to 7.0). The resulting dispersions were mixed gently for approximately 2 h prior to dosing in rats.

Behind the necks of fasted non-diabetic rats (Male Sprague-Dawley, 400-500 gm, n=3 each), the protamine/cresol-containing crystal dispersion was injected with a volume (in microliters) equal to the animals' body weight (in grams) divided by 1.62. After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden). According to the manufacturer's assay specifications, the Iso-Insulin ELISA is 71% cross-reactive with rat insulin. The serum samples were diluted by 10× in order to minimize the amount of endogenous rat insulin detected in each sample but the possibility of rat insulin detection could not be completely ruled out. Therefore, the results are generally reported as "measured insulin," which can consist of some amount of endogenous rat insulin in addition to the conjugate.

Figure 31:
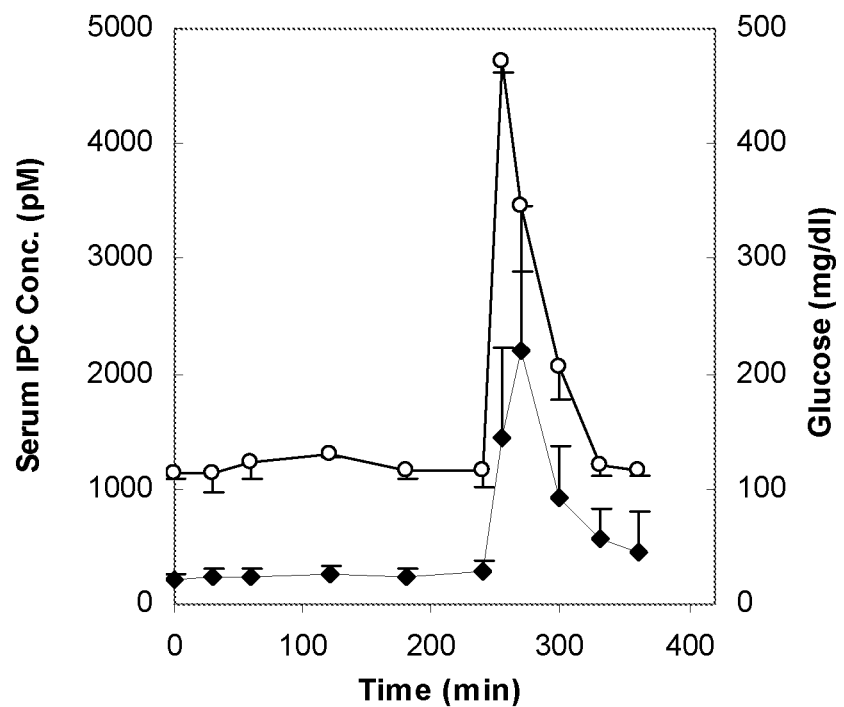
FIG. 31: Plot of (♦) serum insulin-conjugate concentrations and (○) blood glucose levels in fasted, non-diabetic male SD rats (n=3) resulting from a 15 U/kg sub-Q injection of conjugate I-7 crystal dispersion containing protamine and m-cresol at time 0 followed by a 4 g/kg i.p. glucose tolerance test (IPGTT) at 240 min. Serum insulin levels were measured using an iso-insulin ELISA. Data are plotted as the average values±one standard deviation.

As shown in FIG. 31, the protamine/cresol-containing crystals exhibited an extremely flat, protracted absorption profile with a significant increase in measured serum insulin concentration following the 4 hour glucose injection.

The protamine/cresol crystal dispersions described above do not require addition of unconjugated free insulin to maintain stability and improve performance over time. We have found that even after several weeks of refrigerated storage, each crystalline dispersion performs the same as the freshly prepared material.

Example 35

Long-Acting Neutral Protamine Formulations From Pre-Crystallized Conjugates at Physiological Buffer Strength The protamine/cresol-containing crystalline dispersions described above still contain much higher than physiological concentrations of potassium and phosphate that may potentially lead to unwanted injection site inflammation after repeated dosing. The following experiment was performed to determine if the crystals, once formed, were stable in physiological saline containing protamine and cresol. 3.0 ml of TSPE-AEM-3 (B29) conjugate I-9 (2.5 mg/ml) was mixed with 3.0 ml of Buffer 19 and allowed to stand at room temperature overnight to enable full and complete crystallization. The next day, 0.956 ml of 3% m-cresol solution and 1.164 ml of a 50 mg/ml protamine solution (pH 7.0) were added to the resulting dispersion and allowed to sit overnight at 4° C. The next day, the dispersion was centrifuged at 1,000 g for three minutes after which 7.5 ml of supernatant was removed followed by redispersion in 5.6 ml of 1× phosphate buffered saline (PBS). To 2.8 ml of the resulting dispersion, 0.447 ml of 3% m-cresol solution, 0.204 ml of 1×PBS, and 0.338 ml of a 50 mg/ml protamine solution (pH 7.0) were added. The resulting dispersion was stored at 4° C. for week prior to testing in rats.

Figure 32:
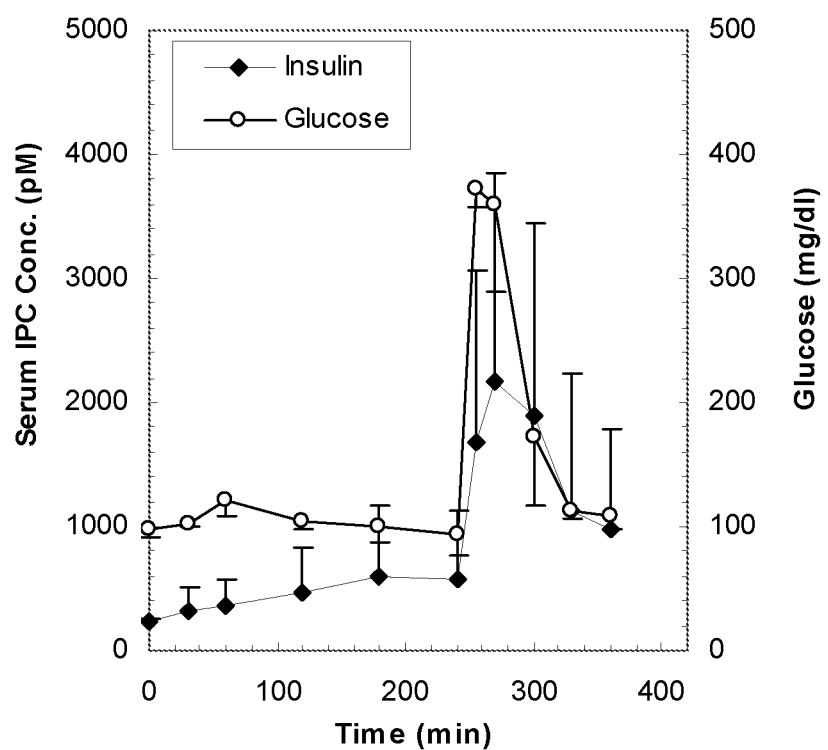
FIG. 32: Plot of (♦) serum insulin-conjugate concentrations and (○) blood glucose levels in fasted, non-diabetic male SD rats (n=3) resulting from a 15 U/kg sub-Q injection of conjugate I-9 crystal dispersion (aged in 1×PBS containing protamine and m-cresol) at time 0 followed by a 4 g/kg i.p. glucose tolerance test (IPGTT) at 240 min. Serum insulin levels were measured using an iso-insulin ELISA. Data are plotted as the average values±one standard deviation.

The aged crystalline dispersion was injected at a volume (in microliters) equal to the animals' body weight (in grams) divided by 1.62 behind the necks of fasted non-diabetic rats (Male Sprague-Dawley, 400-500 gm, n=3). After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden). As shown in FIG. 32, the crystals dispersed and aged in 1×PBS containing cresol and protamine exhibited an extremely flat, protracted absorption profile with a significant glucose-responsive increase in serum concentration following the 4 hour glucose injection.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2

```
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

-continued
I-17
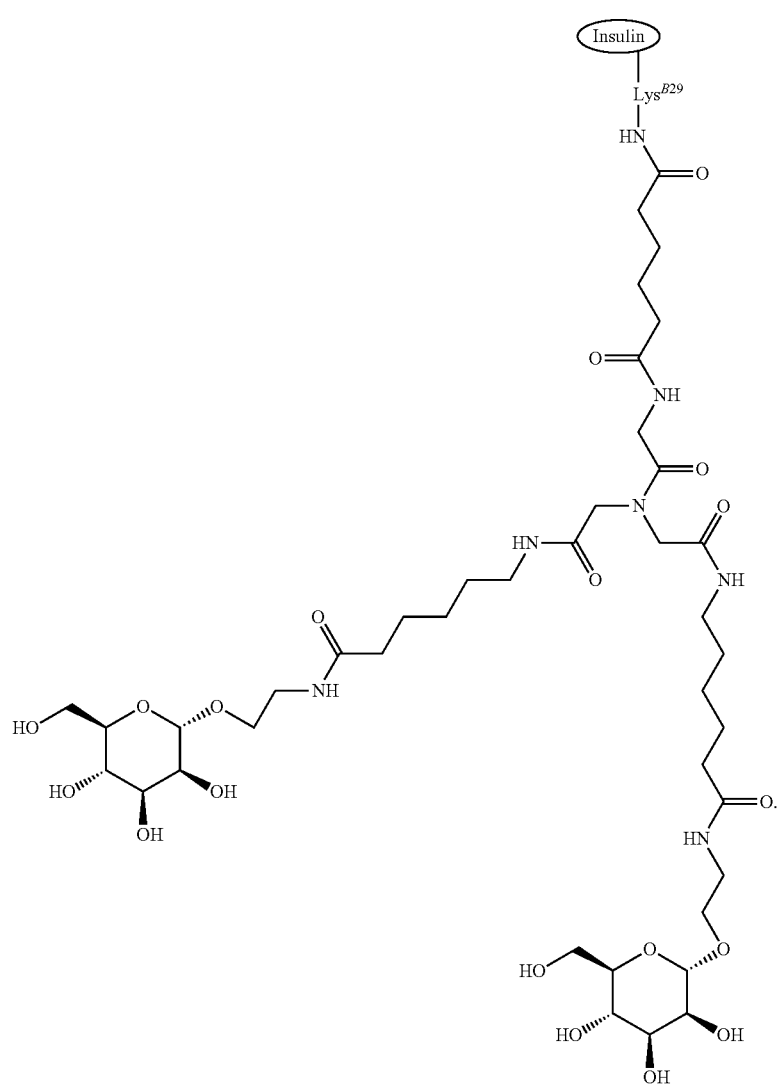

We claim:

1. A crystalline insulin-conjugate of formula (I):

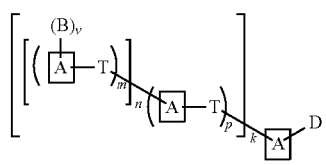

wherein:

each occurrence of [([A]─T)] represents a potential branch within the conjugate;

each occurrence of ([A]─T) represents a potential repeat within a branch of the conjugate;

each occurrence of [A] is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently a ligand that includes a saccharide wherein at least one ligand comprises a branched trisaccharide;

each occurrence of $L^B$ is independently a covalent bond or a group derived from the covalent conjugation of a T with an X;

-D is -T-$L^D$-$W^I$;

$W^I$ is an insulin molecule;

each occurrence of $L^D$ is independently a covalent bond or a group derived from the covalent conjugation of a T with a $W^I$;

k is an integer from 1 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1; and, wherein the conjugate when administered to a mammal in the absence of an exogenous multivalent saccharide-binding molecule, has at least one pharmacokinetic or pharmacodynamic property of the conjugate that is sensitive to serum concentration of a second saccharide.

2. The crystalline insulin-conjugate of claim 1, wherein the conjugate is of formula (IIIa):

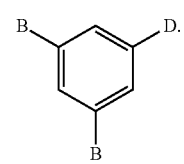

IIIa

3. The crystalline insulin-conjugate of claim 2, wherein the conjugate is of formula (IIIa-1), (III2-2), or (IIIa-3):

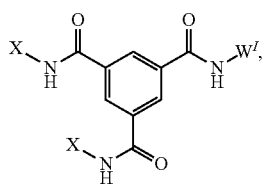

IIIa-1

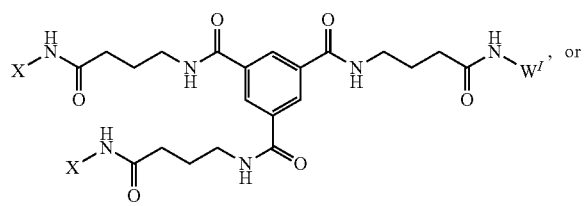

IIIa-2, or

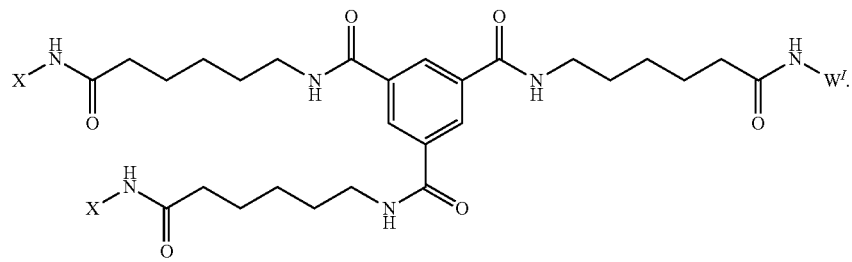
4. The crystalline insulin-conjugate of claim 1, wherein the conjugate is of formula (IIIb):
5. The crystalline insulin-conjugate of claim 4, wherein the conjugate is of the formula (IIIb-1), (IIIb-2), (IIIb-3), (IIIb-4), (IIIb-4), (IIIb-6), (IIIb-7):
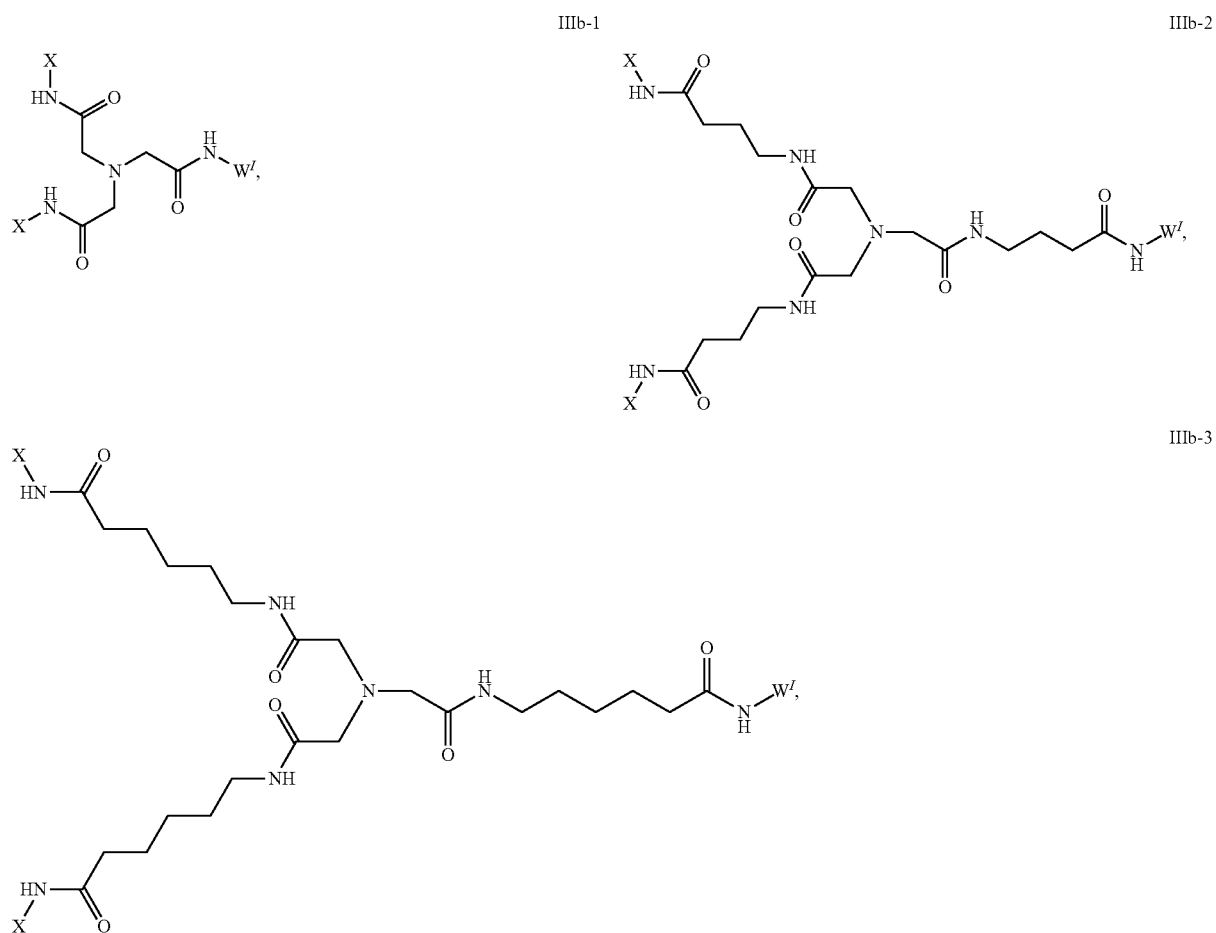

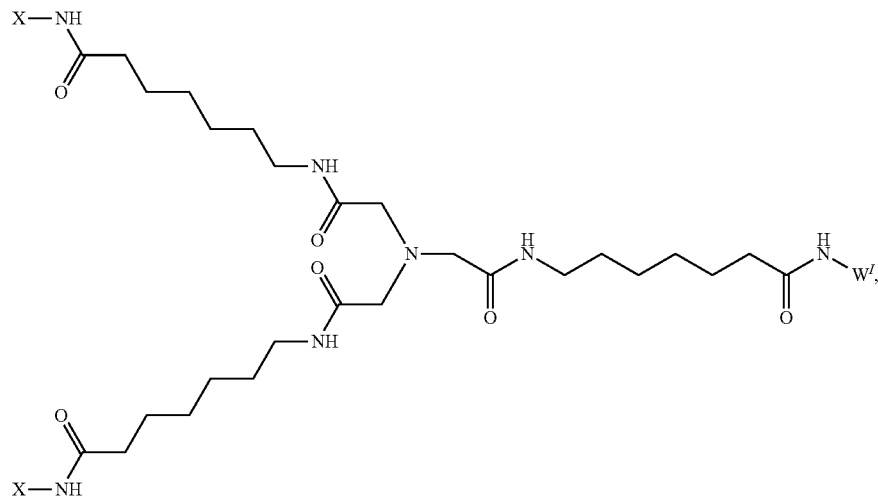
IIIb-4
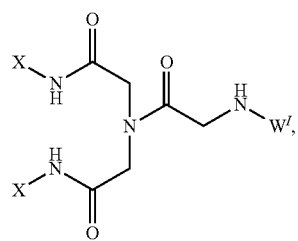
IIIb-5
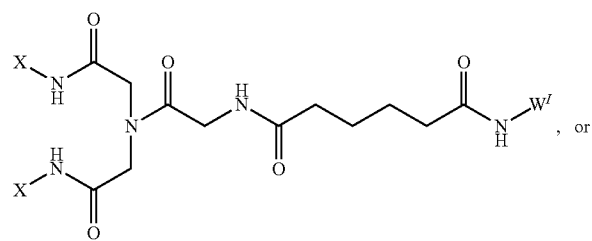
IIIb-6
, or
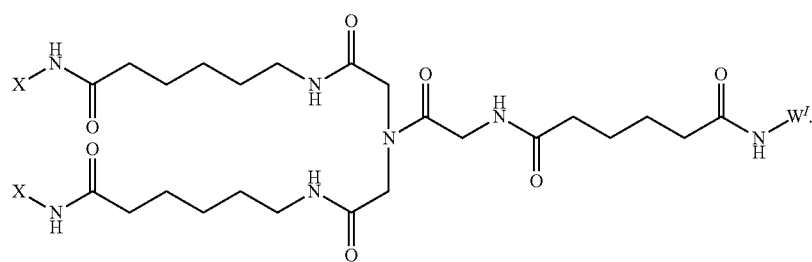
IIIb-7

6. The crystalline insulin-conjugate of claim 1, wherein the conjugate is of formula (IIIc):

IIIc

7. The crystalline insulin-conjugate of claim 6, wherein the conjugate is of formula (IIIc-1) or (IIIc-2):

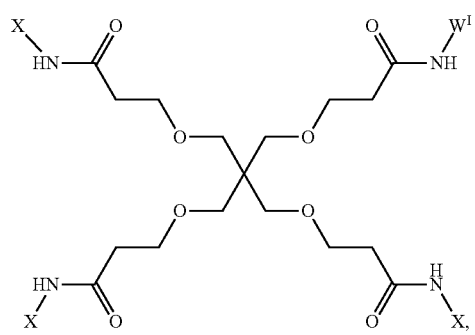

IIIc-1 or

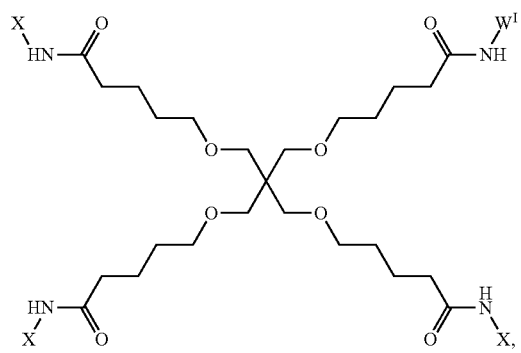

IIIc-2

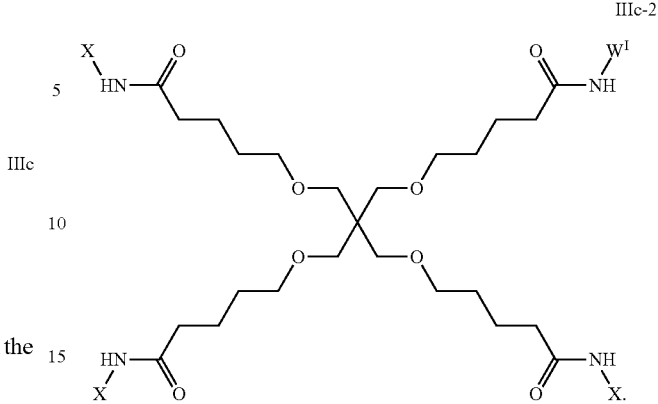

IIIc-2

8. The crystalline insulin-conjugate of claim 1, wherein the insulin molecule is selected from the group consisting of insulin lispro, insulin aspart and insulin glulisine.

9. The crystalline insulin-conjugate of claim 1, wherein the insulin molecule is insulin glargine or insulin detemir.

10. The crystalline insulin-conjugate of claim 1, wherein the insulin molecule is conjugated via the epsilon-amino group of Lys$^{B29}$.

11. The crystalline insulin-conjugate of claim 1, the branched trisaccharide is a branched trimannose.

12. The crystalline insulin-conjugate of claim 1, wherein each occurrence of X is aminoethyltrimannose (AETM).

13. The crystalline insulin-conjugate of claim 1, wherein each occurrence of X is aminoethyltrimannose (AETM) conjugated to the conjugate framework via an alpha anomeric carbon; and W$^I$ is an insulin molecule conjugated to the conjugate framework via the epsilon amino group of Lys$^{B29}$.

14. A crystalline insulin-conjugate of formula (IIIb-3):

IIIb-3

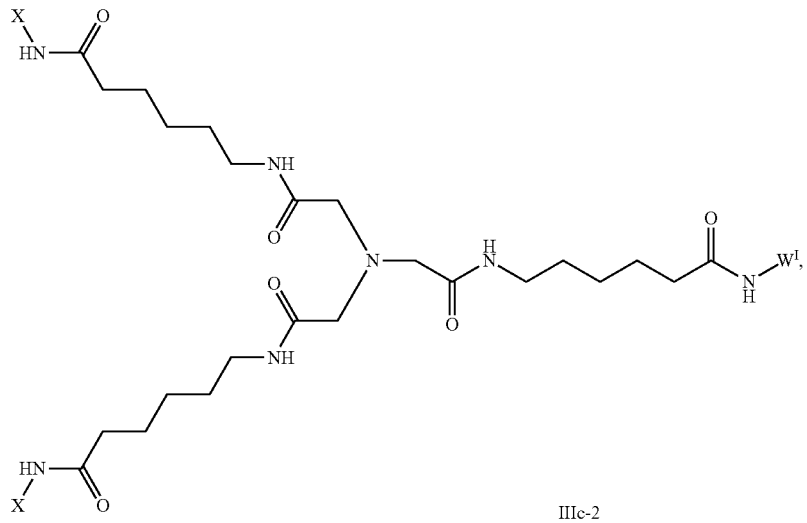

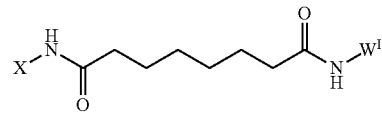

IIId-1 or wherein:
W$^I$ is an insulin molecule; and
each occurrence of —X is
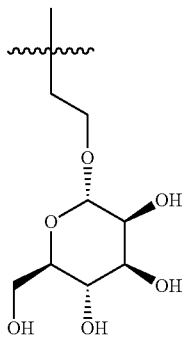
or
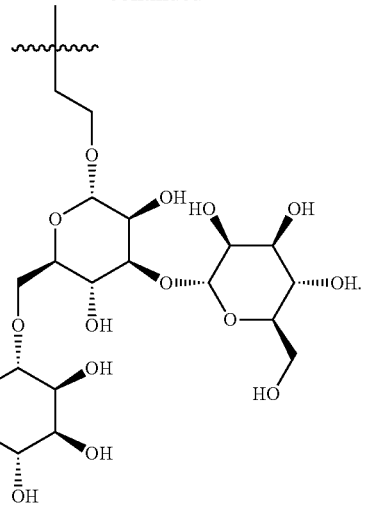
15. A crystalline insulin-conjugate comprising a formula selected from the group consisting of:
I-5
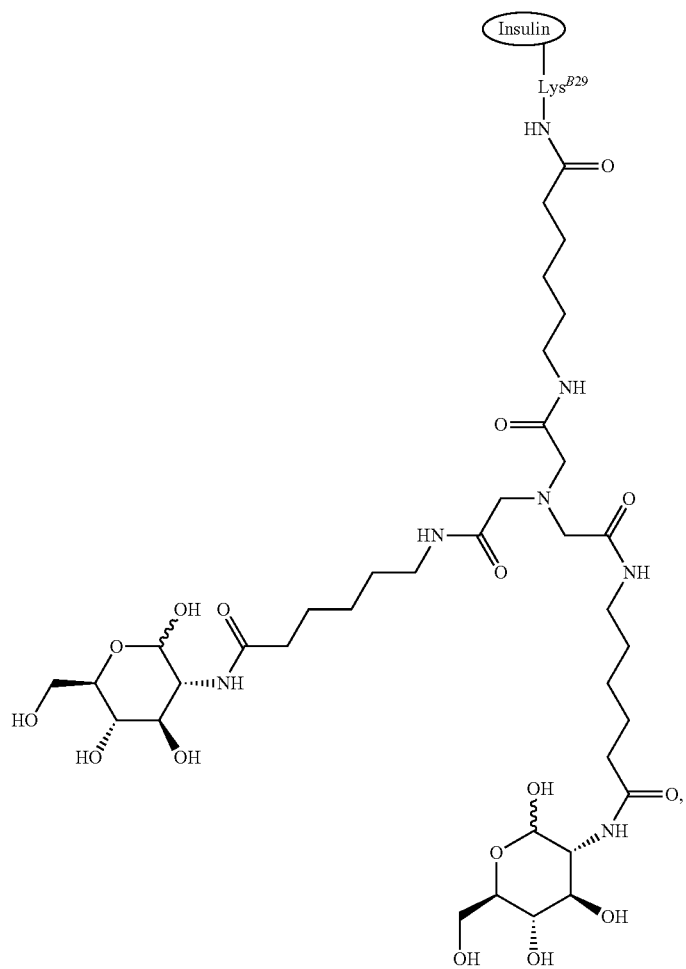

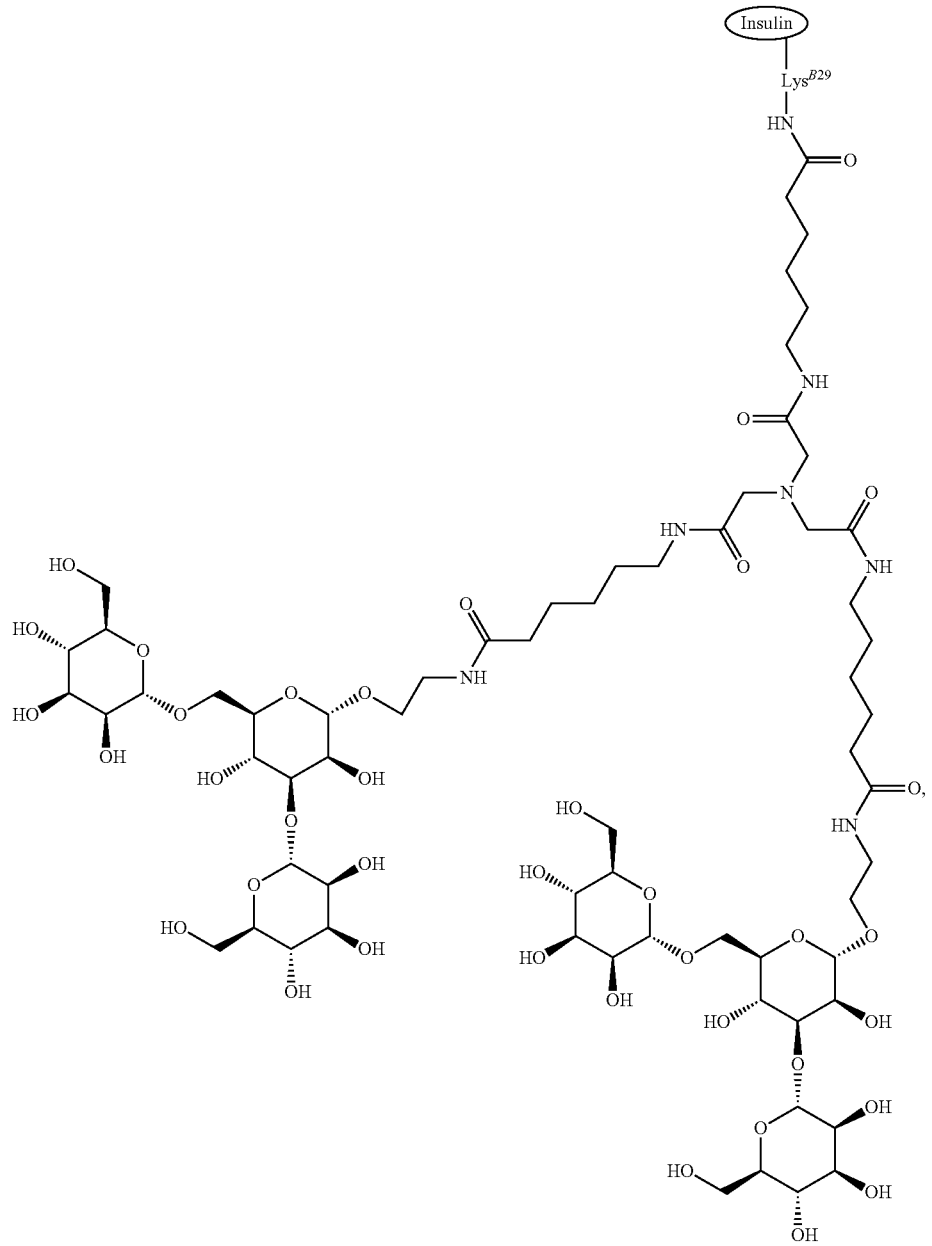
I-6

-continued
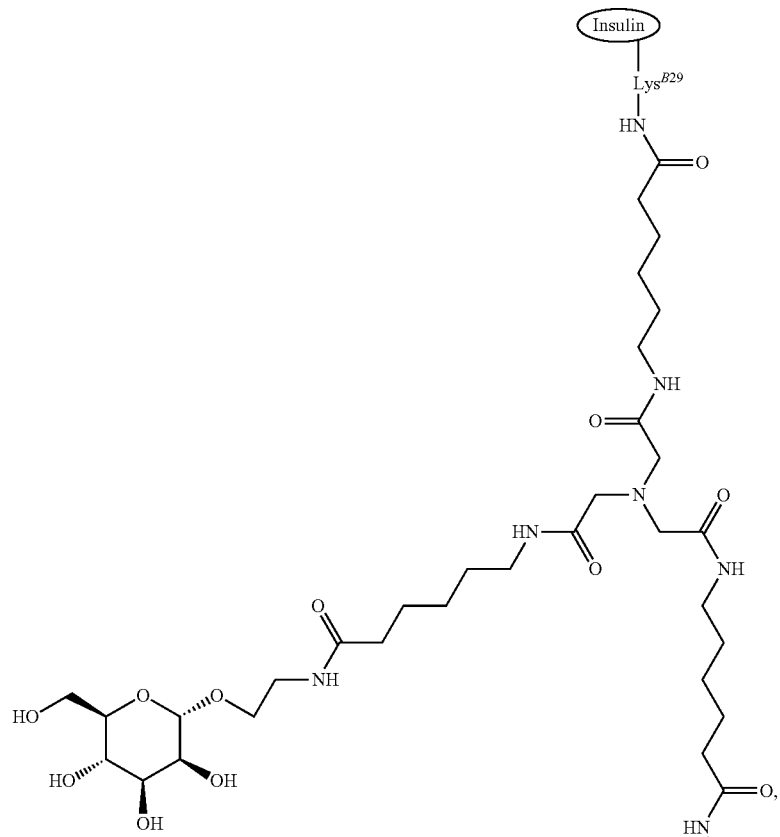
I-7
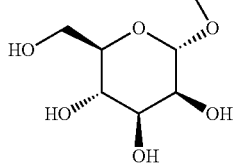
I-8
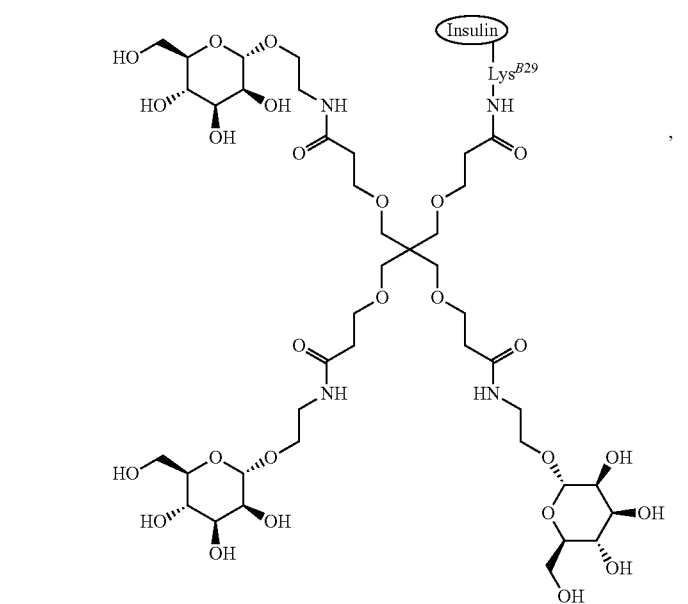
I-9

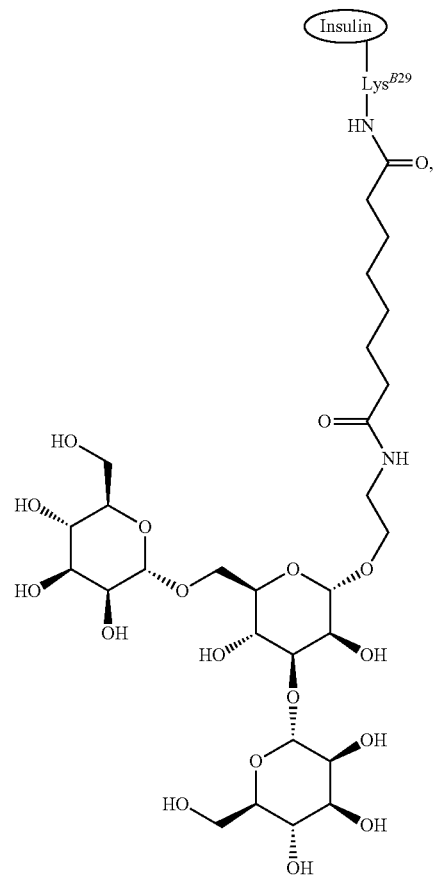
I-10

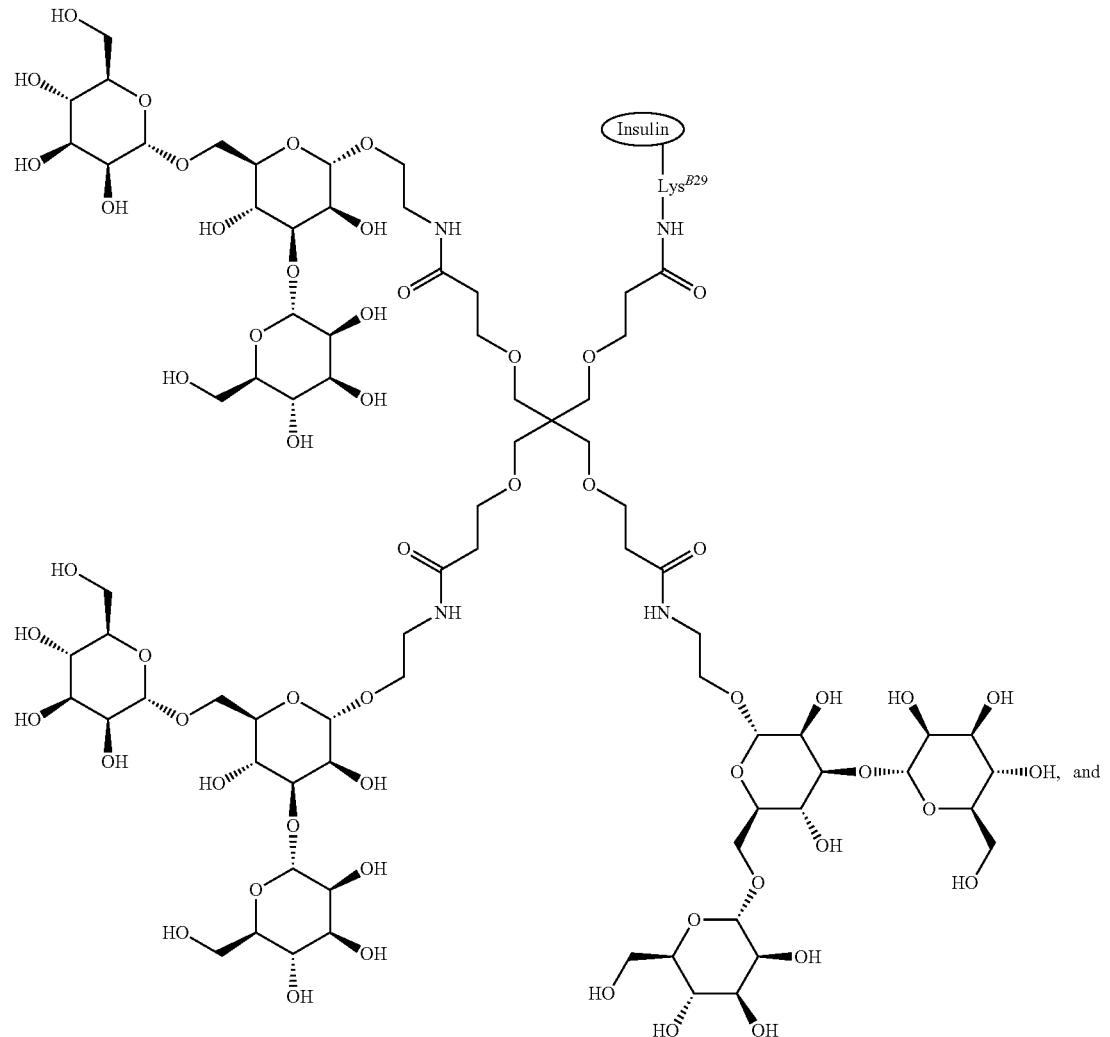
I-11